US009840500B2

(12) United States Patent
Aguirre Ena et al.

(10) Patent No.: US 9,840,500 B2
(45) Date of Patent: Dec. 12, 2017

(54) COMPOUNDS AS DUAL INHIBITORS OF HISTONE METHYLTRANSFERASES AND DNA METHYLTRANSFERASES

(71) Applicant: FUNDACIÓN PARA LA INVESTIGACIÓN MÉDICA APLICADA, Pamplona (ES)

(72) Inventors: Xabier Aguirre Ena, Pamplona (ES); Julen Oyarzabal Santamarina, Pamplona (ES); Felipe Prósper Cardoso, Pamplona (ES); Maria Obdulia Rabal Gracia, Pamplona (ES); Juan Roberto Rodríguez Madoz, Pamplona (ES); Edurne San José Enériz, Pamplona (ES)

(73) Assignee: FUNDACIÓN PARA LA INVESTIGACIÓN MÉDICA APLICADA, Pamplona (ES)

( * ) Notice: Subject to any disclaimer, the term of this patent is extended or adjusted under 35 U.S.C. 154(b) by 0 days.

(21) Appl. No.: 15/315,326

(22) PCT Filed: Mar. 30, 2015

(86) PCT No.: PCT/EP2015/056860
§ 371 (c)(1),
(2) Date: Nov. 30, 2016

(87) PCT Pub. No.: WO2015/192981
PCT Pub. Date: Dec. 23, 2015

(65) Prior Publication Data
US 2017/0121316 A1    May 4, 2017

(30) Foreign Application Priority Data
Jun. 16, 2014   (EP) ................................... 14382230

(51) Int. Cl.
*C07D 405/14*    (2006.01)
*C07D 401/12*    (2006.01)

(52) U.S. Cl.
CPC ......... *C07D 405/14* (2013.01); *C07D 401/12* (2013.01)

(58) Field of Classification Search
CPC .................... C07D 405/14; C07D 401/12
See application file for complete search history.

(56) References Cited

U.S. PATENT DOCUMENTS

| 6,479,504 | B1 * | 11/2002 | Macfarlane | A61K 31/47 514/297 |
| 7,314,939 | B2 * | 1/2008 | Pandey | C07D 405/14 546/159 |
| 8,940,724 | B2 * | 1/2015 | Cushing | C07D 215/44 514/210.02 |
| 9,573,956 | B2 * | 2/2017 | Cuadrado Tejedor | C07D 401/14 |

FOREIGN PATENT DOCUMENTS

| EP | 1088818 A1 | 4/2001 |
| WO | WO 99/01154 A1 | 1/1999 |
| WO | WO 00/76982 A1 | 12/2000 |
| WO | WO 03/055866 A1 | 7/2003 |
| WO | WO 2004/056352 A1 | 7/2004 |
| WO | WO 2008/046085 A2 | 4/2008 |
| WO | WO 2009/049132 A1 | 4/2009 |
| WO | WO 2011/054433 A1 | 5/2011 |
| WO | WO 2013/062943 A1 | 5/2013 |
| WO | WO 2013/140148 A1 | 9/2013 |

(Continued)

OTHER PUBLICATIONS

Shankar, S.R., et al: "G9a, a multipotent regulator of gene expression", Jan. 2013, Epigenetics, vol. 8:1, pp. 16-22, 7 pages.
Vilas-Zornoza, A., et al: "Frequent and Simultaneous Epigenetic Inactivation of *TP53* Pathway Genes in Acute Lymphoblastic Leukemia", Feb. 2011, PLoS ONE, vol. 6, Issue 2, e17012, pp. 1- 14, 14 pages.
Rotili, D., et al: Properly Substituted Analogues of BIX-01294 Lose Inhibition of G9a Histone Methyltransferase and Gain Selective Anti-DNA Methyltransferase 3A Activity, May 2014, PLoS ONE, vol. 9, Issue 5, e96941, pp. 1-9, 9 pages.

(Continued)

*Primary Examiner* — Golam M M Shameem
(74) *Attorney, Agent, or Firm* — Squire Patton Boggs (US) LLP

(57) ABSTRACT

It relates to the use of compounds of formula (I'), or their pharmaceutically or veterinary acceptable salts, or their stereoisomers or mixtures thereof, as anticancer agents and as agents for generating induced pluripotent stem cells. Compounds of formula (I'), wherein $R_2'$ is an alcoxy group, a hydrocarbon chain or a ring system, and $R_1$, $R_3$, and $R_4$ are as defined herein, are dual inhibitors of histone methyltransferases and DNA methyltransferases. It also relates to the compounds of formula (I'), or their pharmaceutically or veterinary acceptable salts, or their stereoisomers or mixtures thereof, wherein $R_2'$ is phenyl or 5- to 6-membered heteroaromatic ring, both optionally fused to another rings (i.e., compounds of formula (I)). It also relates to pharmaceutical or veterinary compositions containing compounds of formula (I).

14 Claims, 1 Drawing Sheet

(56) References Cited

FOREIGN PATENT DOCUMENTS

WO   WO 2014/072371   5/2014

OTHER PUBLICATIONS

Vedadi, M., et al: "A chemical probe selectively inhibits G9a and GLP methyltransferase activity in cells", Aug. 2011, Nat. Chem. Biol., vol. 7, pp. 566-574, 10 pages.

Liu F., et al: "Discovery of an in Vivo Chemical probe of the Lysine Methyltransferases G9a and GLP", Oct. 2013, J. Med. Chem. 2013, vol. 56, pp. 8931-8942, 12 pages.

Jung, Da-Woon, et al: "Reprogram or Reboot: Small Molecule Approaches for the Production of Induced Pluripotent Stem Cells and Direct Cell Reprogramming", Nov. 2013, ACS Chem. Biol., vol. 9, pp. 80-95, 16 pages.

Shi, Y., et al: "Induction of Pluripotent Stem Cells from Mouse embryonic fibroblasts by Oct4 and Klf4 with small-molecule compounds", Nov. 2008, Cell Stem Cell, vol. 3, pp. 568-574, 7 pages.

Giardina, G., et al: "Discovery of a Novel Class of Selective Non-Peptide Antagonists for the Human Neurokinin-3 Receptor. 1. Identification of the 4-Quinolinecarboxamide Framework", May 1997, Journal of Medicinal Chemistry 1997, vol. 40, pp. 1794-1807, 14 pages.

Drake, N., et al: "Synthetic Antimalarials. The Preparation of Certain 4-Aminoquinolines", 1946, Journal of the American Chemical Society, vol. 68, pp. 1208-1213, 6 pages.

Tiscornia, G., et al: "Production and purification of lentiviral vectors", Jun. 2006, Nature Protocols, vol. 1, No. 1, pp. 241-245, 5 pages.

Takahashi, K., et al: "Induction of Pluripotent Stem Cells from Mouse Embryonic and Adult Fibroblast Cultures by Defined Factors", Aug. 2006, Cell, vol. 126, pp. 663-676, 14 pages.

Takahashi, K., et al: "Induction of Pluripotent Stem Cells from Adult Human Fibroblasts by Defined Factors", Nov. 2007, Cell, vol. 131, pp. 861-872, 12 pages.

Macfarlane, D. E., et al: "Antagonism of Immunostimulatory CpG-Oligodeoxynucleotides by Quinacrine, Chloroquine, and Structurally Related Compounds1", The Journal of Immunology 1998, pp. 1122-1131, 10 pages.

Notification of Transmittal of the International Search Report and the Written Opinion of the International Searching Authority, or the Declaration dated Jul. 14, 2015 for PCT/EP2015/056860, 18 pages.

\* cited by examiner

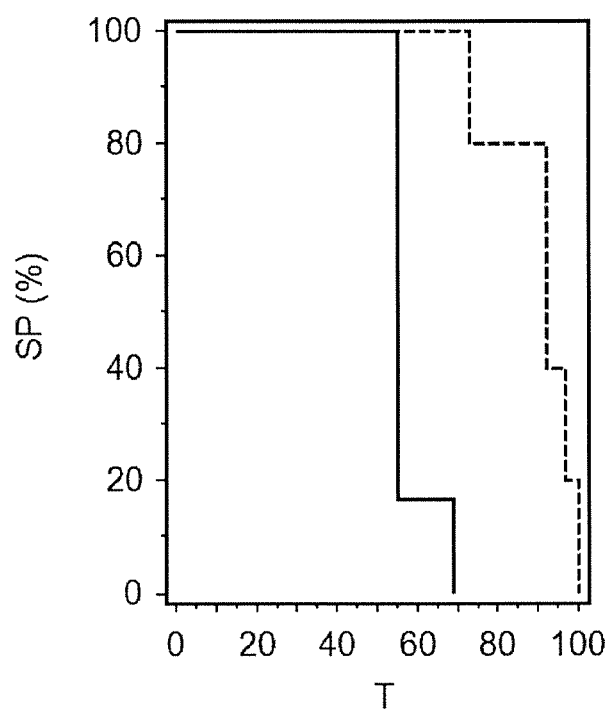

COMPOUNDS AS DUAL INHIBITORS OF HISTONE METHYLTRANSFERASES AND DNA METHYLTRANSFERASES

The present invention relates to 4-aminoquinoline derivatives, which are dual inhibitors of histone methyltransferases and DNA methyltransferases. It also relates to pharmaceutical or veterinary compositions containing them, and to their use in medicine, in particular as anticancer agents and as agents for generating induced pluripotent stem cells.

BACKGROUND ART

In recent years, it has been shown that cancer is a genetic and epigenetic disease, where epigenetic and genetic alterations interact reciprocally to drive cancer development. However, unlike genetic mutations, epigenetic changes are reversible, and as such, drugs that restore the epigenetic balance represent exciting potential therapeutic targets for cancer. Epigenetics refers to the heritable changes in gene expression patterns that occur independently of alterations in primary DNA sequence. The main epigenetic mechanisms are DNA methylation and covalent histone modifications, which play important roles in the regulation of transcription.

G9a, also known as EHMT2, is a histone methyltransferase that mono- and dimethylates Lysine 9 of histone H3 (H3K9me1 and H3K9me2, respectively).

G9a expression is high in many cancers compared with normal tissue. Cancer transcriptome analysis has revealed high expression in many tumors including hepatocellular, colon, prostate, lung and invasive transitional cell carcinomas and in B cell chronic lymphocytic leukemia. In a number of human bladder and lung carcinoma patients, G9a expression is upregulated (Shankar S R. et al., Epigenetics, 2013. 8(1): p. 16-22). Knockdown of G9a in both bladder and lung cancer cell lines caused growth suppression and apoptosis. Studies on prostate cancer further corroborate its role in carcinogenesis, where downregulation of G9a causes centrosome disruption, chromosomal instability, inhibition of cell growth and increased cellular senescence in cancer cells. In aggressive lung cancer, high levels of G9a correlate with poor prognosis with increased cell migration and invasion in vitro and metastasis in vivo. G9a is also overexpressed in pancreatic adenocarcinoma and inhibition of G9a induces cellular senescence in this type of cancer. In Acute Myeloid Leukemia mouse models, loss of G9a significantly delays disease progression and reduces leukemia stem cells frequency.

DNA methylation is an epigenetic modification that modulates gene expression without altering the DNA base sequence and plays a crucial role in cancer by silencing tumor suppressor genes. DNA methyltransferases (DNMTs) are the enzymes that catalyze DNA methylation. DNMT1 encodes the maintenance methyltransferase and DNMT3A and DNMT3B encode de novo methyltransferase.

DNMT1 and DNMT3A/3B are overexpressed in several types of cancer such as breast, gastric, pancreas, prostate, hepatocellular, ovarian, renal, retinoblastoma, glioma or diffuse large B-cell lymphoma. Zebularine, decitabine and azacytidine inhibits cell proliferation and induce apoptosis in acute lymphoblastic leukemia, acute myeloid leukemia, hepatic carcinoma, lung, breast, gastric or cervical cancer among others (Vilas-Zornoza A. et al., PLoS ONE, 2011. 6(2): p. e17012). Decitabine has been currently approved for myelodysplastic syndrome by the US Food and Drug Administration.

However, many efforts are made to develop new non-nucleoside inhibitors to overcome the limits of these aza-nucleosides, such as chemical instability and incorporation into DNA for activity.

A series of quinazoline derivatives have been described as potent selective G9a/GLP inhibitors, such as N-(1-benzyl-4-piperidyl)-6,7-dimethoxy-2-(4-methyl-1,4-diazepan-1-yl)quinazolin-4-amine (also known as BIX01294), 2-cyclohexyl-N-(1-isopropyl-4-piperidyl)-6-methoxy-7-(3-pyrrolidin-1-ylpropoxy)quinazolin-4-amine (also known as UNC0638), and 2-(4,4-difluoro-1-piperidyl)-N-(1-isopropyl-4-piperidyl)-6-methoxy-7-(3-pyrrolidin-1-ylpropoxy)quinazolin-4-amine (also known as UNC0642). However, these molecules display activity against DNMTs at high micromolar $IC_{50}$ values at most. Thus, for compound BIX01294 a 35±8% inhibition against DNMT1 and 12±3% inhibition against DNMT3A at 100 μM has been reported, which would correspond to $IC_{50}$ values>100 μM against DNMT1 and DNMT3A, respectively (Rotili D. et al., PLoS ONE, 2014. 9(5): p. E96941). For compound UNC0638 an $IC_{50}$ value of 107±6 μM against DNMT1 has been reported (Vedadi M. et al., Nat. Chem. Biol. 2011, 7, pp. 566-574), whereas for compound UNC0642, an in vitro $IC_{50}$ value>50 μM against DNMT1 has been described (Liu F. et al., J. Med. Chem. 2013, 56(21), pp. 8931-42).

Cellular reprogramming is a process that includes the induction of pluripotency in differentiated cells, generating induced pluripotent stem cells (iPSC), and the direct conversion of those differentiated cells to a non-related cell type, process called direct reprogramming. The generation of iPSC produces cells with similar but not identical properties to natural pluripotent stem cells, ie, embryonic stem cells (ESC). In general iPSC have been described to be similar to ESC in morphology, proliferation, teratoma formation and differentiation efficiency, but remarkable epigenetic and gene expression differences have been also observed. However, generation of iPSC may relay some knowledge about innate genetic aspects that occur during natural embryonic development.

Since their discovery, it was clear that cellular reprogramming, and especially iPSC generation, were destined to revolutionize the field of medicine. The power to create patient-specific pluripotent cells promised to provide invaluable models of human disease for in vitro research and offered the prospect of autologous, rejection-proof cell transplantation therapies and new regenerative medicine approaches Reprogramming methods that utilize viral vectors were however judged too risky to be used in clinical therapies. Thus, most efforts on the field have been focused on development of different approaches to generate good quality and safer transgene-free or integration-free iPS cells. This is an area of research where chemical biology has made a significant contribution to facilitate the efficient production of high quality iPSCs and elucidate the biological mechanisms governing their phenotype. In particular the development of various small molecules (Jung D W., et al. ACS Chem. Biol, 2014. 9(1): p. 80-95) has achieved a pivotal role in optimizing protocols for iPSC production identifying small-molecule combinations that were able to drive the reprogramming of mouse somatic cells toward pluripotent cells.

Moreover, it has been described that some epigenetic marks, like DNA and H3K9 methylation, may have an important role in cell reprogramming.

The reprogramming efficiency of BIX01294 obtained by Oct-4 and Klf-4 overexpression in mouse embryonic fibroblasts has been reported in Shi Y. et al., Cell Stem Cell 2008, 3, pp. 568-574. Besides, this paper also discloses that (2S)-2-(1,3-dioxoisoindolin-2-yl)-3-(1H-indol-3-yl)propanoic acid (also known as RG108), a DNMT inhibitor, enhanced the reprogramming activity in the presence of BIX01294.

There is still a need of developing compounds which show improved activity in the treatment and/or prevention of cancer and in the generation of induced pluripotent stem cells.

SUMMARY OF THE INVENTION

Inventors have found new compounds having a 4-aminoquinoline core which are capable to inhibit both the histone methyltransferase G9a and one or more DNA methyltransferases (DNMTs, including DNMT1, DNMT3A and/or DNMT3B) as demonstrated by the examples of the invention. These compounds are therefore dual inhibitors of G9a and DNMTs and could be useful for the treatment and/or prevention of cancer, as well as for the generation of induced pluripotent stem cells (iPSC).

Regarding their use in cancer, the compounds of the invention have the advantage that they are addressed to two different targets of those that, in in vitro tests, cell-based assays or in animal models, have proved useful for the treatment of cancer. The fact that the compounds of the present invention have an impact on two pathophysiological events, may lead to a more efficacious treatment.

Besides, the dual inhibition of G9a/DNMTs of the compounds of the invention has also an impact in the reprogramming of cells, in particular fibroblasts, as demonstrated by the examples and avoids the use of two different compounds one G9a inhibitor, and a DNMT inhibitor for improving the reprogramming activity as described in the literature. A first aspect of the invention relates to a compound of formula (I), or a pharmaceutically or veterinary acceptable salt thereof, or any stereoisomer or mixtures thereof, either of the compound of formula (I) or of any of its pharmaceutically or veterinary acceptable salts

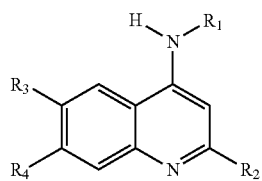

(I)

wherein:

$R_1$ is $R^a$;

$R_2$ is a known ring system selected from the group consisting of:
(i) phenyl;
(ii) 5- to 6-membered heteroaromatic ring;
(iii) phenyl fused to a 3- to 7-membered saturated or partially unsaturated or aromatic carbocyclic or heterocyclic monocyclic ring;
(iv) 5- to 6-membered heteroaromatic ring fused to a 3- to 7-membered saturated or partially unsaturated or aromatic carbocyclic or heterocyclic monocyclic ring;
(v) phenyl fused to a 6- to 14-membered saturated or partially unsaturated carbocyclic or heterocyclic bicyclic ring, wherein the rings of the bicyclic ring are spiro-fused; and
(vi) 5- to 6-membered heteroaromatic ring fused to a 6- to 14-membered saturated or partially unsaturated carbocyclic or heterocyclic bicyclic ring, wherein the rings of the bicyclic ring are spiro-fused;

wherein $R_2$ is optionally substituted with:
a) one $Cy^1$ or one $Cy^2$, and/or
b) one or more substituents $R^b$, and/or
c) one or more substituents $Z^1$ optionally substituted with one or more substituents $R^b$ and/or one $Cy^1$;
wherein $Cy^1$ or $Cy^2$ are optionally substituted with one or more substituents independently selected from $R^b$, and $Z^2$ optionally substituted with one or more substituents $R^b$;

$R_3$ is selected from H, $R^c$, halogen, —$NO_2$, —CN, —$OR^{c'}$, —$OC(O)R^{c'}$, —$OC(O)OR^{c'}$, —$OC(O)NR^{c'}R^{c'}$, —$NR^{c'}R^{c'}$, —$NR^{c'}C(O)R^{c'}$, —$NR^{c'}C(O)OR^{c'}$, —$NR^{c'}C(O)NR^{c'}R^{c'}$, —$NR^{c'}S(O)_2R^{c'}$, —$NR^{c'}SO_2NR^{c'}R^{c'}$, —$SR^{c'}$, —$S(O)R^{c'}$, —$S(O)OR^{c'}$, —$SO_2R^{c'}$, —$SO_2(OR^{c'})$, —$SO_2NR^{c'}R^{c'}$, —$SC(O)NR^{c'}R^{c'}$, —$C(O)R^{c'}$, —$C(O)OR^{c'}$, —$C(O)NR^{c'}R^{c'}$, and —$C(O)NR^{c'}OR^{c'}$, and —$C(O)NR^{c'}SO_2R^{c'}$;

$R_4$ is selected from —$OR^a$ and —$NR^aR^{c'}$;

each $R^a$ is independently $Cy^2$, or $Z^3$ optionally substituted with one or more substituents $R^b$ and/or one $Cy^3$;

wherein $Cy^2$ is optionally substituted with:
a) one $Cy^4$; and/or
b) one or more substituents $R^b$, and/or
c) one or more substituents $Z^4$ optionally substituted with one or more substituents $R^b$ and/or one $Cy^4$;
wherein $Cy^4$ is optionally substituted with one or more substituents independently selected from $R^b$, and $Z^5$ optionally substituted with one or more substituents $R^b$; and wherein $Cy^3$ is optionally substituted with:
a) one $Cy^5$; and/or
b) one or more substituents $R^b$, and/or
c) one or more substituents $Z^6$ optionally substituted with one or more substituents $R^b$ and/or one $Cy^5$;
wherein $Cy^5$ is optionally substituted with one or more substituents independently selected from $R^b$, and $Z^7$ optionally substituted with one or more substituents $R^b$;

each $R^b$ is independently selected from halogen, —$NO_2$, —CN, —$OR^{c'}$, —$OC(Y)R^{c'}$, —$OC(Y)OR^{c'}$, —$OC(Y)NR^{c'}R^{c'}$, —$NR^{c'}R^{c'}$, —$NR^{c'}C(Y)R^{c'}$, —$NR^{c'}C(Y)OR^{c'}$, —$NR^{c'}C(Y)NR^{c'}R^{c'}$, —$NR^{c'}S(O)_2R^{c'}$, —$NR^{c'}SO_2NR^{c'}R^{c'}$, —$SR^{c'}$, —$S(O)R^{c'}$, —$S(O)OR^{c'}$, —$SO_2R^{c'}$, —$SO_2(OR^{c'})$, —$SO_2NR^{c'}R^{c'}$, —$SC(Y)NR^{c'}R^{c'}$, —$C(Y)R^{c'}$, —$C(Y)OR^{c'}$—$C(Y)NR^{c'}R^{c'}$, —$C(Y)NR^{c'}OR^{c'}$, and —$C(O)NR^{c'}SO_2R^{c'}$;

each $R^{c'}$ is independently H or $R^c$;

each $R^c$ is independently selected from the group consisting of ($C_1$-$C_6$)alkyl, ($C_2$-$C_6$)alkenyl, ($C_2$-$C_6$)alkynyl, ($C_2$-$C_6$) hydrocarbon chain having one or more double bonds and one or more triple bonds, and 3- to 7-membered saturated or partially unsaturated or aromatic carbocyclic or heterocyclic monocyclic ring, wherein each $R^c$ is optionally substituted with one or more halogen atoms, Y is O, S, or $NR^{c'}$;

$Z^1, Z^2, Z^3, Z^4, Z^5, Z^6$ and $Z^7$ are independently selected from the group consisting of ($C_1$-$C_{12}$)alkyl, ($C_2$-$C_{12}$)alkenyl, ($C_2$-$C_{12}$)alkynyl, and ($C_2$-$C_6$)hydrocarbon chain having one or more double bonds and one or more triple bonds;

$Cy^1, Cy^4$ and $Cy^5$ are independently a known ring system selected from the group consisting of phenyl; 3- to 7-membered carbocyclic or heterocyclic monocyclic ring, saturated or partially unsaturated; and 5- or 6-membered heteroaromatic ring;

Cy² and Cy³ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N(C₁-C₄)alkyl];

with the proviso that the compound of formula (I) is other than:

2-[(7-methoxy-2-phenyl-4-quinolyl)amino]ethanol;
2-[(7-methoxy-2-phenyl-4-quinolyl)amino]ethanol hydrochloride salt;
2-(2-chlorophenyl)-6,7-dimethoxy-N-(4-pyridyl)quinolin-4-amine;
1-[[2-(4-chlorophenyl)-7-methoxy-4-quinolyl]amino]-3-(methylamino)propan-2-ol;
1-[[2-(4-chlorophenyl)-7-methoxy-4-quinolyl]amino]-3-(methylamino)propan-2-ol hydrochloride salt;
2-[[2-(4-chlorophenyl)-7-methoxy-4-quinolyl]amino]ethanol;
2-[[2-(4-chlorophenyl)-7-methoxy-4-quinolyl]amino]ethanol hydrochloride salt;
1-amino-3-[(7-methoxy-2-phenyl-4-quinolyl)amino]propan-2-ol;
1-amino-3-[(7-methoxy-2-phenyl-4-quinolyl)amino]propan-2-ol hydrochloride salt;
2-[[2-(3,4-dichlorophenyl)-7-methoxy-4-quinolyl]amino]ethanol;
2-[[2-(3,4-dichlorophenyl)-7-methoxy-4-quinolyl]amino]ethanol hydrochloride salt;
(2S)-1-[(7-methoxy-2-phenyl-4-quinolyl)amino]propan-2-ol;
(2S)-1-[(7-methoxy-2-phenyl-4-quinolyl)amino]propan-2-ol hydrochloride salt;
1-[[7-methoxy-2-(p-tolyl)-4-quinolyl]amino]-3-(methylamino)propan-2-ol;
1-[[7-methoxy-2-(p-tolyl)-4-quinolyl]amino]-3-(methylamino)propan-2-ol hydrochloride salt;
1-amino-3-[[2-(3,4-dichlorophenyl)-7-methoxy-4-quinolyl]amino]propan-2-ol;
1-amino-3-[[2-(3,4-dichlorophenyl)-7-methoxy-4-quinolyl]amino]propan-2-ol hydrochloride salt;
2-[[7-methoxy-2-(p-tolyl)-4-quinolyl]amino]ethanol;
2-[[7-methoxy-2-(p-tolyl)-4-quinolyl]amino]ethanol hydrochloride salt;
3-[(7-methoxy-2-phenyl-4-quinolyl)amino]propane-1;2-diol;
3-[(7-methoxy-2-phenyl-4-quinolyl)amino]propane-1;2-diol hydrochloride salt;
1-amino-3-[[2-(4-chlorophenyl)-7-methoxy-4-quinolyl]amino]propan-2-ol;
1-amino-3-[[2-(4-chlorophenyl)-7-methoxy-4-quinolyl]amino]propan-2-ol hydrochloride salt;
1-amino-3-[[7-methoxy-2-(p-tolyl)-4-quinolyl]amino]propan-2-ol;
1-amino-3-[[7-methoxy-2-(p-tolyl)-4-quinolyl]amino]propan-2-ol hydrochloride salt;
1-amino-3-[[7-methoxy-2-(4-methoxyphenyl)-4-quinolyl]amino]propan-2-ol;
1-amino-3-[[7-methoxy-2-(4-methoxyphenyl)-4-quinolyl]amino]propan-2-ol hydrochloride salt;
2-[[7-methoxy-2-(4-methoxyphenyl)-4-quinolyl]amino]ethanol;
2-[[7-methoxy-2-(4-methoxyphenyl)-4-quinolyl]amino]ethanol hydrochloride salt;
5-[[[2-(4-chlorophenyl)-7-methoxy-4-quinolyl]amino]methyl]oxazolidin-2-one;
5-[[[7-methoxy-2-(p-tolyl)-4-quinolyl]amino]methyl]oxazolidin-2-one;
Benzyl-N-(7-methoxy-2-phenyl-4-quinolyl)carbamate
N-benzyl-7-methoxy-2-phenyl-quinolin-4-amine;
N¹,N¹-diethyl-N⁴-(7-methoxy-2-phenyl-4-quinolyl)pentane-1,4-diamine;
N¹,N¹-diethyl-N⁴-(7-methoxy-2-phenyl-4-quinolyl)pentane-1,4-diamine triphosphate salt; and
2-(4-fluorophenyl)-N⁷-[(3-methoxyphenyl)methyl]-N₄-(4-pyridyl)quinoline-4,7-diamine.

A second aspect of the invention relates to a pharmaceutical or veterinary composition which comprises an effective amount of a compound of formula (I) as defined above, or a pharmaceutically or veterinary acceptable salt thereof, or any stereoisomer either of the compound of formula (I) or of its pharmaceutically or veterinary acceptable salt, together with one or more pharmaceutically or veterinary acceptable excipients or carriers.

A third aspect of the invention relates to a compound of formula (I'), or a pharmaceutically or veterinary acceptable salt thereof, or any stereoisomer or mixtures thereof, either of the compound of formula (I') or of any of its pharmaceutically or veterinary acceptable salts

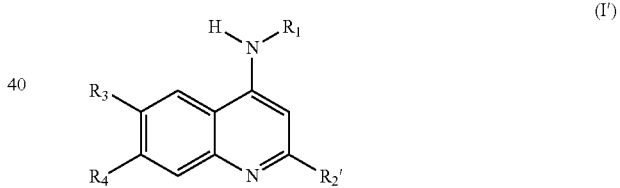

for use in the treatment and/or prevention of cancer mediated by the inhibition of histone methyltransferase G9a and of one or more DNMTs selected from the group consisting of DNMT1, DNMT3A and DNMT3B, wherein:

$R_1$ is $R^a$;

$R_2'$ is selected from the group consisting of —$OZ^8$, $Cy^6$, and $Z^8$; wherein each $Z^8$ is optionally substituted with one or more substituents $R^b$ and/or one $Cy^7$;

wherein $Cy^6$ is optionally substituted with:
  a) one $Cy^1$ or one $Cy^2$, and/or
  b) one or more substituents $R^b$, and/or
  c) one or more substituents $Z^1$ optionally substituted with one or more substituents $R^b$ and/or one $Cy^1$;
    wherein $Cy^1$ or $Cy^2$ are optionally substituted with one or more substituents independently selected from $R^b$, and $Z^2$ optionally substituted with one or more substituents $R^b$;

wherein $Cy^7$ is optionally substituted with:
  a) one $Cy^8$; and/or
  b) one or more substituents $R^b$, and/or
  c) one or more substituents $Z^9$ optionally substituted with one or more substituents $R^b$ and/or one $Cy^8$;

wherein Cy$^8$ is optionally substituted with one or more substituents independently selected from R$^b$, and Z$^{10}$ optionally substituted with one or more substituents R$^b$;

R$_3$ is selected from H, R$^c$, halogen, —NO$_2$, —CN, —OR$^{c'}$, —OC(O)R$^{c'}$, —OC(O)OR$^{c'}$, —OC(O)NR$^{c'}$R$^{c'}$, —NR$^{c'}$R$^{c'}$, —NR$^{c'}$C(O)R$^{c'}$, —NR$^{c'}$C(O)OR$^{c'}$, —NR$^{c'}$C(O)NR$^{c'}$R$^{c'}$, —NR$^{c'}$S(O)$_2$R$^{c'}$, —NR$^{c'}$SO$_2$NR$^{c'}$R$^{c'}$, —SR$^{c'}$, —S(O)R$^{c'}$, —S(O)OR$^{c'}$, —SO$_2$R$^{c'}$, —SO$_2$(OR$^{c'}$), —SO$_2$NR$^{c'}$R$^{c'}$, —SC(O)NR$^{c'}$R$^{c'}$, —C(O)R$^{c'}$, —C(O)OR$^{c'}$, —C(O)NR$^{c'}$R$^{c'}$, and —C(O)NR$^{c'}$OR$^{c'}$, and —C(O)NR$^{c'}$SO$_2$R$^{c'}$;

R$_4$ is selected from —OR$^a$ and —NR$^a$R$^c$;

each R$^a$ is independently Cy$^2$, or Z$^3$ optionally substituted with one or more substituents R$^b$ and/or one Cy$^3$;

wherein Cy$^2$ is optionally substituted with:
  a) one Cy$^4$; and/or
  b) one or more substituents R$^b$, and/or
  c) one or more substituents Z$^4$ optionally substituted with one or more substituents R$^b$ and/or one Cy$^4$;
    wherein Cy$^4$ is optionally substituted with one or more substituents independently selected from R$^b$, and Z$^5$ optionally substituted with one or more substituents R$^b$; and wherein Cy$^3$ is optionally substituted with:
  a) one Cy$^5$; and/or
  b) one or more substituents R$^b$, and/or
  c) one or more substituents Z$^6$ optionally substituted with one or more substituents R$^b$ and/or one Cy$^5$;
    wherein Cy$^5$ is optionally substituted with one or more substituents independently selected from R$^b$, and Z$^7$ optionally substituted with one or more substituents R$^b$;

each R$^b$ is independently selected from halogen, —NO$_2$, —CN, —OR$^{c'}$, —OC(Y)R$^{c'}$, —OC(Y)OR$^{c'}$, —OC(Y)NR$^{c'}$R$^{c'}$, —NR$^{c'}$R$^{c'}$, —NR$^{c'}$C(Y)R$^{c'}$, —NR$^{c'}$C(Y)OR$^{c'}$—NR$^{c'}$C(Y)NR$^{c'}$R$^{c'}$, —NR$^{c'}$S(O)$_2$R$^{c'}$, —NR$^{c'}$SO$_2$NR$^{c'}$R$^{c'}$, —SR$^{c'}$, —S(O)R$^{c'}$, —S(O)OR$^{c'}$, —SO$_2$R$^{c'}$, —SO$_2$(OR$^{c'}$), —SO$_2$NR$^{c'}$R$^{c'}$, —SC(Y)NR$^{c'}$R$^{c'}$, —C(Y)R$^{c'}$, —C(Y)OR$^{c'}$—C(Y)NR$^{c'}$R$^{c'}$, —C(Y)NR$^{c'}$OR$^{c'}$, and —C(O)NR$^{c'}$SO$_2$R$^{c'}$;

each R$^{c'}$ is independently H or R$^c$;

each R$^c$ is independently selected from the group consisting of (C$_1$-C$_6$)alkyl, (C$_2$-C$_6$)alkenyl, (C$_2$-C$_6$)alkynyl, (C$_2$-C$_6$) hydrocarbon chain having one or more double bonds and one or more triple bonds, and 3- to 7-membered saturated or partially unsaturated or aromatic carbocyclic or heterocyclic monocyclic ring, wherein each R$^c$ is optionally substituted with one or more halogen atoms, Y is O, S, or NR$^{c'}$;

Z$^1$, Z$^2$, Z$^3$, Z$^4$, Z$^5$, Z$^6$, Z$^7$, Z$^8$, Z$^9$ and Z$^{10}$ are independently selected from the group consisting of (C$_1$-C$_{12}$)alkyl, (C$_2$-C$_{12}$)alkenyl, (C$_2$-C$_{12}$)alkynyl, and (C$_2$-C$_6$)hydrocarbon chain having one or more double bonds and one or more triple bonds;

Cy$^1$, Cy$^4$, Cy$^5$ and Cy$^8$ are independently a known ring system selected from the group consisting of phenyl; 3- to 7-membered carbocyclic or heterocyclic monocyclic ring, saturated or partially unsaturated; and 5- or 6-membered heteroaromatic ring;

mCy$^2$, Cy$^3$ and Cy$^7$ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;

Cy$^6$ is a known ring system selected from group consisting of:
  (i) phenyl;
  (ii) 5- or 6-membered heteroaromatic ring;
  (iii) 3- to 7-membered carbocyclic or heterocyclic monocyclic ring, which is saturated or partially unsaturated;
  (iv) 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;
  (v) phenyl fused to a 6- to 14-membered saturated or partially unsaturated carbocyclic or heterocyclic bicyclic ring, wherein the rings of the bicyclic ring are spiro-fused; and
  (vi) 5- to 6-membered heteroaromatic ring fused to a 6- to 14-membered saturated or partially unsaturated carbocyclic or heterocyclic bicyclic ring, wherein the rings of the bicyclic ring are spiro-fused;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N(C$_1$-C$_4$)alkyl].

Thus, the third aspect of the invention relates to the use of a compound of formula (I') as defined above, for the manufacture of a medicament for the treatment and/or prevention of cancer; and may also be formulated as a method for the treatment and/or prevention of cancer, comprising administering an effective amount of the previously defined compound of formula (I'), or a pharmaceutically or veterinary acceptable salt thereof, or any stereoisomer or mixtures thereof, either of the compound of formula (I') or of any of its pharmaceutically or veterinary acceptable salts, and one or more pharmaceutically or veterinary acceptable excipients or carriers, in a subject in need thereof, including a human.

A fourth aspect of the invention relates to a method for generating an induced pluripotent stem cell, the method comprising the step of culturing an isolated cell together with one or more transcription factors and a compound of formula (I'), or a pharmaceutically or veterinary acceptable salt thereof, or any stereoisomer or mixtures thereof, either of the compound of formula (I') or of any of its pharmaceutically or veterinary acceptable salts, wherein the compound of formula (I') is as defined above.

BRIEF DESCRIPTION OF THE DRAWINGS

FIG. 1 represents the survival curve in mice treated with compound 3-04 (dashed line) and in control groups (solid line) in a human B-ALL mice model. Y-axis corresponds to the survival probability (SP) %. X-axis corresponds to the days (T: time) after tumor cells inoculation.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "carbocyclic" ring system refers to a known ring system wherein all the ring members contain carbon atoms. The term "heterocyclic" ring system refers to a known ring system wherein one or more of the ring members, preferably 1, 2, 3, or 4 ring members, are selected from NH, N, O, and S, where chemically possible. The remaining ring members of the heterocyclic ring are independently selected from C, CH, $CH_2$, O, N, NH, and S. Unless otherwise specified, the "heterocyclic" ring system may be attached to the rest of the molecule through a C or a N atom of the ring system. Both the carbocyclic and heterocyclic rings can be saturated or partially unsaturated, and may be unsubstituted or substituted as described herein, being the substituents placed on any available position.

For the purposes of the present invention, in "fused" rings the fusion occurs through one bond which is common to two adjoining rings; in "bridged-fused" rings the fusion occurs through a sequence of atoms (bridgehead) which is common to two rings; and in "spiro-fused" rings, the fusion occurs through only one atom (spiro atom), preferably a carbon atom, which is common to two adjoining rings (including bridged rings).

The term "heteroaromatic" ring refers to a known aromatic ring system, wherein one or more of the ring members, preferably 1, 2, 3, or 4 ring members, are selected from NH, N, O, and S, where chemically possible. The remaining ring members of the heteroaromatic ring are independently selected from C, CH, O, N, NH, and S. The heteroaromatic ring may be unsubstituted or substituted as described herein, being the substituents placed on any available position.

The present invention also includes the tautomeric forms of the compounds of formula (I) or (I'). The term "tautomeric isomers" means isomers, the structures of which differ in the position of an atom, generally a hydrogen atom, and of one or more multiple bonds, and which are capable of easily and reversibly changing from one to another. The tautomers are used indistinctly in the present application. Thus, as an example, a hydroxyphenyl group has to be considered equivalent to its tautomeric form: cyclohexa-2,4-dienone.

The term "known ring system" as used herein refers to a ring system which is chemically feasible and is known in the art and so intends to exclude those ring systems that are not chemically possible.

For the purposes of the present invention, in all saturated or partially unsaturated rings, one or two members of the rings are optionally C(O) and/or C(NH) and/or $C[N(C_1-C_4)$alkyl].

The term $(C_1-C_n)$alkyl refers to a saturated branched or linear hydrocarbon chain which contains from 1 to n carbon atoms and only single bonds. The term $(C_2-C_n)$alkenyl refers to an unsaturated branched or linear hydrocarbon chain which comprises from 2 to n carbon atoms and at least one or more double bonds. The term $(C_2-C_n)$alkynyl refers to a saturated branched or linear hydrocarbon chain which comprises from 2 to n carbon atoms and at least one or more triple bonds. For the purposes of the invention, the $(C_2-C_n)$ hydrocarbon chain having one or more double bonds and one or more triple bonds is a branched or linear hydrocarbon chain which contains from 2 to n carbon atoms. Moreover, in any of the hydrocarbon chains defined above, one or two chain members selected from $CH_2$ or CH may be optionally replaced by chain members independently selected from N, NR, O, C(O), C(O)NR, NRC(O) and S; wherein R is H or $(C_1-C_6)$alkyl optionally substituted with one or more halogen atoms.

A halogen substituent means fluoro, chloro, bromo or iodo.

In the embodiments of the invention referring to the compounds of formula (I) or formula (I'), where the substitution or unsubstitution of a certain group is not specified, e.g. either by indicating a certain substitution for that group or by indicating that the group is unsubstituted, it has to be understood that the possible substitution of this group is the one as in the definition of the formula (I) or formula (I'). Further, the expression "substituted as defined herein", "substituted as previously defined" or any equivalent expression has to be understood that the possible substitution of this group is the one as in the definition of the formula (I) or formula (I').

"Protective group" (PG) refers to a grouping of atoms that when attached to a reactive group in a molecule masks, reduces or prevents that reactivity.

The expression "substituted with one or more" means that a group can be substituted with one or more, preferably with 1, 2, 3 or 4 substituents, provided that this group has enough positions susceptible of being substituted.

For the purposes of the invention, room temperature is 20-25° C.

In the first aspect of the invention related to the compounds of formula (I), as well as in some of the embodiments related to compounds of formula (I'), the compound of the invention is other than the ones listed in table 1:

TABLE 1

| Compd. Number | Compound name (CAS Registry Number) | Chemical formula | Bibliographic references |
|---|---|---|---|
| 1 | 2-[(7-methoxy-2-phenyl-4-quinolyl)amino]ethanol (1350414-85-5) and its hydrochloride salt (1350053-59-6) | | No references |

TABLE 1-continued

| Compd. Number | Compound name (CAS Registry Number) | Chemical formula | Bibliographic references |
|---|---|---|---|
| 2 | 2-(2-chlorophenyl)-6,7-dimethoxy-N-(4-pyridyl)quinolin-4-amine (1349414-19-2) | | No references |
| 3 | 1-[[2-(4-chlorophenyl)-7-methoxy-4-quinolyl]amino]-3-(methylamino)propan-2-ol (781604-61-3) and its hydrochloride salt (332181-22-3) | | Example 79 of EP 1088818 A1 (as hydrochloride salt: 332181-22-3) |
| 4 | 2-[[2-(4-chlorophenyl)-7-methoxy-4-quinolyl]-amino]ethanol (774528-48-2) and its hydrochloride salt (332180-80-0) | | Example 37 of EP 1088818 A1 (as hydrochloride salt: 332180-80-0) |
| 5 | 1-amino-3-[(7-methoxy-2-phenyl-4-quinolyl)-amino]propan-2-ol (773045-20-8) and its hydrochloride salt (332180-70-8) | | Example 29 of EP 1088818 A1 (as hydrochloride salt: 332180-70-8) |

TABLE 1-continued

| Compd. Number | Compound name (CAS Registry Number) | Chemical formula | Bibliographic references |
|---|---|---|---|
| 6 | 2-[[2-(3,4-dichlorophenyl)-7-methoxy-4-quinolyl]-amino]etanol (765889-92-7) and its hydrochloride salt (332180-84-4) | | Example 41 of EP 1088818 A1 (as hydrochloride salt: 332180-84-4) |
| 7 | (2S)-1-[(7-methoxy-2-phenyl-4-quinolyl)-amino]propan-2-ol (763073-54-7) and its hydrochloride salt (332180-74-2) | | Example 33 of EP 1088818 A1 (as hydrochloride salt: 332180-74-2) |
| 8 | 1-[[7-methoxy-2-(p-tolyl)-4-quinolyl]amino]-3-(methylamino)propan-2-ol (762230-60-4) and its hydrochloride salt (332181-21-2) | | Example 78 of EP 1088818 A1 (as hydrochloride salt: 332181-21-2) |
| 9 | 1-amino-3-[[2-(3,4-dichlorophenyl)-7-methoxy-4-quinolyl]-amino]propan-2-ol (755743-60-3) and its hydrochloride salt (332180-85-5) | | Example 42 of EP 1088818 A1 (as hydrochloride salt: 332180-85-5) |

TABLE 1-continued

| Compd. Number | Compound name (CAS Registry Number) | Chemical formula | Bibliographic references |
|---|---|---|---|
| 10 | 2-[[7-methoxy-2-(p-tolyl)-4-quinolyl]amino]etanol (733730-71-7) and its as hydrochloride salt (332180-65-1) | | Example 24 of EP 1088818 A1 (as hydrochloride salt: 332180-65-1) |
| 11 | 3-[(7-methoxy-2-phenyl-4-quinolyl)amino]-propane-1,2-diol (725683-84-1) and its hydrochloride salt (332180-77-5) | | Example 35 of EP 1088818 A1 (as hydrochloride salt: 332180-77-5) |
| 12 | 1-amino-3-[[2-(4-chloro-phenyl)-7-methoxy-4-quinolyl]amino]propan-2-ol (332182-30-6) and its hydrochloride salt (332180-64-0) | | Example 23 of EP 1088818 A1 (as hydrochloride salt: 332180-64-0) |
| 13 | 1-amino-3-[[7-methoxy-2-(p-tolyl)-4-quinolyl]-amino]propan-2-ol (332182-07-7) and its hydrochloride salt (332180-53-7) | | Example 13 of EP 1088818 A1 (as hydrochloride salt: 332180-53-7) |

TABLE 1-continued

| Compd. Number | Compound name (CAS Registry Number) | Chemical formula | Bibliographic references |
|---|---|---|---|
| 14 | 1-amino-3-[[7-methoxy-2-(4-methoxyphenyl)-4-quinolyl]amino]propan-2-ol (332182-06-6) and its hydrochloride salt (332180-52-6) | | Example 12 of EP 1088818 A1 (as hydrochloride salt: 332180-52-6) |
| 15 | 2-[[7-methoxy-2-(4-methoxyphenyl)-4-quinolyl]amino]ethanol (332182-05-5) and its hydrochloride salt (332180-51-5) | | Example 11 of EP 1088818 A1 (as hydrochloride salt: 332180-51-5) |
| 16 | 5-[[[2-(4-chlorophenyl)-7-methoxy-4-quinolyl]-amino]methyl]oxazolidin-2-one (332181-49-4) | | Example 106 of EP 1088818 A1 |
| 17 | 5-[[[7-methoxy-2-(p-tolyl)-4-quinolyl]amino]methyl]ox-azolidin-2-one (332181-48-3) | | Example 105 of EP 1088818 A1 |

TABLE 1-continued

| Compd. Number | Compound name (CAS Registry Number) | Chemical formula | Bibliographic references |
|---|---|---|---|
| 18 | Benzyl-N-(7-methoxy-2-phenyl-4-quinolyl)-carbamate (189815-96-1) | | Compound 37 of Giardina G. et al., Journal of Medicinal Chemistry 1997, 40(12), 1794-1807 |
| 19 | N-benzyl-7-methoxy-2-phenyl-quinolin-4-amine (189815-95-0) | | Compound 4 of Giardina G. et al., Journal of Medicinal Chemistry 1997, 40(12), 1794-1807 |
| 20 | $N^1,N^1$-diethyl-$N^4$-(7-methoxy-2-phenyl-4-quinolyl)pentane-1,4-diamine (47632-17-7) and its triphosphate salt (5431-09-4) | | Product No. 21 of Drake N. et al., Journal of the American Chemical Society 1946, 68, 1208-13. |
| 21 | 2-(4-fluorophenyl)-$N^7$-[(3-methoxyphenyl)methyl]-$N^4$-(4-pyridyl)quinoline-4,7-diamine (1347903-33-6) | | No references |

As can be seen in the table above the cited compounds are either commercial products with no associated bibliographic references or are disclosed in the references EP1088818 A1 (NMDA(N-methyl-D-aspartate)-receptor subtype selective blockers); Giardina G. et al., "*Discovery of a Novel Class of Selective Non-Peptide Antagonists for the Human Neurokinin-3 Receptor 1. Identification of the 4-Quinolinecarboxamide Framework*", Journal of Medicinal Chemistry 1997, 40(12), 1794-1807; and Drake N. et al., "*Synthetic Antimalarials. The Preparation of Certain 4-Aminoquinolines*", Journal of the American Chemical Society 1946, 68, 1208-13. None of these documents describes the ability of these compounds to inhibit both the histone methyltransferase G9a and the DNA methyltransferases (DNMT1,DNMT3A or DNMT3B), nor their use in the treatment and/or prevention of cancer, or in the generation of induced pluripotent stem cells.

There is no limitation on the type of salt of the compounds of the invention that can be used, provided that these are pharmaceutically or veterinary acceptable when they are used for therapeutic purposes. The term "pharmaceutically or veterinary acceptable salts", embraces salts commonly used to form alkali metal salts and to form addition salts of free acids or free bases.

The preparation of pharmaceutically or veterinary acceptable salts of the compounds of formula (I) or of formula (I') can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically or veterinary acceptable base or acid in water or in an organic solvent or in a mixture of them. The compounds of formula (I) of formula (I') and their salts may differ in some physical properties but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically or veterinary acceptable solvents such as water, ethanol and the like are equivalent to the unsolvated form for the purposes of the invention.

Some compounds of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention relates to each of these stereoisomers and also mixtures thereof.

Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

In all embodiments of the invention referring to the compounds of formula (I) or formula (I'), the pharmaceutically acceptable salts thereof and the stereoisomers either of any of the compounds of formula (I) or formula (I') or of any of their pharmaceutically acceptable salts are always contemplated even if they are not specifically mentioned.

In another embodiment, optionally in combination with one or more features of the various embodiments described above or below, the invention relates to a compound of formula (I) as previously described, wherein in $R_1$, $Cy^2$ and $Cy^3$ are independently a known ring system selected from a 3- to 7-membered carbocyclic or heterocyclic monocyclic ring, which is saturated or partially unsaturated; and a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring.

In one embodiment, optionally in combination with one or more features of the various embodiments described above or below, the invention relates to a compound of formula (I) as previously described, wherein $R_2$ is other than unsubstituted phenyl, 4-methylphenyl, 4-chlorophenyl, 2-chlorophenyl, 3,4-dichlorophenyl, 4-fluorophenyl and 4-methoxyphenyl.

In another embodiment, optionally in combination with one or more features of the various embodiments described above or below, the invention relates to a compound of formula (I) as previously described, wherein $R_3$ is selected from halogen, —CN and —$OR^{c'}$, more particularly, $R_3$ is selected from halogen and —$OR^{c'}$.

In another embodiment, optionally in combination with one or more features of the various embodiments described above or below, the invention relates to a compound of formula (I) as previously described, wherein $R_3$ is —$OR^{c'}$; more particularly, $R^{c'}$ is H or $R^c$; wherein $R^c$ is ($C_1$-$C_6$)alkyl optionally substituted with one or more halogen atoms.

In another embodiment, optionally in combination with one or more features of the various embodiments described above or below, the invention relates to a compound of formula (I) as previously described, wherein $R_4$ is $OR^a$. More particularly, $R^a$ in $R_4$ is $Z^3$ optionally substituted as previously defined.

In another embodiment, optionally in combination with one or more features of the various embodiments described above or below, the invention relates to a compound of formula (I) as previously described, wherein $R_4$ is $OR^a$ with the condition that $R^a$ contains at least one nitrogen atom.

In another embodiment, optionally in combination with one or more features of the various embodiments described above or below, the invention relates to a compound of formula (I) as previously described, wherein $R_4$ is $OCy^2$ or $OZ^3$ as previously defined, wherein $Cy^2$ is optionally substituted as previously defined and $Z^3$ is substituted with one or more substituents $R^b$ and/or one $Cy^3$, as previously defined. More particularly, $R_4$ is $OCy^2$ as previously defined or $R_4$ is $OZ^3$, wherein $Z^3$ is ($C_1$-$C_6$)alkyl substituted with one or more substituents $R^b$ and/or one $Cy^3$, as previously defined. Even more particularly, $R_4$ is $OCy^2$ as previously defined or $R_4$ is $OZ^3$, wherein $Z^3$ is ($C_1$-$C_6$)alkyl substituted with one or more substituents $R^b$ and/or one $Cy^3$, as previously defined with the condition that $Z^3$ contains at least one nitrogen atom.

In another embodiment, optionally in combination with one or more features of the various embodiments described above or below, the invention relates to a compound of formula (I) as previously described, wherein $R_2$ is a known ring system selected from the group consisting of:

(i) phenyl;
(ii) phenyl fused to a 3- to 7-membered saturated or partially unsaturated or aromatic carbocyclic or heterocyclic monocyclic ring;
(iii) 5- to 6-membered heteroaromatic ring; and
(iv) 5- to 6-membered heteroaromatic ring fused to a 3- to 7-membered saturated or partially unsaturated or aromatic carbocyclic or heterocyclic monocyclic ring;

wherein $R_2$ is optionally substituted as previously defined.

In another embodiment, optionally in combination with one or more features of the various embodiments described above or below, the invention relates to a compound of formula (I) as previously described, wherein $R_2$ is attached to the quinoline through a carbon atom.

In another embodiment, optionally in combination with one or more features of the various embodiments described above or below, the invention relates to a compound of formula (I) as previously described, wherein $R_2$ is phenyl or 5- to 6-membered heteroaromatic monocyclic ring, being both groups optionally substituted as previously defined. More particularly, $R_2$ is 5- to 6-membered heteroaromatic monocyclic ring optionally substituted as previously defined, even more particularly, $R_2$ is attached to the quinoline through a carbon atom, and even more particularly, $R_2$ is selected from the group consisting of 2-thiophene, 2-pyrrol, 3-pyrrol, 2-furan and 3-furan.

As mentioned above the invention also relates to a compound of formula (I'), or its salts, or its stereoisomers or mixtures, either of the compound of formula (I') or of its salts for use in the treatment and/or prevention of cancer mediated by the inhibition of histone methyltransferase G9a and of one or more DNMTs selected from the group consisting of DNMT1, DNMT3A and DNMT3B.

In one embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_2$' is $Cy^6$, and $Cy^6$ is a known ring system selected from group consisting of:
(i) phenyl;
(ii) 5- to 6-membered heteroaromatic ring;
(iii) phenyl fused to a 3- to 7-membered saturated or partially unsaturated or aromatic carbocyclic or heterocyclic monocyclic ring;
(iv) 5- to 6-membered heteroaromatic ring fused to a 3- to 7-membered saturated or partially unsaturated or aromatic carbocyclic or heterocyclic monocyclic ring;
(v) phenyl fused to a 6- to 14-membered saturated or partially unsaturated carbocyclic or heterocyclic bicyclic ring, wherein the rings of the bicyclic ring are spiro-fused; and
(vi) 5- to 6-membered heteroaromatic ring fused to a 6- to 14-membered saturated or partially unsaturated carbocyclic or heterocyclic bicyclic ring, wherein the rings of the bicyclic ring are spiro-fused;

wherein $R_2$' is optionally substituted as previously defined; with the proviso that the compound of formula (I') is other than the ones listed in table 1.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein in $R_1$, $Cy^2$ and $Cy^3$ are independently a known ring system selected from a 3- to 7-membered carbocyclic or heterocyclic monocyclic ring, which is saturated or partially unsaturated; and a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_2$' is other than unsubstituted phenyl, 4-methylphenyl, 4-chlorophenyl, 2-chlorophenyl, 3,4-dichlorophenyl, 4-fluorophenyl and 4-methoxyphenyl.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_3$ is selected from halogen, —CN and —$OR^{c'}$; more particularly, $R_3$ is selected from halogen and —$OR^{c'}$.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_3$ is —$OR^{c'}$; more particularly, $R^{c'}$ is H or $R^c$; wherein $R^c$ is $(C_1-C_6)$alkyl optionally substituted with one or more halogen atoms.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_4$ is $OR^a$. More particularly, $R^a$ in $R_4$ is $Z^3$ optionally substituted as previously defined.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_4$ is $OR^a$ with the condition that $R^a$ contains at least one nitrogen atom.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_4$ is $OCy^2$ or $OZ^3$ as previously defined, wherein $Cy^2$ is optionally substituted as previously defined and $Z^3$ is substituted with one or more substituents $R^b$ and/or one $Cy^3$, as previously defined. More particularly, $R_4$ is $OCy^2$ as previously defined or $R_4$ is $OZ^3$, wherein $Z^3$ is $(C_1-C_6)$alkyl substituted with one or more substituents $R^b$ and/or one $Cy^3$, as previously defined. Even more particularly, $R_4$ is $OCy^2$ as previously defined or $R_4$ is $OZ^3$, wherein $Z^3$ is $(C_1-C_6)$alkyl substituted with one or more substituents $R^b$ and/or one $Cy^3$, as previously defined with the condition that $Z^3$ contains at least one nitrogen atom.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_2$' is $Cy^6$, and $Cy^6$ is a known ring system selected from group consisting of:
(i) phenyl;
(ii) phenyl fused to a 3- to 7-membered saturated or partially unsaturated or aromatic carbocyclic or heterocyclic monocyclic ring;
(iii) 5- to 6-membered heteroaromatic ring; and
(iv) 5- to 6-membered heteroaromatic ring fused to a 3- to 7-membered saturated or partially unsaturated or aromatic carbocyclic or heterocyclic monocyclic ring;
wherein $R_2$' is optionally substituted as previously defined.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_2$' is attached to the quinoline through a carbon atom.

In another embodiment, optionally in combination with one or more features of the various embodiments described above or below, the invention relates to the compound of formula (I') for use in the treatment and/or prevention of cancer mediated by the inhibition of histone methyltransferase G9a and of one or more DNMTs selected from the group consisting of DNMT1, DNMT3A and DNMT3B, wherein $R_2$' is phenyl or 5- to 6-membered heteroaromatic monocyclic ring, being both groups optionally substituted as previously defined. More particularly, $R_2$' is 5- to 6-membered heteroaromatic monocyclic ring optionally substituted as previously defined, even more particularly, $R_2$' is attached to the quinoline through a carbon atom, and even more particularly, $R_2$' is selected from the group consisting of 2-thiophene, 2-pyrrol, 3-pyrrol, 2-furan and 3-furan.

As mentioned above the invention also relates to a method for generating an induced pluripotent stem cell by culturing an isolated cell together with one or more transcription factors and a compound of formula (I'), or its salts, or its stereoisomers or mixtures, either of the compound of formula (I') or of its salts.

In one embodiment, optionally in combination with one or more features of the various embodiments described above or below, the invention relates to the method for generating an induced pluripotent stem cell as defined above, wherein in the compound of formula (I') $R_2$' is $Cy^6$, and $Cy^6$ is a known ring system selected from group consisting of:
(i) phenyl;
(ii) 5- to 6-membered heteroaromatic ring;
(iii) phenyl fused to a 3- to 7-membered saturated or partially unsaturated or aromatic carbocyclic or heterocyclic monocyclic ring;
(iv) 5- to 6-membered heteroaromatic ring fused to a 3- to 7-membered saturated or partially unsaturated or aromatic carbocyclic or heterocyclic monocyclic ring;
(v) phenyl fused to a 6- to 14-membered saturated or partially unsaturated carbocyclic or heterocyclic bicyclic ring, wherein the rings of the bicyclic ring are spiro-fused; and
(vi) 5- to 6-membered heteroaromatic ring fused to a 6- to 14-membered saturated or partially unsaturated carbocyclic or heterocyclic bicyclic ring, wherein the rings of the bicyclic ring are spiro-fused;
wherein $R_2$' is optionally substituted as previously defined; with the proviso that the compound of formula (I') is other than the ones listed in table 1.

In another embodiment, optionally in combination with one or more features of the various embodiments described above or below, the invention relates to the method for generating an induced pluripotent stem cell as defined above, wherein in the compound of formula (I'), in $R_1$, $Cy^2$ and $Cy^3$ are independently a known ring system selected from a 3- to 7-membered carbocyclic or heterocyclic monocyclic ring, which is saturated or partially unsaturated; and a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring.

In another embodiment, optionally in combination with one or more features of the various embodiments described above or below, the invention relates to the method for generating an induced pluripotent stem cell as defined above, wherein in the compound of formula (I') $R_2$' is other than unsubstituted phenyl, 4-methylphenyl, 4-chlorophenyl, 2-chlorophenyl, 3,4-dichlorophenyl, 4-fluorophenyl and 4-methoxyphenyl.

In another embodiment, optionally in combination with one or more features of the various embodiments described above or below, the invention relates to the method for generating an induced pluripotent stem cell as defined above, wherein in the compound of formula (I'), $R_3$ is selected from halogen, —CN and —$OR^{c'}$; more particularly, $R_3$ is selected from halogen and —$OR^{c'}$.

In another embodiment, optionally in combination with one or more features of the various embodiments described above or below, the invention relates to the method for generating an induced pluripotent stem cell as defined above, wherein in the compound of formula (I') $R_3$ is —$OR^{c'}$; more particularly, $R^{c'}$ is H or $R^c$; wherein $R^c$ is $(C_1-C_6)$alkyl optionally substituted with one or more halogen atoms.

In another embodiment, optionally in combination with one or more features of the various embodiments described above or below, the invention relates to the method for generating an induced pluripotent stem cell as defined above, wherein in the compound of formula (I') $R_4$ is $OR^a$. More particularly, $R^a$ in $R_4$ is $Z^3$ optionally substituted as previously defined.

In another embodiment, optionally in combination with one or more features of the various embodiments described above or below, the invention relates to the method for generating an induced pluripotent stem cell as defined above, wherein in the compound of formula (I'), $R_4$ is $OR^a$ with the condition that $R^a$ contains at least one nitrogen atom.

In another embodiment, optionally in combination with one or more features of the various embodiments described above or below, the invention relates to the method for generating an induced pluripotent stem cell as defined above, wherein in the compound of formula (I'), $R_4$ is $OCy^2$ or $OZ^3$ as previously defined, wherein $Cy^2$ is optionally substituted as previously defined and $Z^3$ is substituted with one or more substituents $R^b$ and/or one $Cy^3$, as previously defined. More particularly, $R_4$ is $OCy^2$ as previously defined or $R_4$ is $OZ^3$, wherein $Z^3$ is $(C_1-C_6)$alkyl substituted with one or more substituents $R^b$ and/or one $Cy^3$, as previously defined. Even more particularly, $R_4$ is $OCy^2$ as previously defined or $R_4$ is $OZ^3$, wherein $Z^3$ is $(C_1-C_6)$alkyl substituted with one or more substituents $R^b$ and/or one $Cy^3$, as previously defined with the condition that $Z^3$ contains at least one nitrogen atom.

In another embodiment, optionally in combination with one or more features of the various embodiments described above or below, the invention relates to the method for generating an induced pluripotent stem cell as defined above, wherein in the compound of formula (I') $R_2'$ is $Cy^6$, and $Cy^6$ is a known ring system selected from group consisting of:
  (i) phenyl;
  (ii) phenyl fused to a 3- to 7-membered saturated or partially unsaturated or aromatic carbocyclic or heterocyclic monocyclic ring;
  (iii) 5- to 6-membered heteroaromatic ring; and
  (iv) 5- to 6-membered heteroaromatic ring fused to a 3- to 7-membered saturated or partially unsaturated or aromatic carbocyclic or heterocyclic monocyclic ring;
wherein $R_2'$ is optionally substituted as previously defined.

In another embodiment, optionally in combination with one or more features of the various embodiments described above or below, the invention relates to the method for generating an induced pluripotent stem cell as defined above, wherein in the compound of formula (I'), $R_2$ is attached to the quinoline through a carbon atom.

In another embodiment, optionally in combination with one or more features of the various embodiments described above or below, the invention relates to the method for generating an induced pluripotent stem cell as defined above, wherein in the compound of formula (I') $R_2'$ is phenyl or 5- to 6-membered heteroaromatic monocyclic ring, being both groups optionally substituted as previously defined. More particularly, $R_2'$ is 5- to 6-membered heteroaromatic monocyclic ring optionally substituted as previously defined, even more particularly, $R_2'$ is attached to the quinoline through a carbon atom, and even more particularly, $R_2'$ is selected from the group consisting of 2-thiophene, 2-pyrrol, 3-pyrrol, 2-furan and 3-furan.

In another embodiment, optionally in combination with one or more features of the various embodiments described above or below, in the compound of formula (I) or (I') as previously described:
  a) $Cy^2$ and $Cy^3$ in $R_1$ are independently a known ring system selected from a 3- to 7-membered carbocyclic or heterocyclic monocyclic ring, which is saturated or partially unsaturated; and a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring; and
  b) $R_2$ or $R_2'$ is attached to the quinoline through a carbon atom; more particularly $R_2$ or $R_2'$ is phenyl or 5- to 6-membered heteroaromatic monocyclic ring, being $R_2$ or $R_2'$ attached to the quinoline through a carbon atom and optionally substituted as previously defined; more particularly, $R_2$ or $R_2'$ is 5- to 6-membered heteroaromatic monocyclic ring attached to the quinoline through a carbon atom and optionally substituted as previously defined; and even more particularly, $R_2$ or $R_2'$ is selected from the group consisting of 2-thiophene, 2-pyrrol, 3-pyrrol, 2-furan and 3-furan.

In another embodiment, optionally in combination with one or more features of the various embodiments described above or below, in the compound of formula (I) or (I') as previously described:
  a) $Cy^2$ and $Cy^3$ in $R_1$ are independently a known ring system selected from a 3- to 7-membered carbocyclic or heterocyclic monocyclic ring, which is saturated or partially unsaturated; and a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring; and
  b) $R_4$ is $OR^a$ with the condition that $R^a$ contains at least one nitrogen atom, or alternatively $R_4$ is $OCy^2$ or $OZ^3$ as previously defined, wherein $Cy^2$ is optionally substituted as previously defined and $Z^3$ is substituted with one or more substituents $R^b$ and/or one $Cy^3$, as previously defined. More particularly, $R_4$ is $OCy^2$ as previously defined or $R_4$ is $OZ^3$, wherein $Z^3$ is $(C_1-C_6)$alkyl substituted with one or more substituents $R^b$ and/or one $Cy^3$, as previously defined. Even more particularly, $R_4$ is $OCy^2$ as previously defined or $R_4$ is $OZ^3$, wherein $Z^3$ is $(C_1-C_6)$alkyl substituted with one or more substituents $R^b$ and/or one $Cy^3$, as previously defined with the condition that $Z^3$ contains at least one nitrogen atom.

Additionally, all embodiments of the invention referring to the compounds of formula (I) also apply to the compound of formula (I') either when used in the treatment and/or prevention of cancer or in a method for generating an induced pluripotent stem cell.

It also forms part of the invention a mesenchymal stem cell pretreated with a compound of formula (I'), or its salts, or its stereoisomers or mixtures, either of the compound of formula (I') or of its salts, for use in the treatment and/or prevention of immune-related diseases. Alternatively, this aspect can be formulated as the use of a mesenchymal stem cell pretreated with a compound of formula (I'), or its salts, or its stereoisomers or mixtures, either of the compound of formula (I') or of its salts, for the manufacture of a medicament for the treatment and/or prevention of immune-related diseases; and may also be formulated as a method for the treatment and/or prevention of immune-related diseases, comprising administering an effective amount of a mesenchymal stem cell pretreated with a compound of formula (I'), or its salts, or its stereoisomers or mixtures, either of the compound of formula (I') or of its salts, in a subject in need thereof, including a human.

It also forms part of the invention a method for obtaining a pretreated mesenchymal stem cell by culturing in an appropriate medium an isolated mesenchymal stem cell together with a compound of formula (I'), or its salts, or its stereoisomers or mixtures, either of the compound of formula (I') or of its salts.

In another embodiment of the invention, the compound of formula (I) is selected from the group consisting of:

3-02
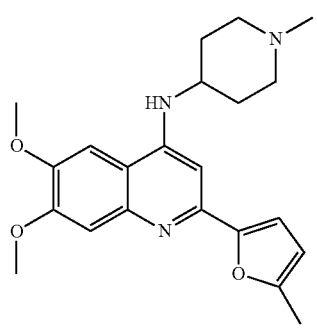
3-06
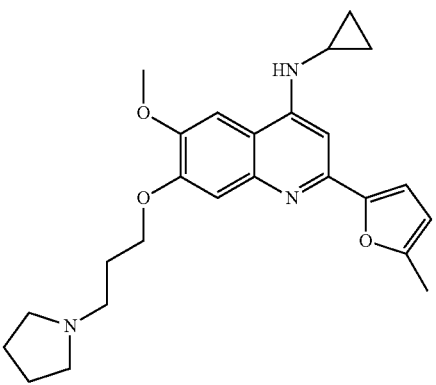
3-03
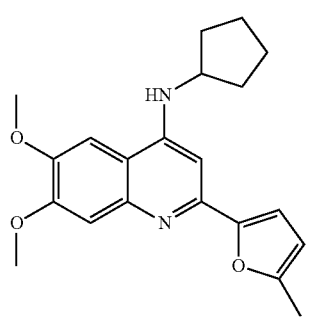
3-07
3-04
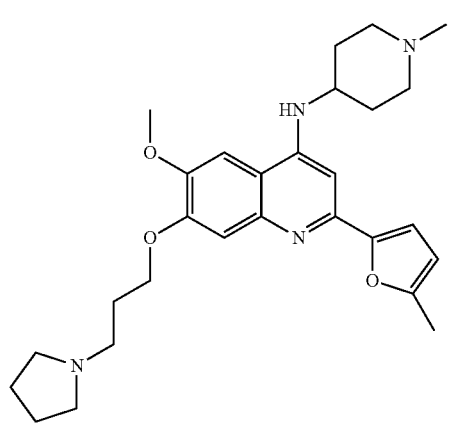
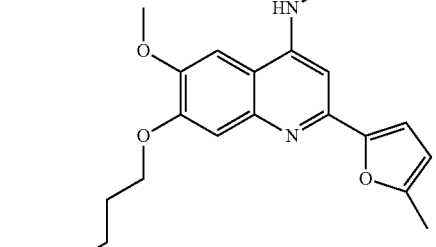
3-05
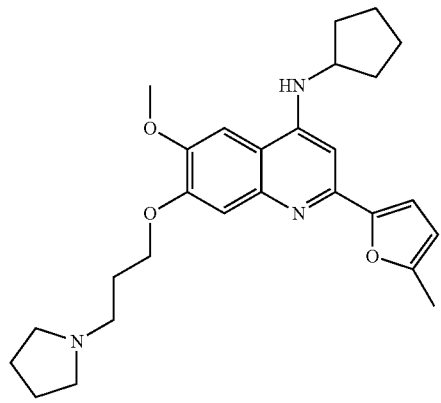
3-08
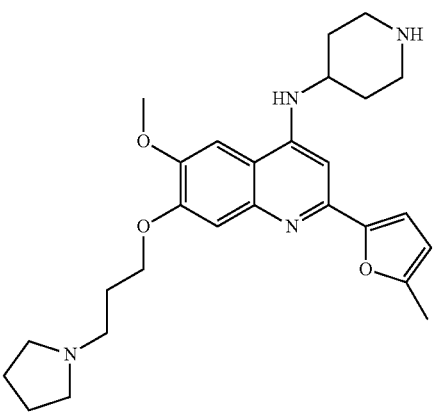

-continued
3-09
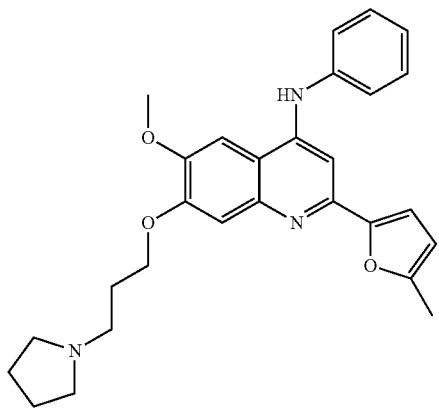
3-10
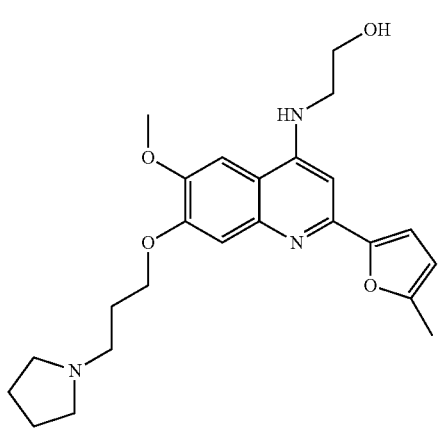
3-11
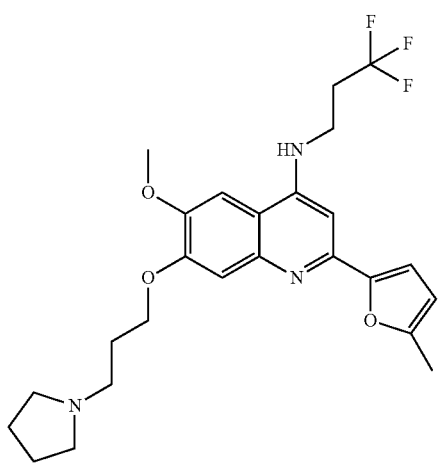
-continued
3-12
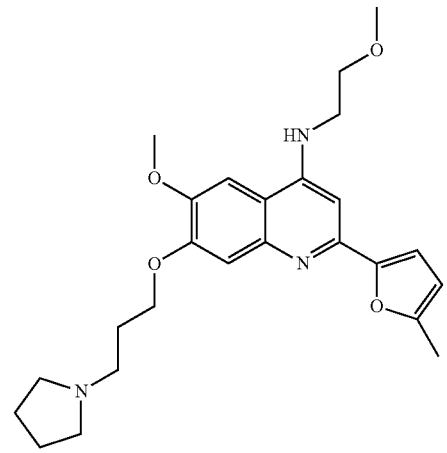
3-13
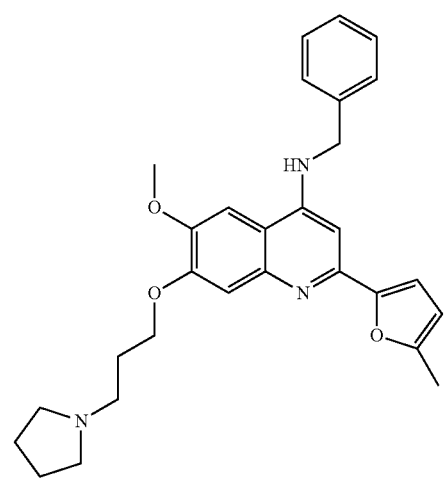
3-14
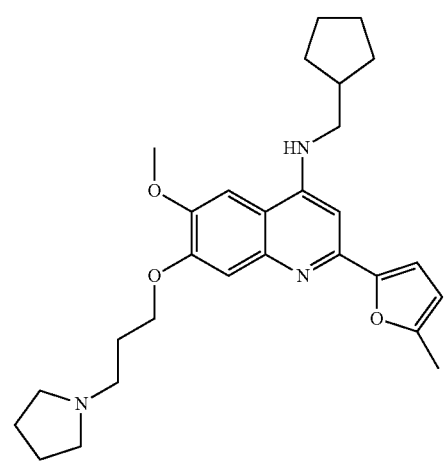

3-15
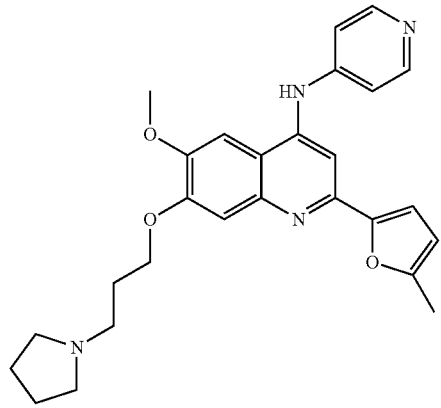
3-16
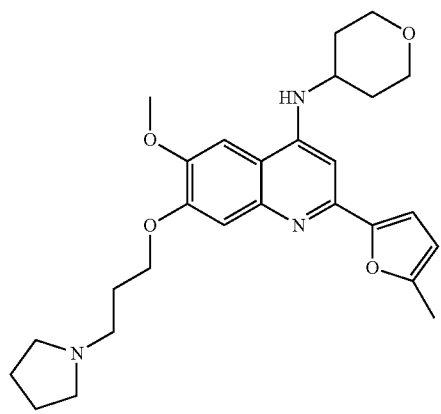
3-17
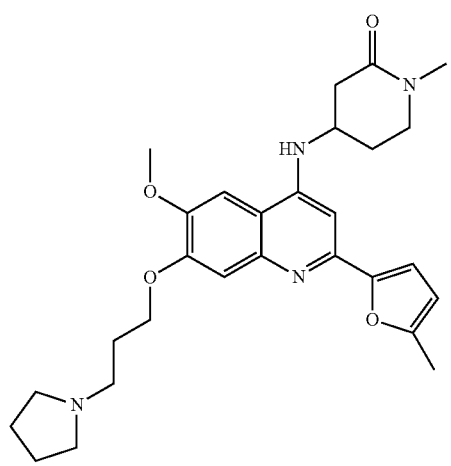
3-18
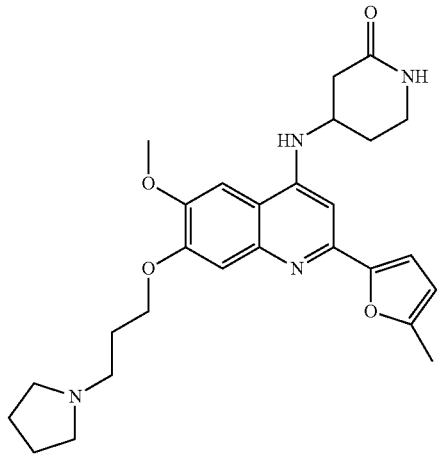
3-19
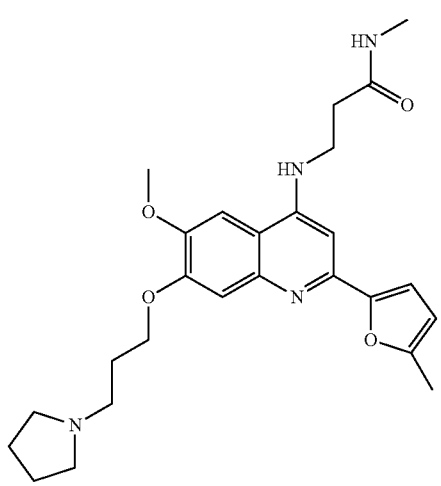
3-20
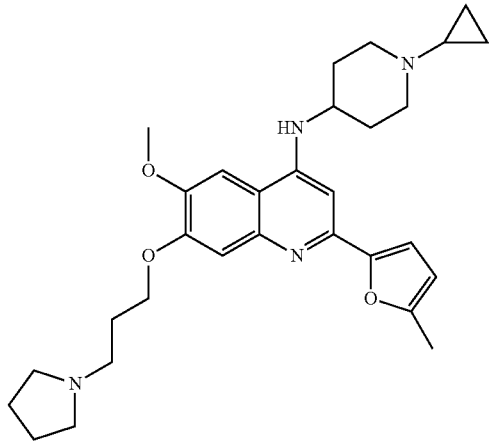

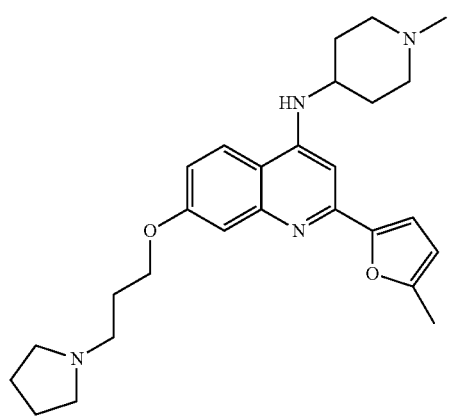
3-21
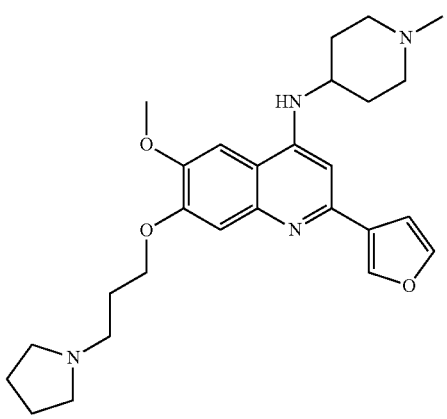
3-27
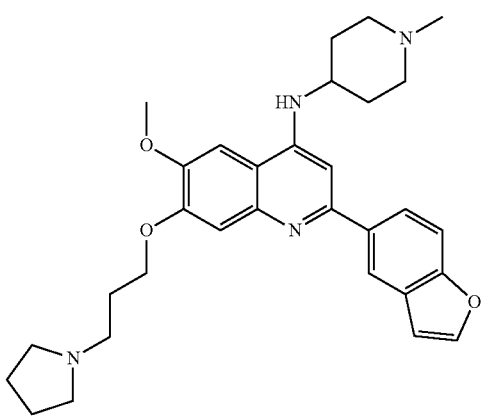
3-25
3-28
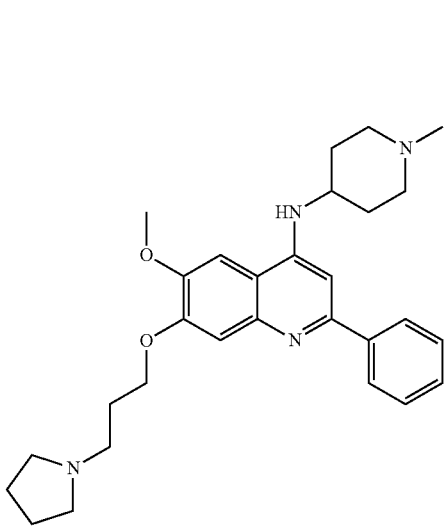
3-26
3-29

-continued
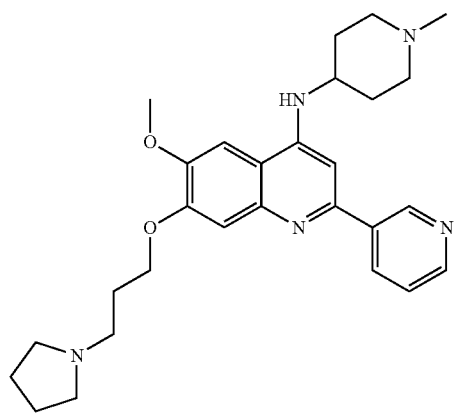
3-30
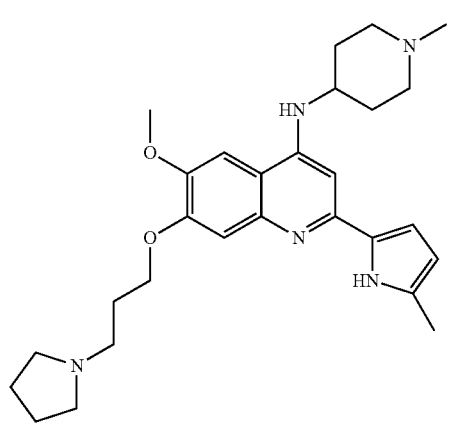
3-31
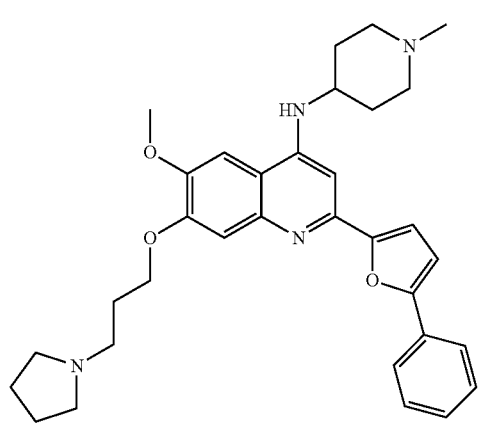
3-32
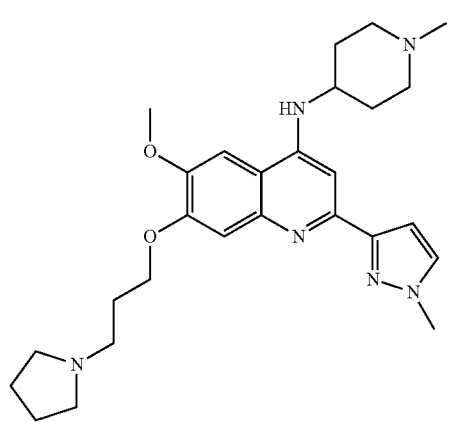
3-33
-continued
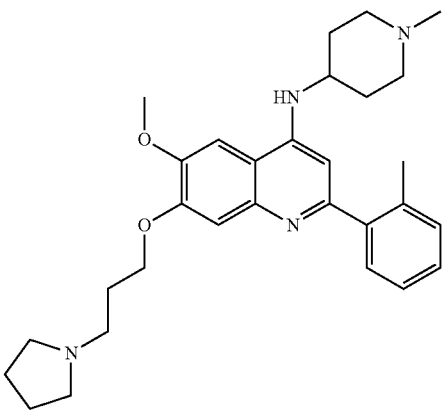
3-34
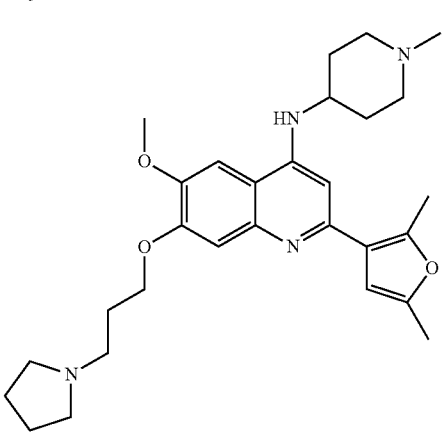
3-35
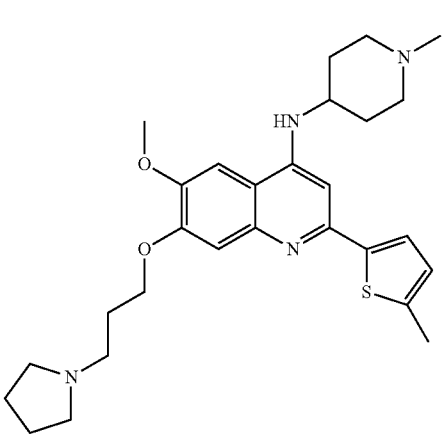
3-36
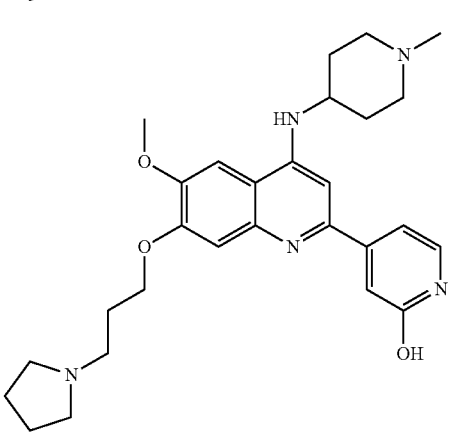
3-37

3-38
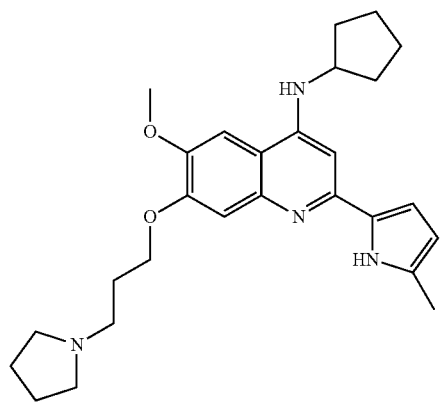
3-41
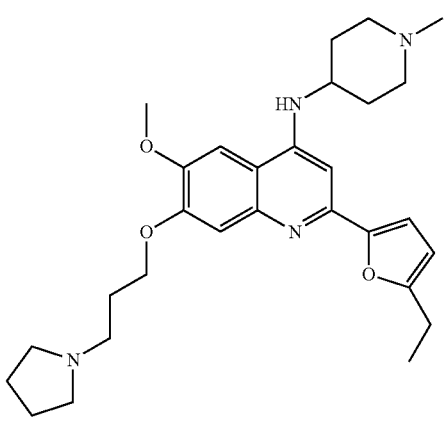
3-39
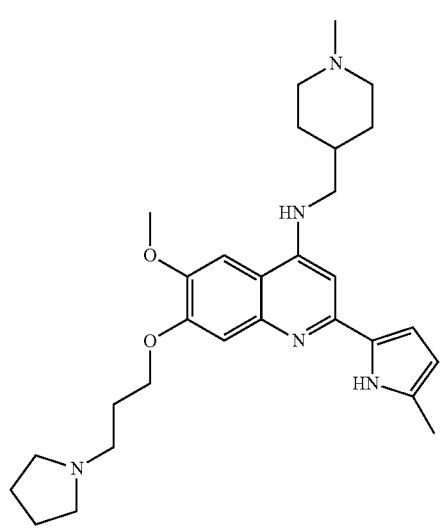
3-42
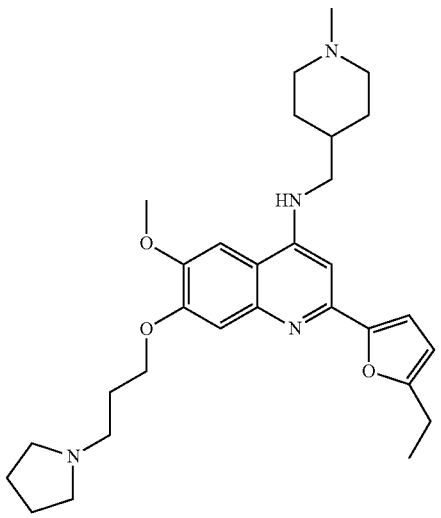
3-40
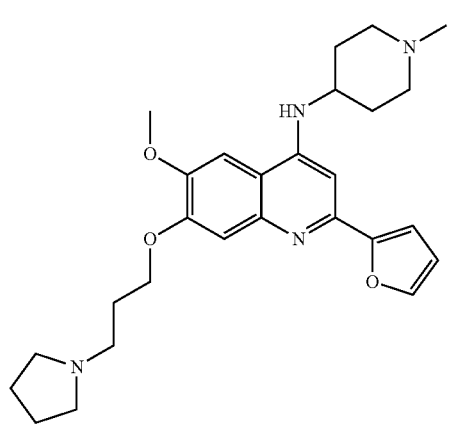
3-43
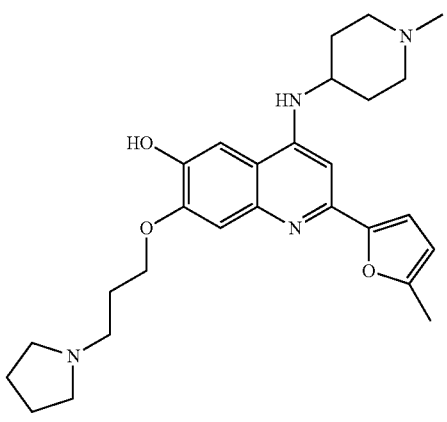

3-44
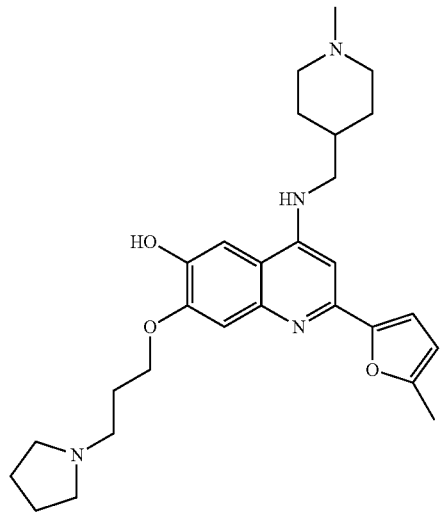
3-45
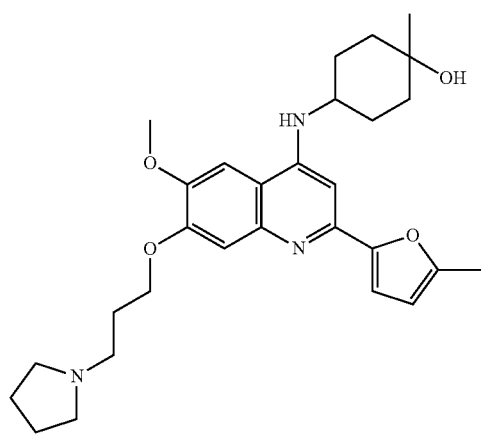
3-46
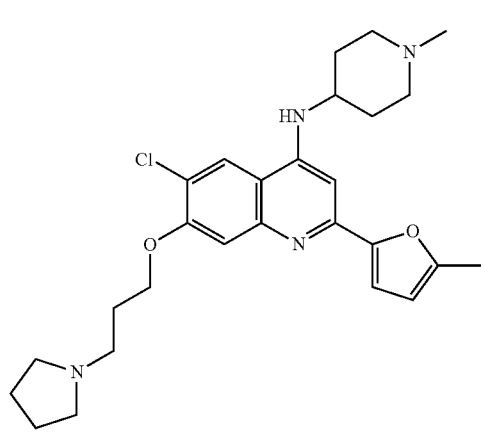
3-47
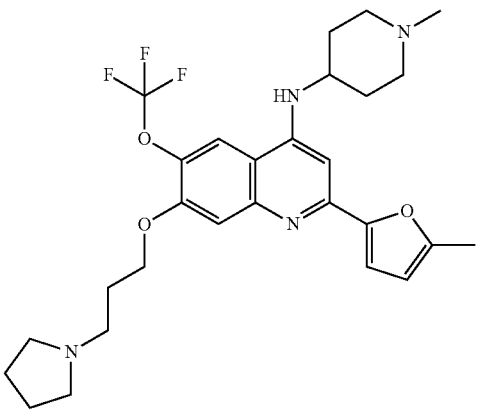
3-48
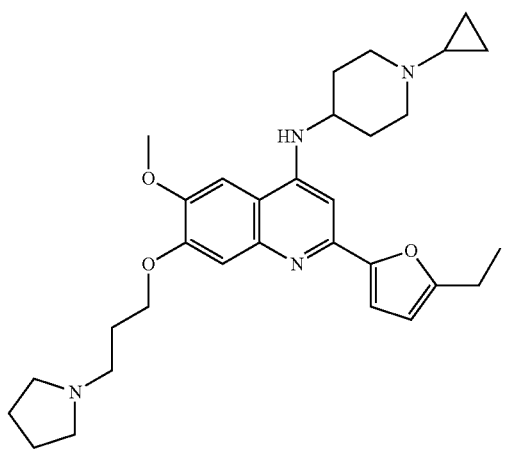
3-49
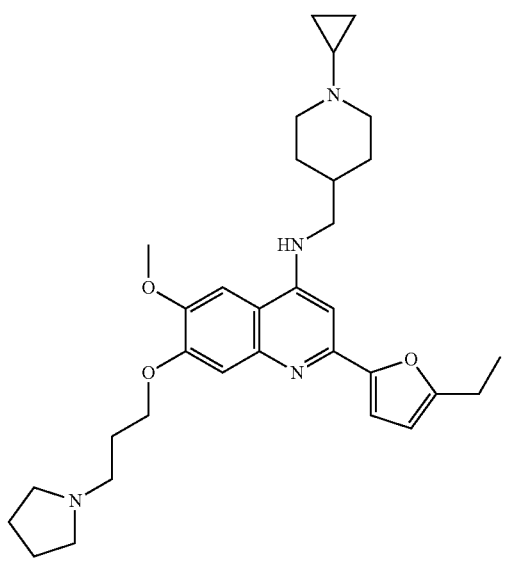

3-50
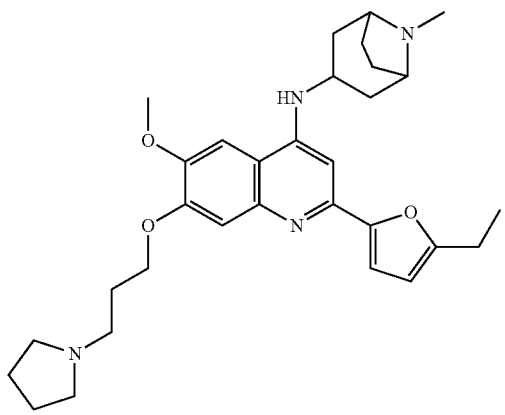
3-53
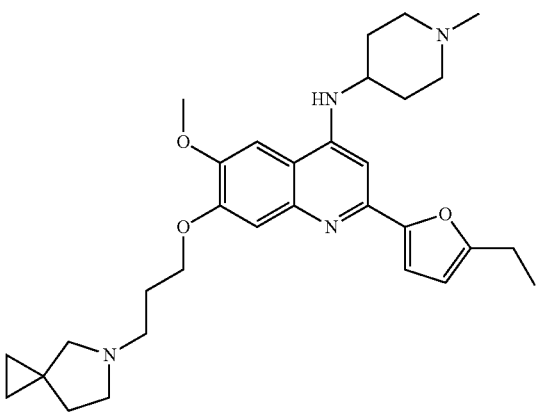
3-51
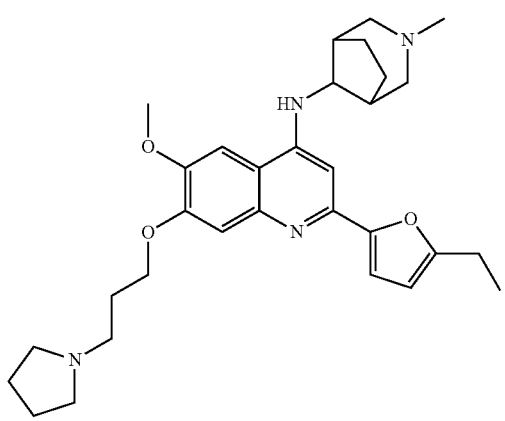
3-54
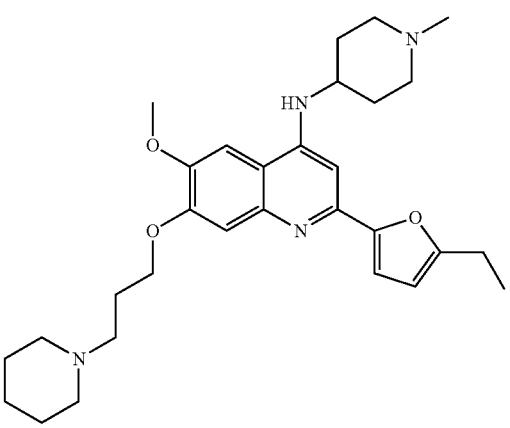
3-52
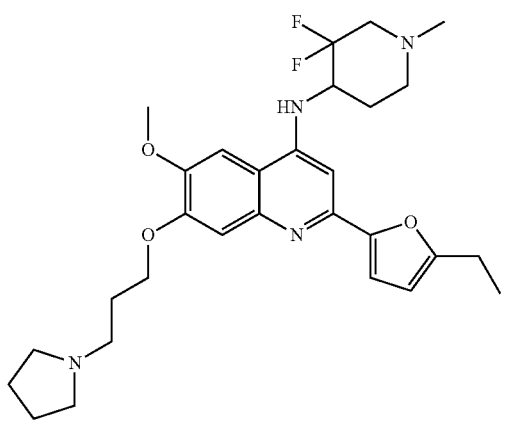
3-55
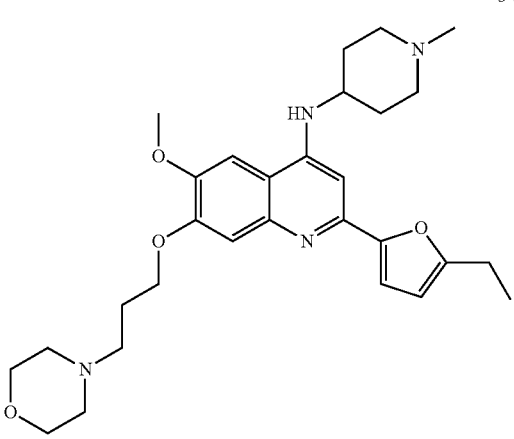

3-56
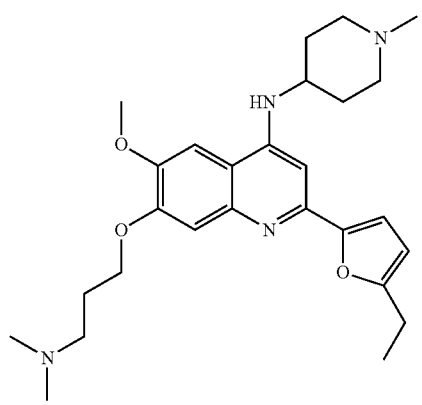
4-01
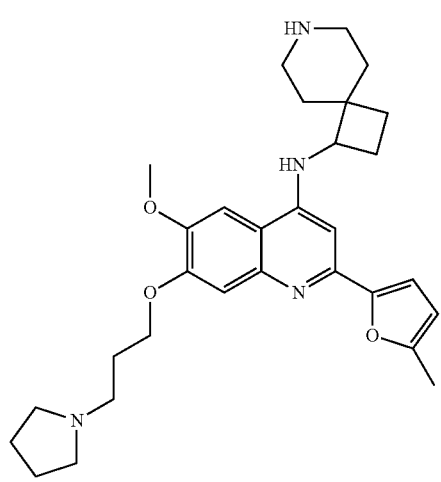
4-02
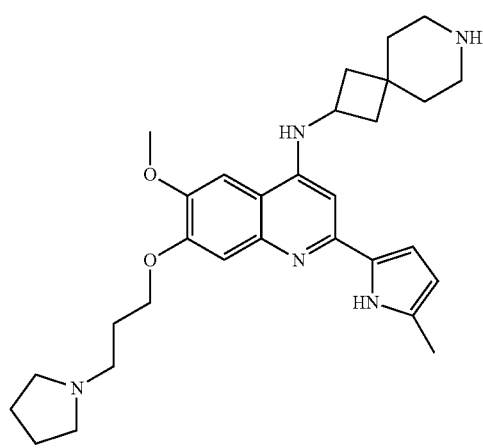
4-03
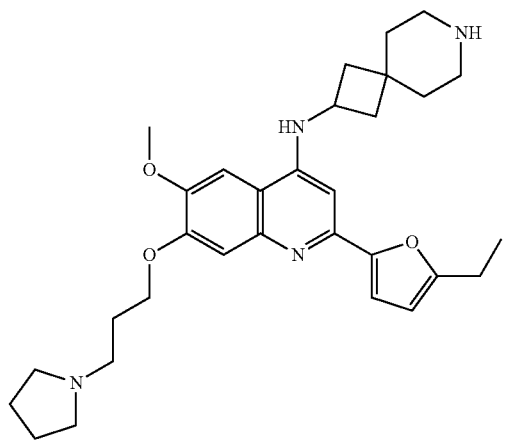
5-01
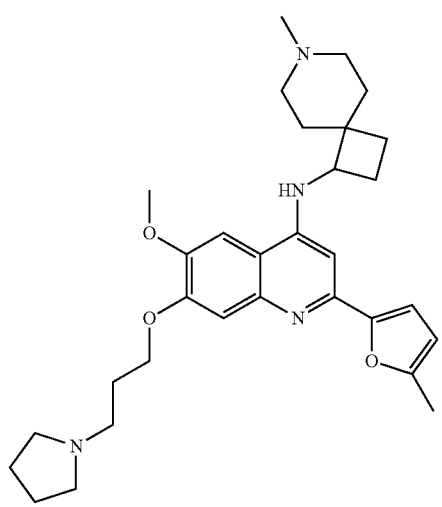
5-02
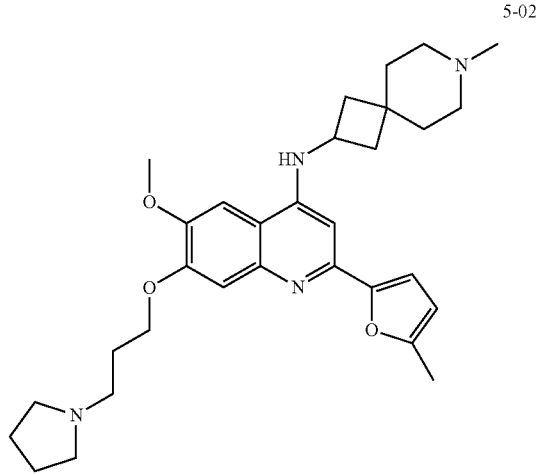

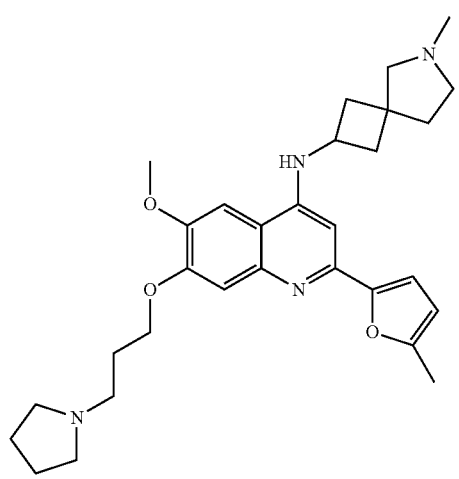
5-03
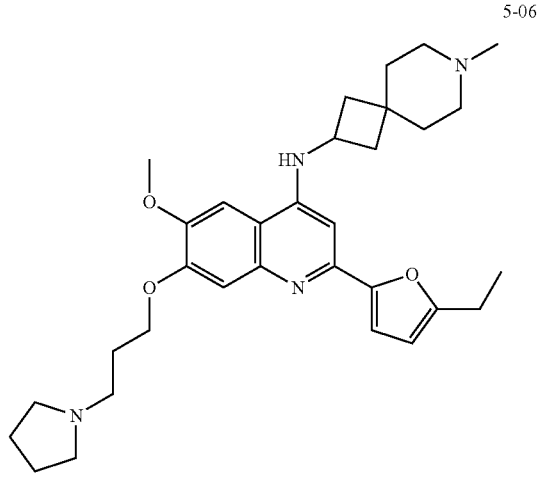
5-06
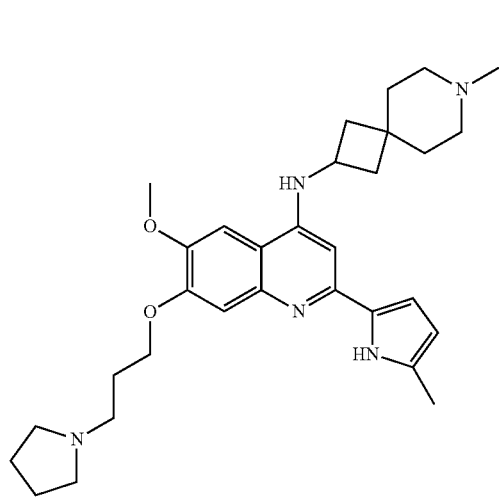
5-04
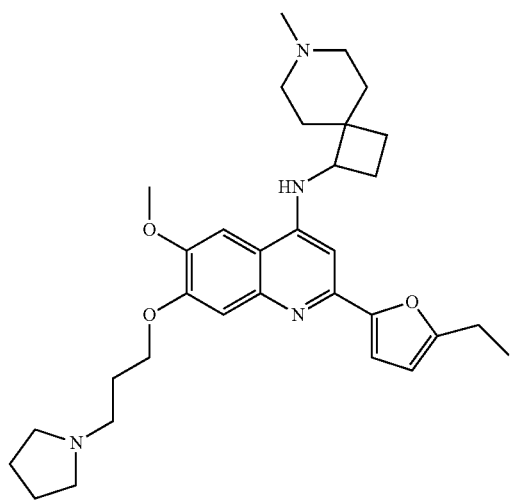
5-07
5-05
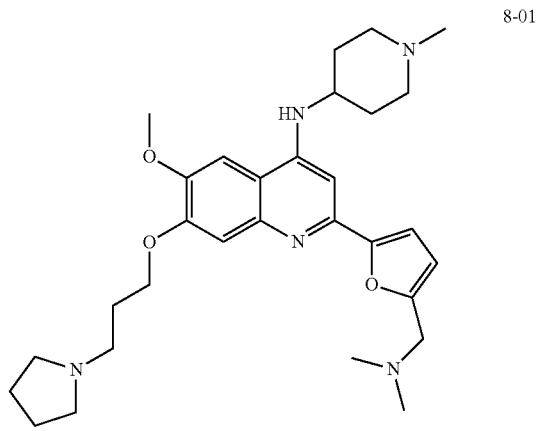
8-01

8-02
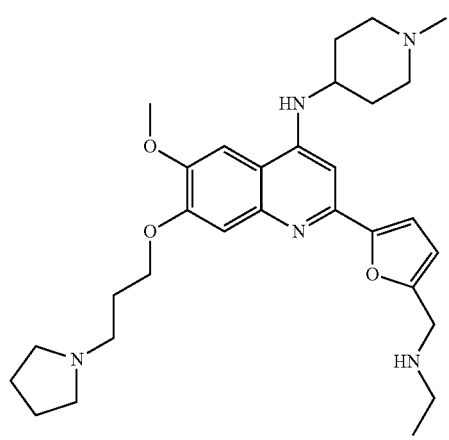
9-01
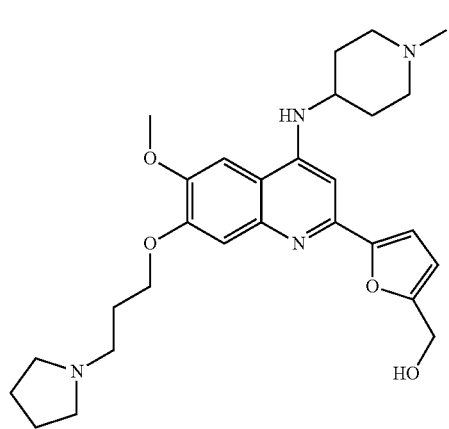
10-01
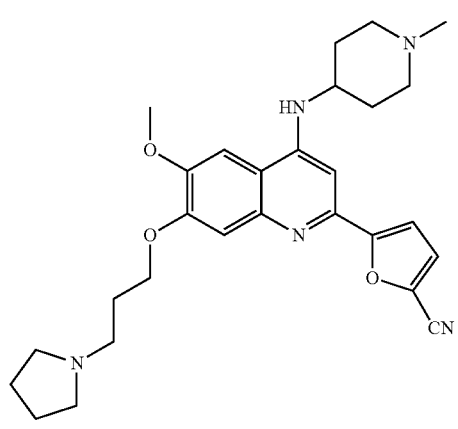
11-01
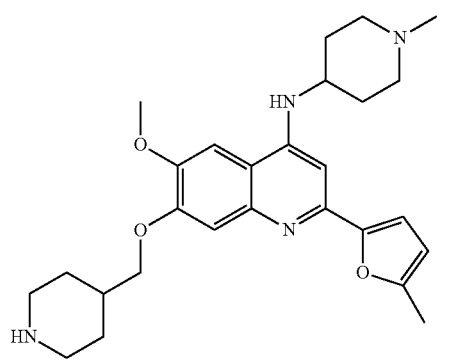
11-02
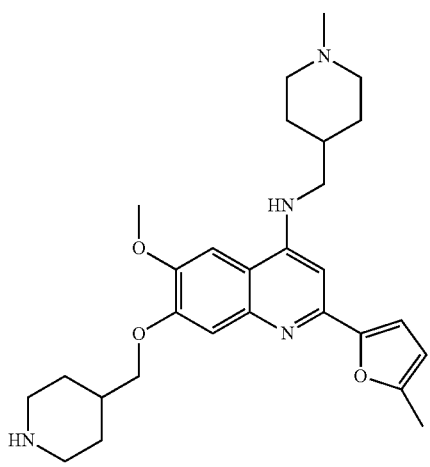
11-03
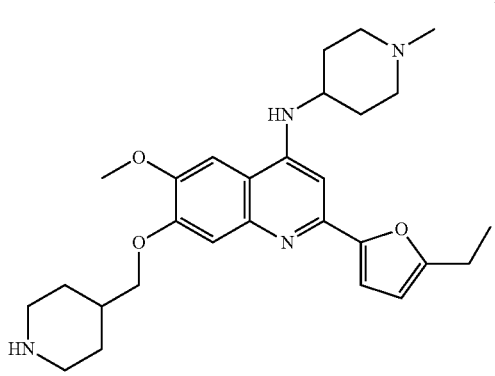
11-04
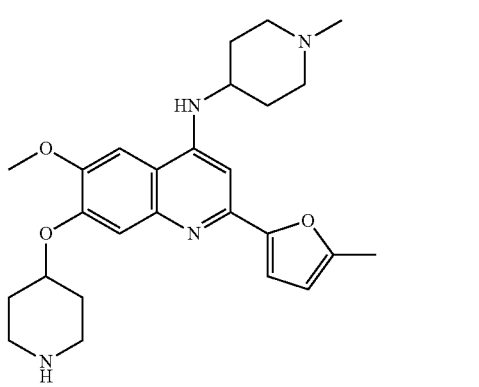
11-05
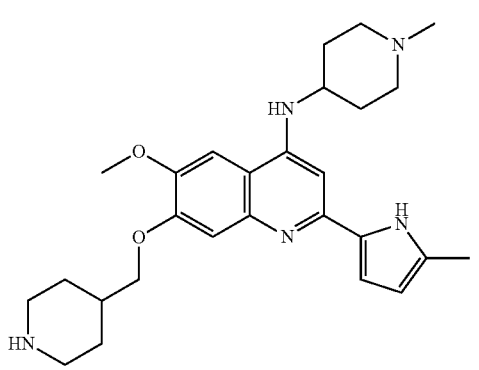

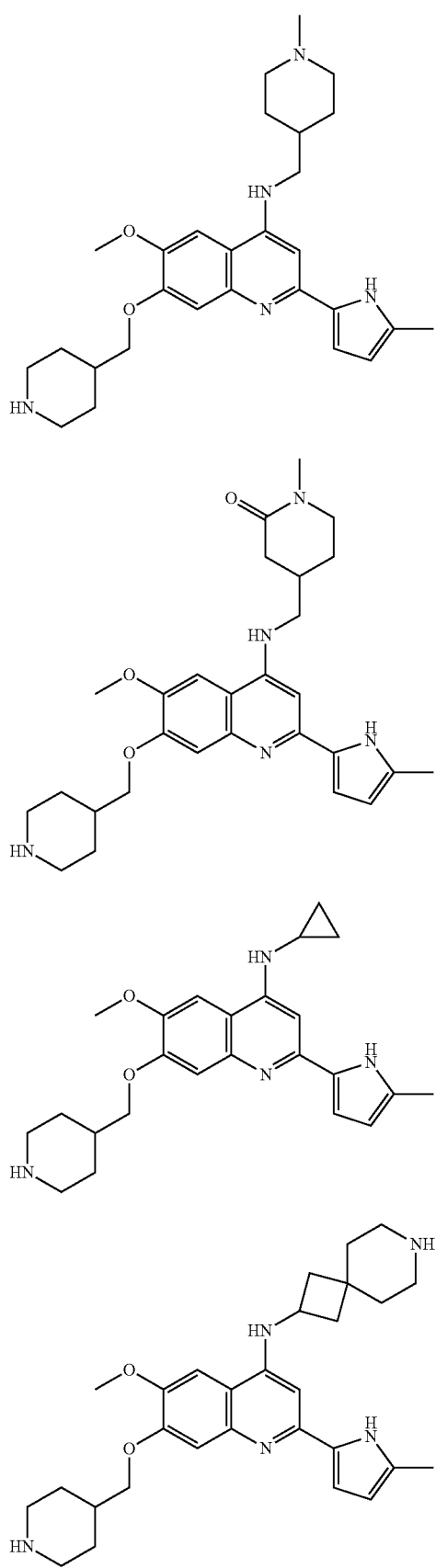
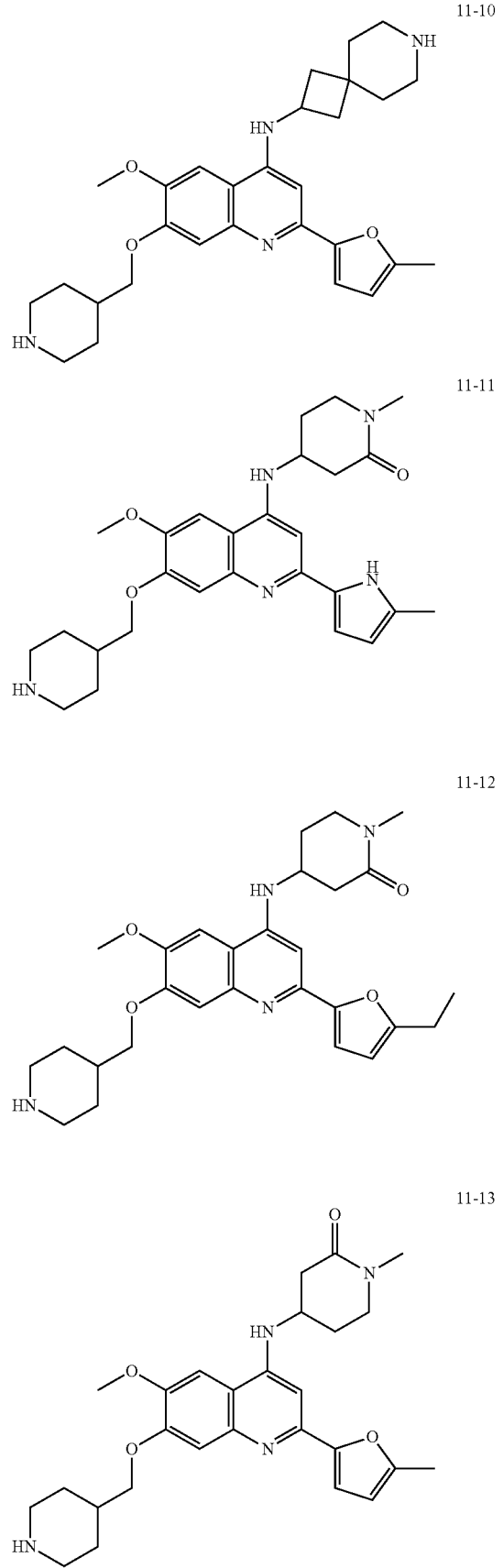

-continued
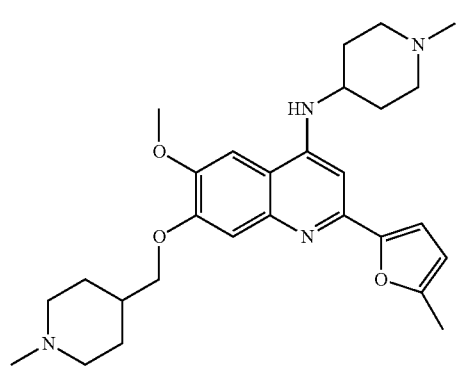
12-01
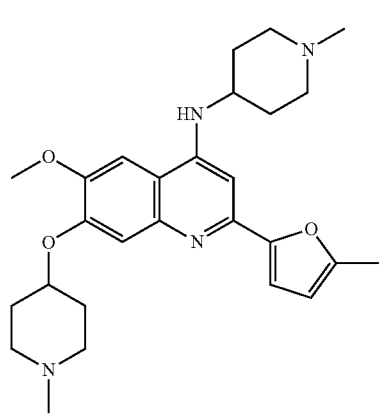
12-02
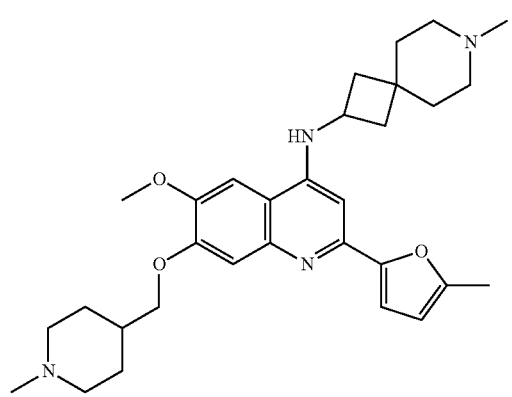
12-03
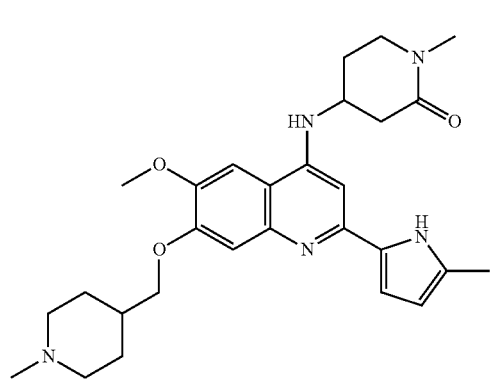
12-04
-continued
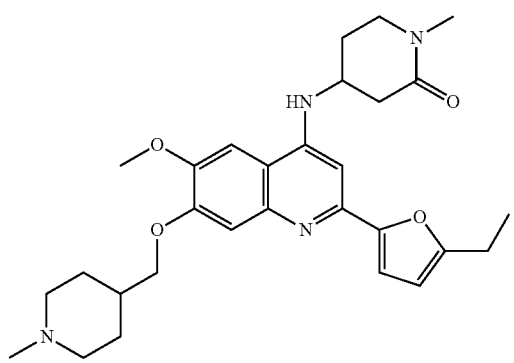
12-05
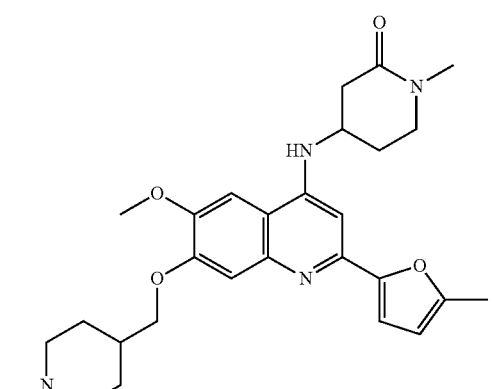
12-06
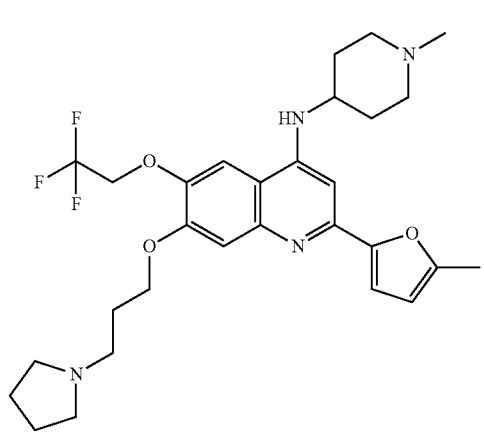
13-01
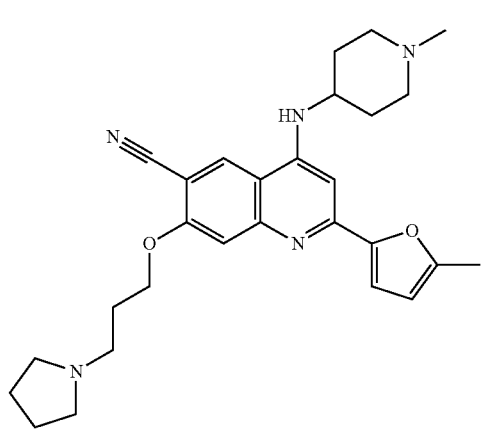
14-01

16-01
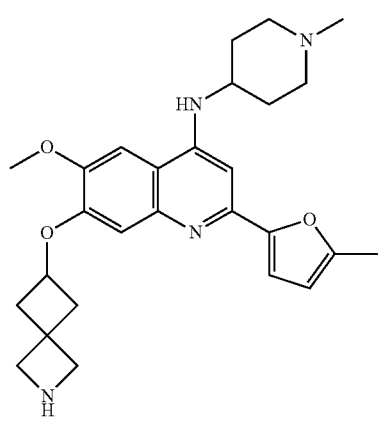
17-02
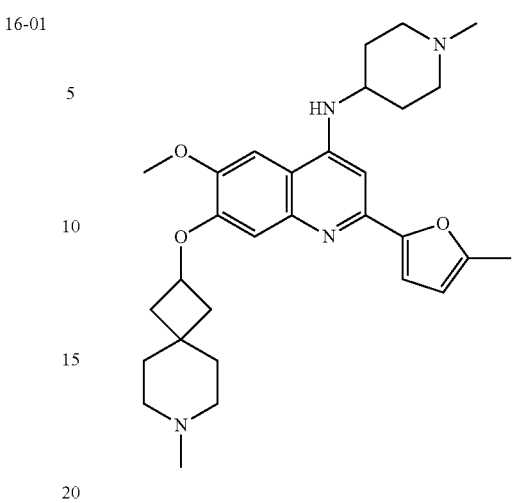
16-02
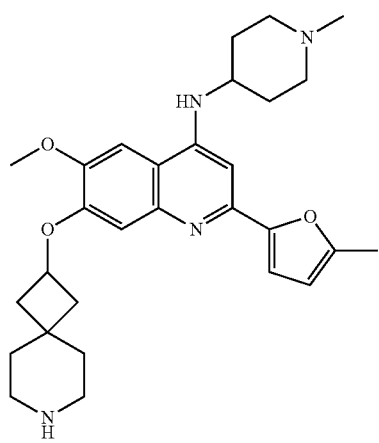
18-01
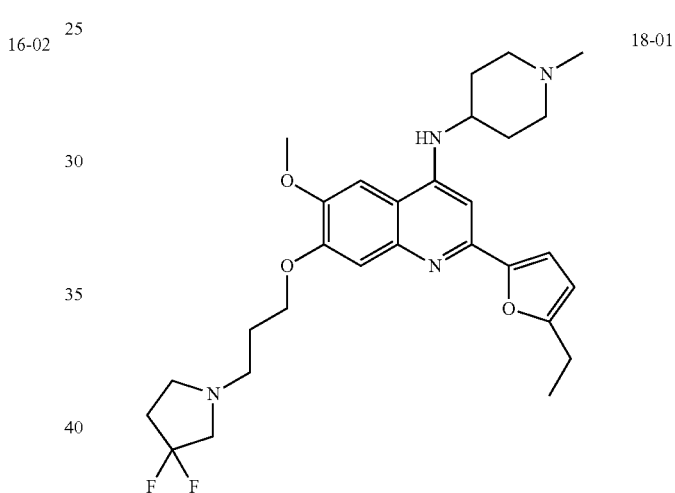
17-01
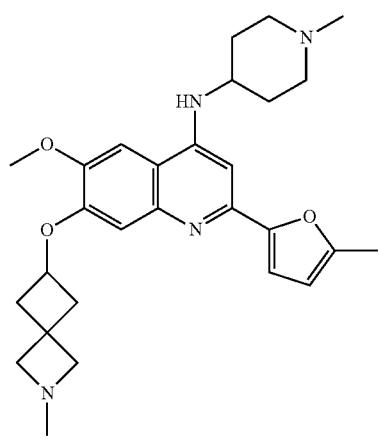
18-02
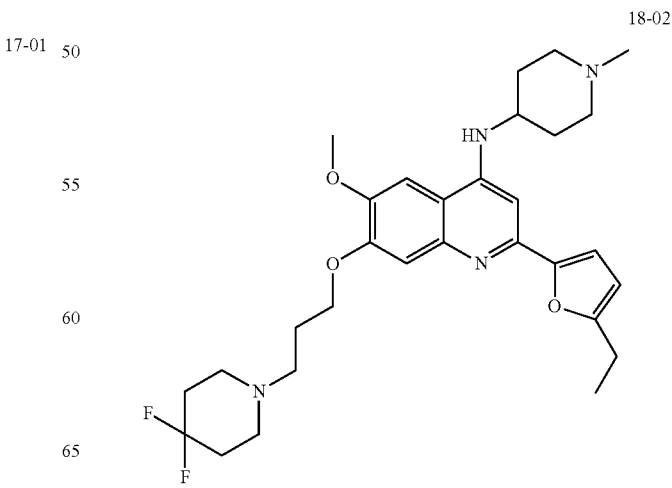

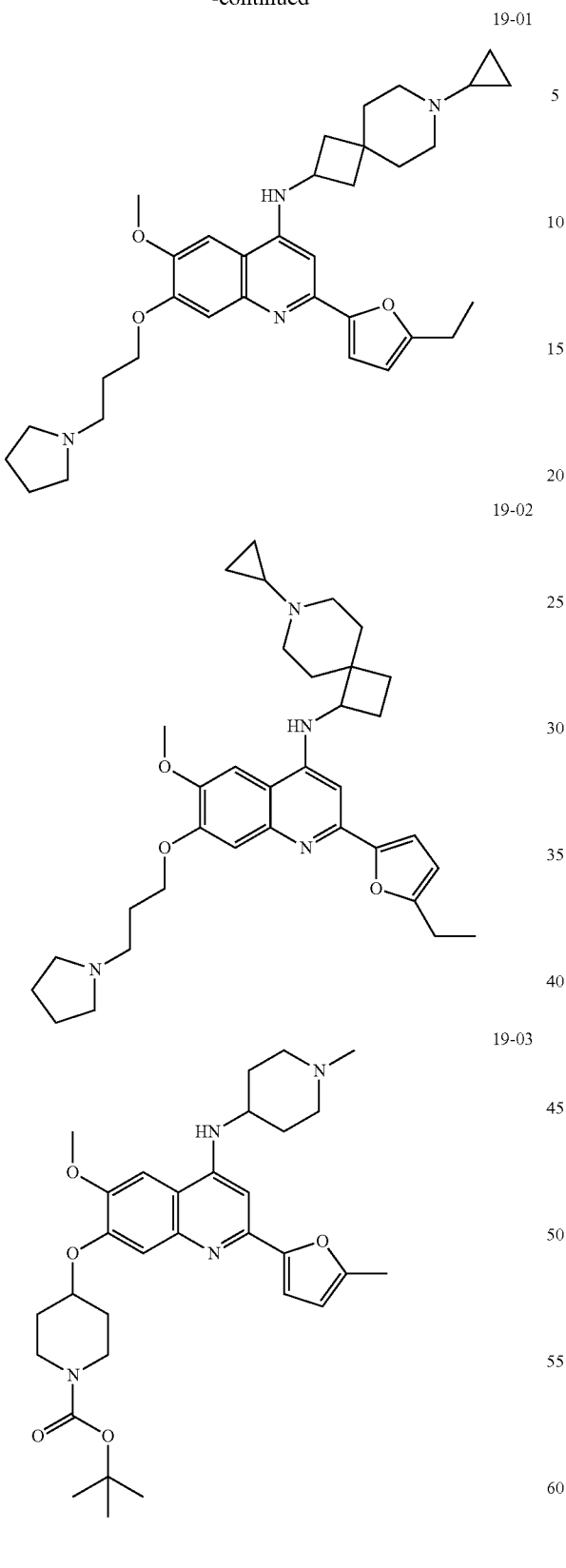
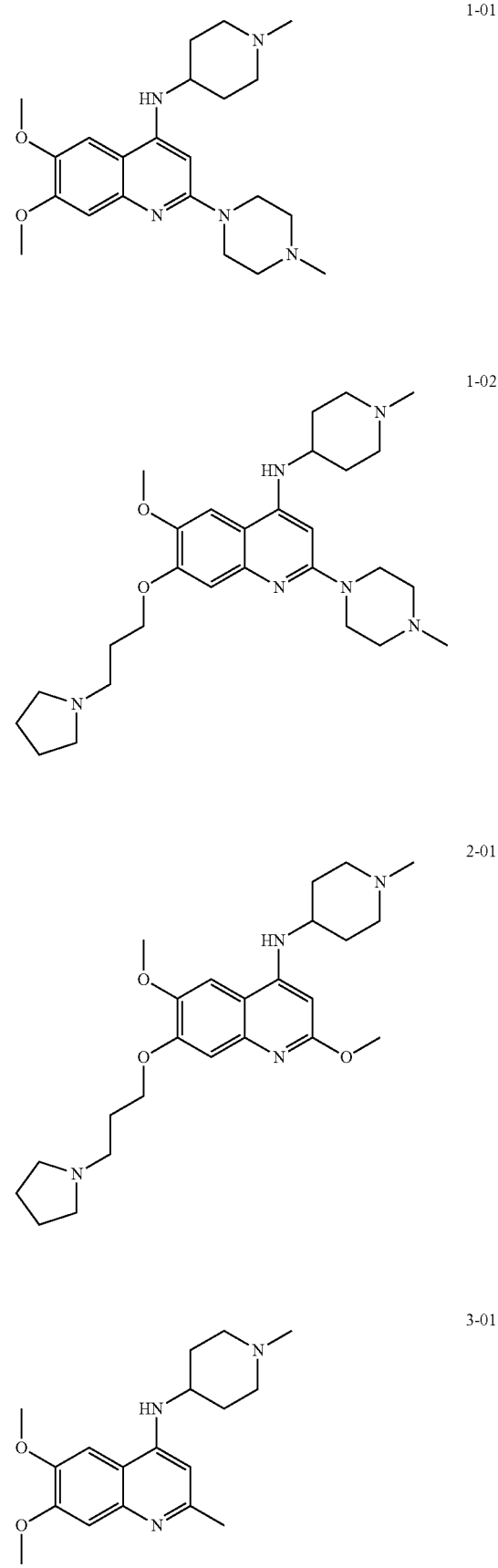
In another embodiment of the invention, the compound of formula (I') is selected from the group consisting of:

3-22
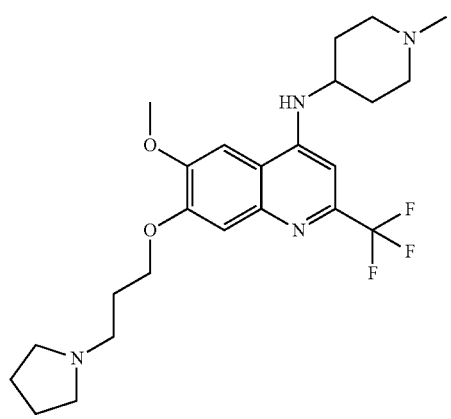
3-23
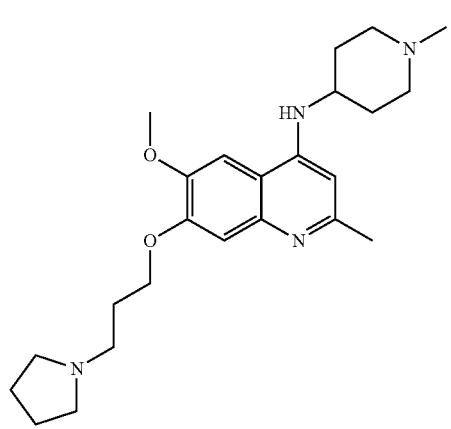
3-24
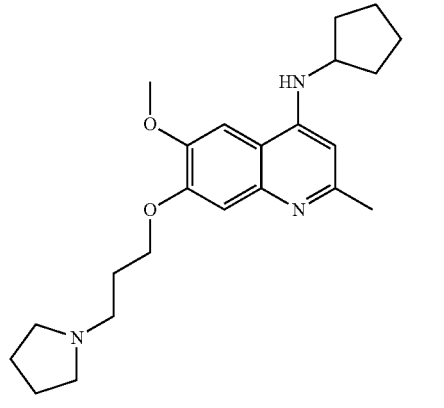
6-01
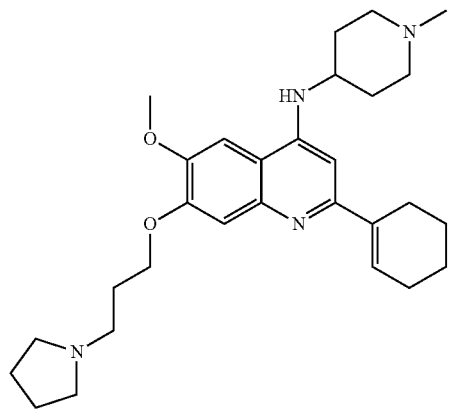
6-02
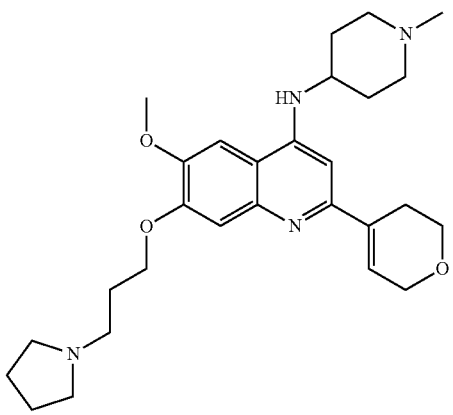
7-01
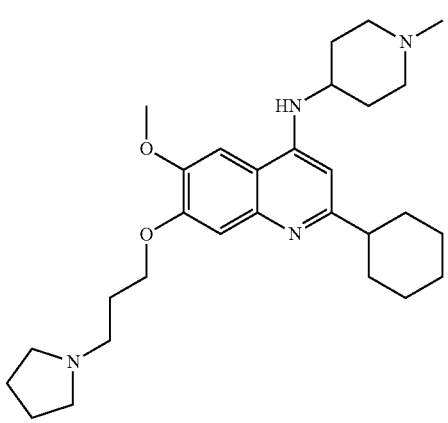
7-02
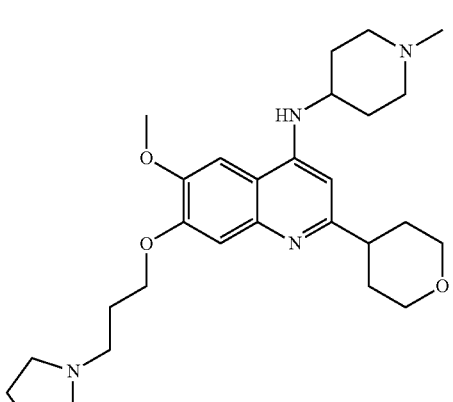
7-04
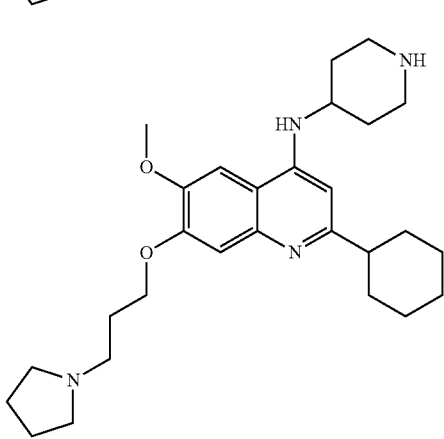

-continued 7-05

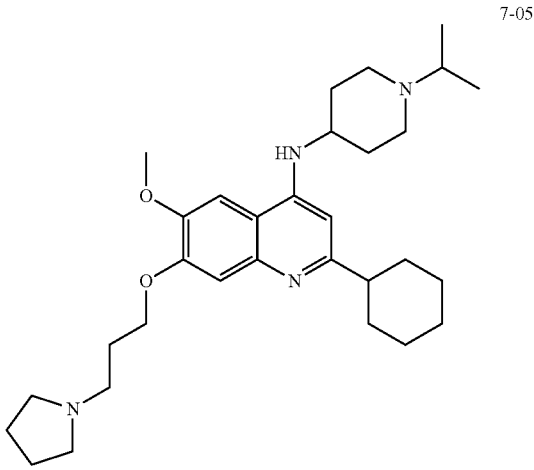

15-01

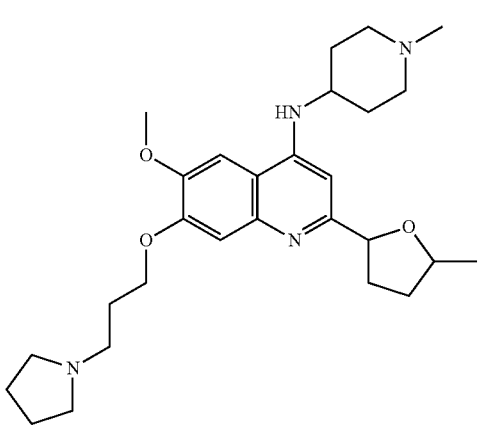

In another embodiment of the invention, the compound of formula (I') is selected from the group consisting of: 3-02, 3-03, 3-04, 3-05, 3-06, 3-07, 3-08, 3-09, 3-10, 3-11, 3-12, 3-13, 3-14, 3-15, 3-16, 3-17, 3-18, 3-19, 3-20, 3-21, 3-25, 3-26, 3-27, 3-28, 3-29, 3-30, 3-31, 3-32, 3-33, 3-34, 3-35, 3-36, 3-37, 3-38, 3-39, 3-40, 3-41, 3-42, 3-43, 3-44, 3-45, 3-46, 3-47, 3-48, 3-49, 3-50, 3-51, 3-52, 3-53, 3-54, 3-55, 3-56, 4-01, 4-02, 4-03, 5-01, 5-02, 5-03, 5-04, 5-05, 5-06, 5-07, 8-01, 8-02, 9-01, 10-01, 11-01, 11-02, 11-03, 11-04, 11-05, 11-06, 11-07, 11-08, 11-09, 11-10, 11-11, 11-12, 11-13, 12-01, 12-02, 12-03, 12-04, 12-05, 12-06, 13-01, 14-01, 16-01, 16-02, 17-01, 17-02, 18-01, 18-02, 19-01, 19-02, 19-03, 1-01, 1-02, 2-01, 3-01, 3-22, 3-23, 3-24, 6-01, 6-02, 7-01, 7-02, 7-04, 7-05 and 15-01.

Processes for the preparation of compounds of formula (I') are also part of the invention as well as intermediates used in these processes.

Thus, compounds of formula (I') can be obtained by coupling a compound of formula (II) with a compound of formula (III):

Scheme 1

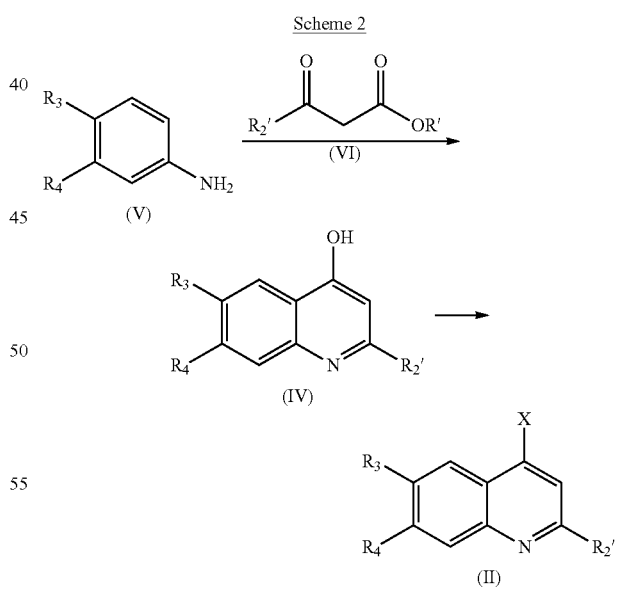

wherein $R_1$, $R_2'$, $R_3$ and $R_4$ are as previously defined, and X is a halogen atom, preferably chloro. This conversion may be carried out in the presence of a palladium catalyst, such as e.g. Tris(dibenzylideneacetone)dipalladium(0) ($Pd_2(dba)_3$), an organophosphorus compound, such as e.g. Biphenyl-2-yl-dicyclohexyl-phosphane, (2,2'-bis(diphenylphosphino)-1, 1'-binaphthyl) (BINAP) or 4,5-Bis(diphenylphosphino)-9,9-dimethylxanthene (Xantphos), and a base, such as e.g. $Cs_2CO_3$, sodium tert-butoxide or $K_3PO_4$. The reaction is performed in a suitable solvent, such as e.g. dimethyl ether (DME), toluene or dioxane, at a suitable temperature, preferably heating.

A compound of formula (II) can be obtained by reacting an aniline of formula (V) with a compound of formula (VI) and subsequently converting the obtained compound of formula (IV) into a compound of formula (II) as shown in the scheme below:

Scheme 2 wherein X, $R_2'$, $R_3$ and $R_4$ are as previously defined, and R' represents ($C_1$-$C_6$)alkyl. The first conversion may be carried out in the presence of a halogenating agent, such as e.g. $POCl_3$, at a suitable temperature, preferably heating, and the second conversion may be performed in a suitable solvent, such as e.g. polyphosphoric acid (PPA), at a suitable temperature, preferably heating.

Compounds of formula (I') wherein $R_2'$ represents $OR^a$ (i.e. compounds of formula (I'a)), $NR^aR^c$ (i.e. compounds of formula (I'b)), $Cy^6$ (i.e. compounds of formula (I'c)), or $Z^8$ (i.e. compounds of formula (I'd)) can be obtained by reacting a compound of formula (VII) with a compound of formula (VIII), (IX), (X) or (XI), respectively, as shown in the scheme below, and subsequently converting the resulting compound of formula (IIa), (IIb), (IIc) or (IId) into the respective compounds of formula (I') as described above:

palladium catalyst, such as e.g. Tetrakis(triphenyl-phosphine)palladium(0) $(Pd(PPh_3)_4)$ and a base, such as e.g. $K_2CO_3$, in a suitable solvent, such as e.g. dioxane optionally mixed with water, at a suitable temperature, preferably heating. Alternatively, this conversion may be carried out with a stannate derivative in the presence of a palladium catalyst, such as e.g. Bis(triphenylphosphine)palladium(II) dichloride $(Pd(PPh_3)Cl_2)$ in a suitable solvent, such as e.g.

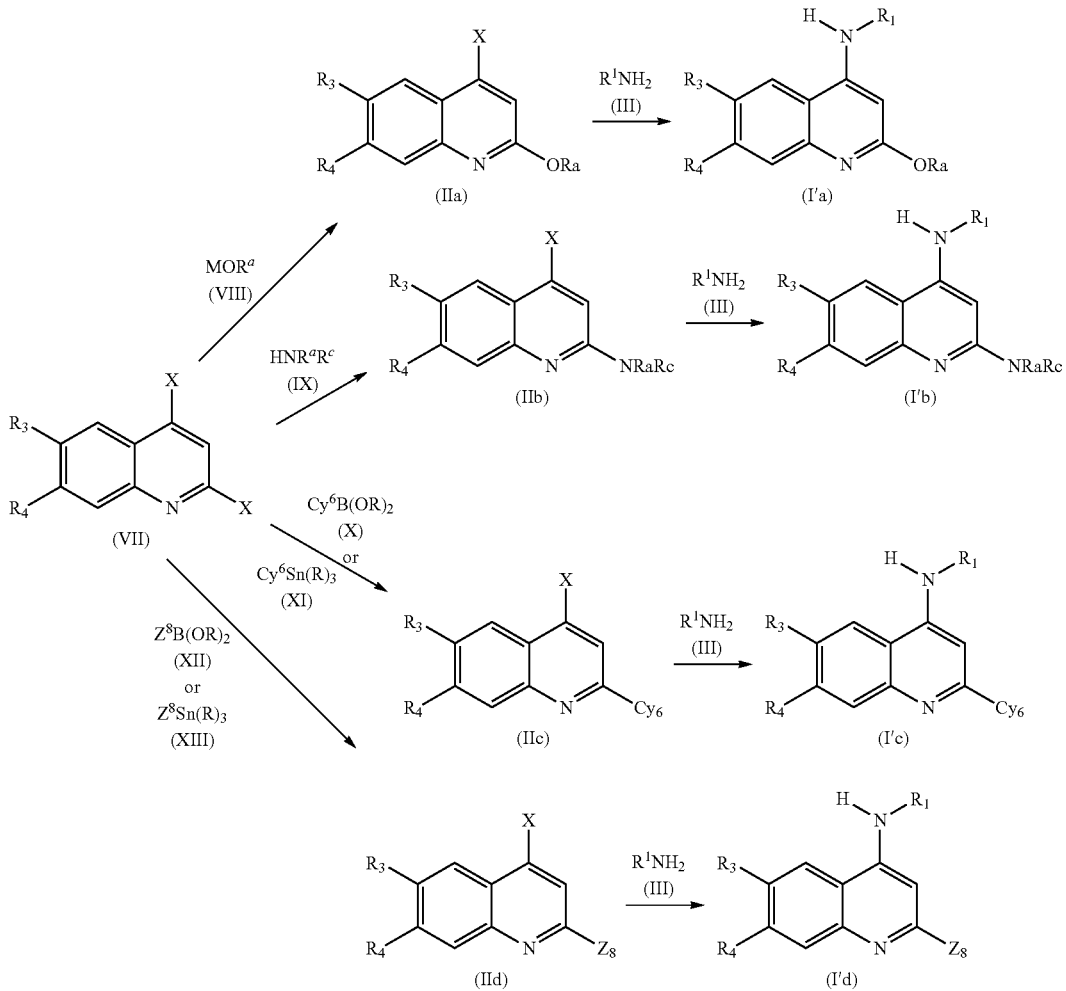

Scheme 3 wherein $R_1$, $R^a$, $R^c$, $Cy^6$, $Z^8$, $R_3$ and $R_4$ are as previously defined, X is a halogen atom, preferably chloro, M is an alkaline metal, preferably sodium, and R is H, $(C_1-C_6)$alkyl or in the case of a boronic derivative, two R groups together with the B atom to which they are attached may form a cycle.

In the case of a compound of formula (I'a) the first conversion may be carried out without solvent, at a suitable temperature, preferably room temperature. In the case of a compound of formula (I'b) the first conversion may be carried out in the same conditions as the ones described above for the conversion of a compound of formula (II) into a compound of formula (I'). In the case of a compound of formula (I'c) or formula (I'd) the first conversion may be carried out with a boronic derivative in the presence of a dimethylformamide, at a suitable temperature, preferably heating.

The compound of formula (VII) can be obtained from a compound of formula (XIII), which is reduced to an aniline of formula (V) and subsequently reacted with a compound of formula (XIV) to give the compound of formula (VII):

Scheme 4

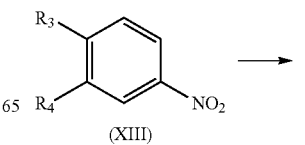

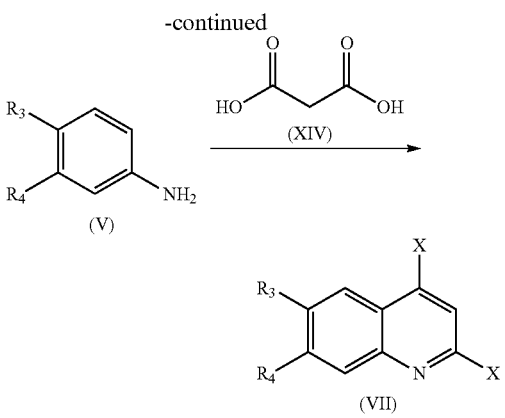

The reduction of the compound of formula (XIII) may be carried out by hydrogenation whereas the conversion of a compound of formula (V) into a compound of formula (VII) is carried out in the presence of a halogenating agent, such as e.g. POCl$_3$, at a suitable temperature, preferably heating.

Alternatively, the reactions described above can be carried out in a different order. Compounds of formula (I') may be converted into other compounds of formula (I'). The compounds of formulas (III), (VI), (VIII) to (XIV) are commercially available or can be obtained by conventional synthetic processes.

The present invention also relates to a pharmaceutical or veterinary composition comprising an effective amount of a compound of formula (I) as defined above, or a pharmaceutically or veterinary acceptable salt thereof, or any stereoisomer either of the compound of formula (I) or of its pharmaceutically or veterinary acceptable salt, together with pharmaceutically or veterinary acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The specific dose of the compound of the invention to obtain a therapeutic benefit may vary depending on the particular circumstances of the individual patient including, among others, the size, weight, age and sex of the patient, the nature and stage of the disease, the aggressiveness of the disease, and the route of administration. For example, a dose of from about 0.01 to about 300 mg/kg may be used.

The expression "pharmaceutically or veterinary acceptable excipients or carriers" refers to pharmaceutically or veterinary acceptable materials, compositions or vehicles. Each component must be pharmaceutically or veterinary acceptable in the sense of being compatible with the other ingredients of the pharmaceutical or veterinary composition. It must also be suitable for use in contact with the tissue or organ of humans and animals without excessive toxicity, irritation, allergic response, immunogenicity or other problems or complications commensurate with a reasonable benefit/risk ratio.

The election of the pharmaceutical or veterinary formulation will depend upon the nature of the active compound and its route of administration. Any route of administration may be used, for example oral, parenteral and topical administration.

For example, the pharmaceutical or veterinary composition may be formulated for oral administration and may contain one or more physiologically compatible carriers or excipients, in solid or liquid form. These preparations may contain conventional ingredients such as binding agents, fillers, lubricants, and acceptable wetting agents.

The pharmaceutical or veterinary composition may be formulated for parenteral administration in combination with conventional injectable liquid carriers, such as water or suitable alcohols. Conventional pharmaceutical or veterinary excipients for injection, such as stabilizing agents, solubilizing agents, and buffers, may be included in such compositions. These pharmaceutical or veterinary compositions may be injected intramuscularly, intraperitoneally, or intravenously.

The pharmaceutical composition may be formulated for topical administration. Formulations include creams, lotions, gels, powders, solutions and patches wherein the compound is dispersed or dissolved in suitable excipients.

The pharmaceutical compositions may be in any form, including, among others, tablets, pellets, capsules, aqueous or oily solutions, suspensions, emulsions, or dry powdered forms suitable for reconstitution with water or other suitable liquid medium before use, for immediate or retarded release.

The appropriate excipients and/or carriers, and their amounts, can readily be determined by those skilled in the art according to the type of formulation being prepared.

As mentioned above, the compounds of the invention having the quinoline core and being substituted as previously defined, in particular by the $R_2'$ group at position 2, the amino group at position 4, and the $R_4$ group at position 7, are dual inhibitors of G9a and DNMTs. For the purposes of the invention, this means that the compounds as defined above are capable of inhibiting G9a with an $IC_{50}$ value$\leq 10$ µM, preferably $\leq 1$ µM, more preferably $\leq 500$ nM, and also capable of inhibiting one or more DNMTs selected from the group consisting of DNMT1, DNMT3A and DNMT3B with an $IC_{50}$ value$\leq 10$ µM, preferably $\leq 1$ µM, more preferably $\leq 500$ nM, when the inhibition of G9a and DNMTs is measured in enzymatic assays as the ones described in the present invention.

As dual inhibitors of G9a and DNMT, the compounds of the invention may be used in the treatment and/or prevention of cancer.

For the purposes of the invention, the term "treatment" of the disease refers to stopping or delaying of the disease progress, when the drug is used in the subject exhibiting symptoms of disease onset. The term "prevention" refers to stopping or delaying of symptoms of disease onset, when the drug is used in the subject exhibiting no symptoms of disease onset but having high risk of disease onset.

In one embodiment, optionally in combination with one or more features of the various embodiments described above or below, the cancer is selected from the group consisting of a hematogical cancer and a solid tumor. More particularly, the hematogical cancer is selected from the group consisting of leukemia, lymphoma and multiple myeloma; and the solid tumor is selected from the group consisting of bladder cancer, breast cancer, cervical cancer, colorectal cancer, glioblastoma, hepatocarcinoma, lung cancer, melanoma, pancreatic cancer, prostate cancer and renal cancer.

Compounds of formula (I') may be effective as synergistically combined with other cancer treating agents. Thus, in one embodiment, optionally in combination with one or more features of the various embodiments described above or below, the invention relates to the compound of formula (I') or a pharmaceutically or veterinary acceptable salt thereof, or any stereoisomer or mixtures thereof, either of the compound of formula (I') or of any of its pharmaceutically or veterinary acceptable salts, for use in the treatment and/or prevention of cancer mediated by the inhibition of histone methyltransferase G9a and of one or more DNMTs selected from the group consisting of DNMT1, DNMT3A and DNMT3B, wherein the treatment comprises administering to a subject simultaneously, sequentially or separately the compound of formula (I') or a pharmaceutically or veterinary acceptable salt thereof, or any stereoisomer or mixtures thereof, either of the compound of formula (I') or of any of its pharmaceutically or veterinary acceptable salts, and one or more other cancer treating compounds.

Alternatively, the above embodiment can be formulated as the use of a compound of formula (I'), or a pharmaceutically or veterinary acceptable salt thereof, or any stereoisomer or mixtures thereof, either of the compound of formula (I') or of any of its pharmaceutically or veterinary acceptable salts, for the manufacture of a medicament for the treatment and/or prevention of cancer; wherein the treatment comprises administering to a subject simultaneously, sequentially or separately the compound of formula (I') or a pharmaceutically or veterinary acceptable salt thereof, or any stereoisomer or mixtures thereof, either of the compound of formula (I') or of any of its pharmaceutically or veterinary acceptable salts, and one or more other cancer treating compounds.

Alternatively, the above embodiment can be formulated as a method for the treatment and/or prevention of cancer, comprising administering an effective amount of the previously defined compound of formula (I'), or a pharmaceutically or veterinary acceptable salt thereof, or any stereoisomer or mixtures thereof, either of the compound of formula (I') or of any of its pharmaceutically or veterinary acceptable salts, and one or more pharmaceutically or veterinary acceptable excipients or carriers, in a subject in need thereof, including a human; wherein the treatment comprises administering to a subject simultaneously, sequentially or separately the compound of formula (I') or a pharmaceutically or veterinary acceptable salt thereof, or any stereoisomer or mixtures thereof, either of the compound of formula (I') or of any of its pharmaceutically or veterinary acceptable salts, and one or more other cancer treating compounds.

Examples of other cancer treating compounds include, without limitation:
Proteosome inhibitors; e.g. Bortezomib, Calzirfomid, etc.
Immune modulators (IMID); e.g. Revlimid, Talidomide, Pomalidomide, Lenalidomide, etc.
Monoclonal antibodies; e.g. Rituximab, SAR650984, Daratumumab, Ipilimumab, Nivolumab, Cetuximab, Panitumumab, Bevacizumab, Pertuzumab, Aflibercept, Ramucirumab, Herceptin, Lambrolizumab, etc.
Kinase inhibitors; e.g. Imatinib, Ibrutinib, Erlotinib, Sunitinib, Sorafenib, Lapatinib, Regorafenib, Pazopanib, Axitinib, Cabozantinib, Afatinib, Gefitinib, Dacomitinib, Crizotinib, Ceritinib, Dabrafenib, etc.
Histone deacetylase inhibitors; e.g. Vorinostat, Panobinostat, Rocilinostat, etc.

In another embodiment, optionally in combination with one or more features of the various embodiments described above or below, the cancer is selected from the group consisting of Acute Lymphocytic Leukemia (ALL), Diffuse Large B-cell lymphoma (DLBCL), bladder cancer, breast cancer, cervical cancer, colorectal cancer, glioblastoma, hepatocarcinoma, melanoma, pancreatic cancer, prostate cancer, renal cancer, small-cell lung cancer, non small-cell lung cancer, acute myeloid leukemia, mantle cell lymphoma and multiple myeloma.

Further, the compounds of the invention are also useful in the generation of induced pluripotent stem cells. Thus, this aspect relates to the use of a compound of formula (I') as defined above, or a pharmaceutically or veterinary acceptable salt thereof, or any stereoisomer or mixtures thereof, either of the compound of formula (I') or of any of its pharmaceutically or veterinary acceptable salts for generating induced pluripotent stem cells; and may also be formulated as a method for generating induced pluripotent stem cells, the method comprising the step of culturing isolated cells together with one or more transcription factors and a compound of formula (I'), or a pharmaceutically or veterinary acceptable salt thereof, or any stereoisomer or mixtures thereof, either of the compound of formula (I') or of any of its pharmaceutically or veterinary acceptable salts.

The skilled in the art taking into account the type of cell to be reprogrammed would know how to adjust the culturing conditions, the transcription factors, and the appropriate reprogramming system for carrying out the above method. Generally, one or more transcription factors may be used, such as OCT4 (O), SOX2 (S), KLF4 (K) and cMYC (M) preferably 2 or 4 transcription factors.

In another embodiment, optionally in combination with one or more features of the various embodiments described above or below, the isolated cells are isolated fibroblasts.

Throughout the description and claims the word "comprise" and variations of thereof, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

General Procedure for Preparative HPLC Purification Method:

The HPLC measurement was performed using Gilson 281 from 233 pump (binary), an autosampler, and a UV detector. The fractions was detected by LC-MS. The MS detector was configured with an electrospray ionization source. The source temperature was maintained at 300-350° C.

HPLC Methods (Purification Methods):

Method 1: Reverse phase HPLC was carried out on Luna $C_{18}$ (100×30 mm; 4 um). Solvent A: water with 0.075% trifluoroacetic acid; Solvent B: acetonitrile with 0.075% trifluoroacetic acid. Gradient: At room temperature, 20% of B to 40% of B within 6 min at 25 mL/min; then 40% B at 25 mL/min over 2 min, UV detector.

Method 2: Reversed phase HPLC was carried out on luna (100×30 mm; 5 um). Solvent A: water with 0.075% TFA; Solvent B: acetonitrile with 0.075% TFA. Gradient: At 25° C., 13% of B to 33% of B within 10 min; then 33% B over 4 min, Flow rate: 25 mL/min. PDA.

Method 3: Reverse phase HPLC was carried out on Luna $C_{18}$ (100×30 mm; 4 um). Solvent A: water with 0.075% trifluoroacetic acid; Solvent B: acetonitrile with 0.075% trifluoroacetic acid. Gradient: At room temperature, 20% of B to 45% of B within 6 min at 25 mL/min; then 40% B at 25 mL/min over 3 min, UV detector.

Method 4: Reversed phase HPLC was carried out on luna (100×30 mm; 5 um). Solvent A: water with 0.075% TFA;

Solvent B: acetonitrile with 0.075% TFA. Gradient: At 25° C., 10% of B to 30% of B within 10 min; then 30% B over 5 min, Flow rate: 20 mL/min. PDA.

Method 5: Purified by prep-HPLC Reversed phase HPLC was carried out on luna (100×30 mm; 5 um). Solvent A: water with 0.075% TFA; Solvent B: acetonitrile with 0.075% TFA. Gradient: At 25° C., 3% of B to 23% of B within 6 min; then 23% B over 4 min, Flow rate: 25 ml/min. PDA.

Method 6: Reverse phase HPLC was carried out on Luna $C_{18}$ (100×30 mm; 4 um). Solvent A: water with 0.075% TFA; Solvent B: acetonitrile with 0.075% TFA. Gradient: At 25° C., 25% of B to 45% of B within 6 min at 20 mL/min; then 40% B at 25 mL/min over 3 min, UV detector.

The following abbreviations have been used in the examples:
HPLC: High-performance liquid chromatography; TLC: thin layer chromatography; MW: microwaves; calc.: calculated; conc.: concentrated; RT: room temperature; Rt: Retention time; Boc: tert-butoxycarbonyl; DMAP: 4-Dimethyl-aminopyridine; DCM: dichloromethane; DIAD: Diisopropyl azodicarboxylate; DMF: dimethylformamide; DMSO: dimethylsulfoxide; EA: ethyl acetate; EDC.HCl: 1-ethyl-3-(3-dimethylamino-propyl)carbodiimide hydrochloride; eq: equivalent; ESI-MS: electrospray ionization mass spectrometry; $Et_3N$: triethylamine; HOBt: Hydroxy-benzo-triazole; LDA: Lithium diisopropylamide; NMM: N-methyl morpholine; PE: petrol ether; TFA: trifluoroacetic acid; THF: tetrahydrofuran; THP: tetrahydropyran; DEAD: diethylazodicarboxylate; BINAP: 2,2'bis(diphenylphospinio)-1,1'-binaphthyl; X-Phos: 2-Dicyclohexylphosphino-2',4',6'-triisopropylbiphenyl; PPA: polyphosphoric acid; DME: 1,2-dimethoxyethane.

Preparation of reagent R-05b: tributyl-(5-ethyl-2-furyl)stannane

To a solution of commercially available 2-ethylfuran (1.92 g, 20 mmol) in THF (100 mL), n-BuLi (8.8 mL, 22 mmol) was added slowly at −78° C., then stirred at −25° C. for 2 h. Then, tributylchlorostannane (6.89 g, 20 mol) was added at −78° C. The reaction mixture was stirred at RT overnight. The mixture was quenched with water and extracted with AcOEt. The organic layer was concentrated under vacuo to give the desired reagent R-05b (1 g, 13%). ESI-MS (M+1): 387.1 calc. for $C_{18}H_{34}OSn$: 386.1.

Synthetic Route 1

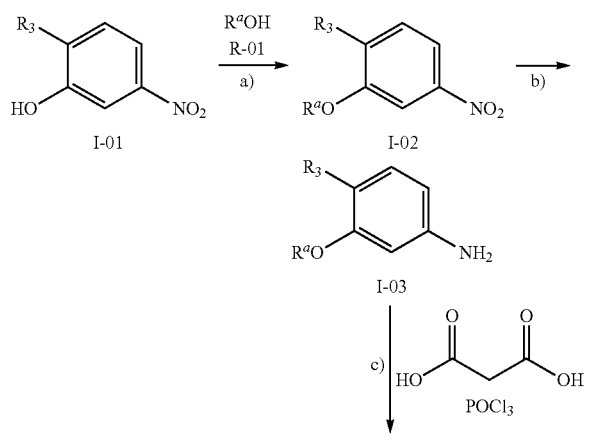

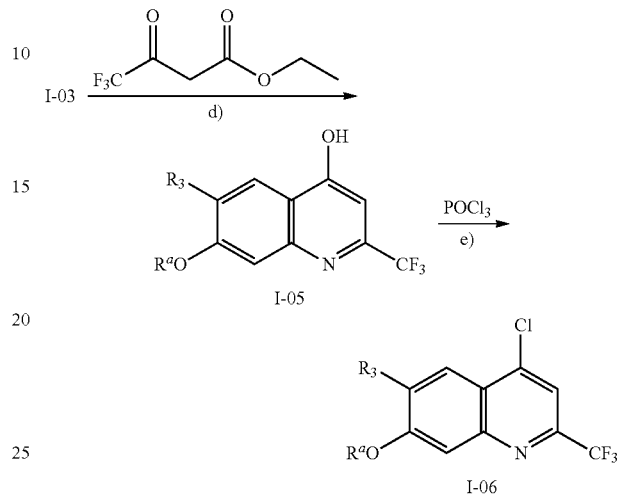

Conditions: a) R-01 (1.3 eq), PPh₃ (2 eq.), DEAD (2 eq) in THF, RT for 1 h; b) Pd/C in MeOH, H₂ atmosphere, RT for 3 h; c) Malonic acid (1.1 eq) in POCl₃, RT. for 4 h then overnight at 90° C.; d) ethyl 4,4,4-trifluoro-3-oxobutanoate (1 eq.) in PPA at 120° C. for 1 h; e) POCl₃, 110° C. for 2 h.

In the scheme above $R_3$ is H, Cl, $OCF_3$ or $O(C_1-C_6)$alkyl and $R^a$ is a hydrocarbon chain, which contains nitrogen and/or oxygen atoms.

Preparation of Intermediate I-02a: 1-[3-(2-methoxy-5-nitro-phenoxy)propyl]-pyrrolidine To a solution of commercially available 2-methoxy-5-nitro-phenol: I-01a (19.6 g, 0.12 mol) in THF (200 mL), $PPh_3$ (61 g, 0.23 mol), commercially available 3-pyrrolidin-1-yl-propan-1-ol: R-01a (15 g, 0.16 mol) and DEAD (40 g. 0.23 mol) were added at 0° C., the solution was stirred at RT for 5 h. The reaction mixture was concentrated and extracted with AcOEt. The combined organic layers were washed with brine, dried over anhydrous $Na_2SO_4$, filtered and concentrated to give the crude product which was purified by column chromatography (eluent gradient PE:EA=1:0 to 3:1) to give intermediate I-02a (14 g, 44% yield) as a yellow solid. ESI-MS (M+1): 281 calc. for $C_{14}H_{20}N_2O_4$: 280.1.

Preparation of Intermediate I-02b: 1-[3-(3-nitrophenoxy)propyl]pyrrolidine

Intermediate I-02b was obtained in an analogous manner to I-02a starting from commercially available 3-nitrophenol: I-01b. 37% yield, ESI-MS (M+1): 251 calc. for $C_{13}H_{18}N_2O_3$: 250.1.

Preparation of Intermediate I-03a: 4-methoxy-3-(3-pyrrolidin-1-ylpropoxy)aniline To a solution of intermediate I-02a (14 g, 0.05 mol) in MeOH (200 mL) was added Pd/C (3 g). The solution was stirred at RT for 3 h, in $H_2$ atmosphere. The solution was filtrated and concentrated to give intermediate I-03a (12 g, 96%) as a yellow oil. ESI-MS (M+1): 251 calc. for $C_{14}H_{22}N_2O_2$: 250.1.

Preparation of Intermediate I-03b: 3-(3-pyrrolidin-1-ylpropoxy)aniline

Intermediate I-03b was obtained in an analogous manner to I-03a starting from intermediate I-02b. 96% yield, ESI-MS (M+1): 221 calc. for $C_{13}H_{20}N_2O$: 220.1.

Preparation of Intermediate I-04a: 2,4-dichloro-6-methoxy-7-(3-pyrrolidin-1-ylpropoxy)quinolone To a solution of intermediate I-03a (12.4 g, 0.049 mol) in POCl3 (200 mL) was added commercially available malonic acid (5.67, 0.055 mol) at RT After stirring at RT for 4 h, the solution was heated at 90° C. overnight; the solution was concentrated and poured into ice-water, then extracted with AcOEt. The combined organic layers were washed with brine, dried over anhydrous $Na_2SO_4$, filtered and concentrated to give intermediate I-04a (10 g, 66%) as a pale yellow solid. ESI-MS (M+1): 355 calc. for $C_{17}H_{20}Cl_2N_2O_2$: 354.1.

Preparation of Intermediate I-04b: 2,4-dichloro-7-(3-pyrrolidin-1-ylpropoxy)quinolone Intermediate I-04b was obtained in an analogous manner to I-04a starting from intermediate I-03b. 34% yield, ESI-MS (M+1): 325 calc. for $C_{16}H_{18}Cl_2N_2O$: 324.1.

Preparation of Intermediate I-04c: 2,4-dichloro-6,7-dimethoxy-quinoline 3,4-dimethoxyaniline Intermediate I-04c was obtained in an analogous manner to I-04a starting from commercially available 3,4-dimethoxyaniline: I-03c. 59% yield, ESI-MS (M+1): 258 calc. for 59%) as a pale yellow solid. ESI-MS (M+1): 258 calc. for $C_{11}H_9Cl_2NO_2$: 257.0.

Following the same synthetic route for intermediate I-04a starting from compound I-01 (3 steps) indicated in the table below and using the reagents also indicated, the following intermediates were obtained:

| Intermediate | [M + 1]+ | Starting material/Reagent |
|---|---|---|
| I-04d | 359.2 | 2-chloro-5-nitro-phenol (I-01c)/ 3-pyrrolidin-1-yl-propan-1-ol (R-01a) |
| I-04e | 409.1 | 5-nitro-2-(trifluoromethoxy)phenol (I-01d)/ 3-pyrrolidin-1-yl-propan-1-ol (R-01a) |
| I-04f | 381.2 | 2-methoxy-5-nitro-phenol (I-01a)/3-(5-azaspiro[2.4]heptan-5-yl)propan-1-ol (R-01b) |
| I-04g | 369.2 | 2-methoxy-5-nitro-phenol (I-01a)/ 3-(1-piperidyl)propan-1-ol (R-01c) |
| I-04h | 371.2 | 2-methoxy-5-nitro-phenol (I-01a)/ 3-morpholinopropan-1-ol (R-01d) |
| I-04i | 329.2 | 2-methoxy-5-nitro-phenol (I-01a)/ 3-(dimethylamino)propan-1-ol (R-01e) |

Preparation of Intermediate I-05a: 6-methoxy-7-(3-pyrrolidin-1-ylpropoxy)-2-(trifluoromethyl)quinolin-4-ol PPA (50 mL) was heated at 80° C. with stirring in a round-bottomed flask, then intermediate I-03a (5 g, 0.02 mol) was added at 80-100° C. After addition, commercially available ethyl 4,4,4-trifluoro-3-oxobutanoate (3.68 g, 0.02 mol) was then added into the reaction mixture over 15-20 min. The reaction mixture was stirred vigorously at 120° C. for 12 hours. Then, the mixture was poured into the ice-water and adjusted pH to 8 by addition of $Na_2CO_3$, then concentrated under vacuo and extracted with DCM:MeOH (3:1). The combined organic layer was concentrated under vacuo to give intermediate I-05a (2.5 g, 32%). ESI-MS (M+1): 371 calc. for $C_{18}H_{21}F_3N_2O_3$: 370.1.

Preparation of Intermediate I-06a: 4-chloro-6-methoxy-7-(3-pyrrolidin-1-ylpropoxy)-2-(trifluoromethyl)quinolone Intermediate I-05a (370 mg, 1 mmol) was dissolved in $POCl_3$ (30 mL), then stirred at 110° C. for 2 hours. The reaction mixture was concentrated under vacuo, then quenched with ice-water and extracted with AcOEt, the organic phase was dried with $Na_2SO_4$, filtered and concentrated under vacuo to give the desired intermediate I-06a (200 mg). ESI-MS (M+1): 389 calc. for $C_{18}H_{20}ClF_3N_2O_2$: 388.1.

Synthetic Route 2

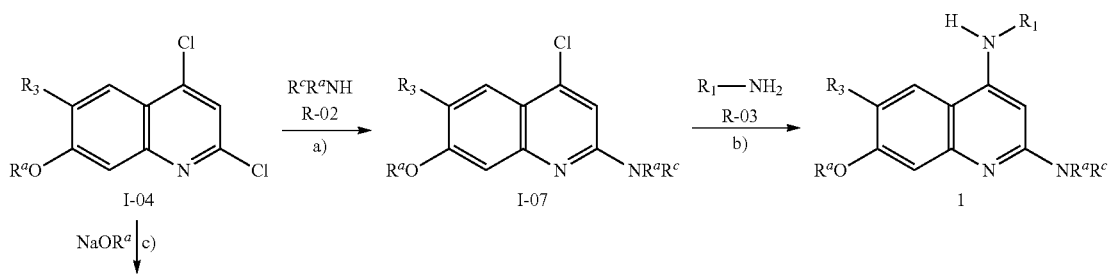

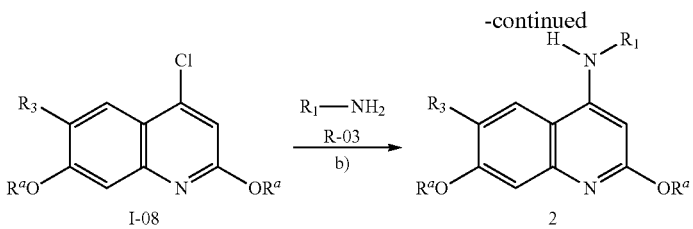

Conditions: a) R-02 (1.5 eq), Pd₂(dba)₃ (0.1 eq), Cs₂CO₃ (2 eq.), BINAP (0.1 eq), in dioxane, overnight at 110° C.; b) R-03 (5 eq), Pd₂(dba)₃ (0.2 eq), Cs₂CO₃ (5 eq.) in dioxane, mw, 1 h. at 120° C.; c) NaOR (25%), overnight at RT.

In the scheme above $R_1$ is a cycle (Cy) or a hydrocarbon chain, which optionally contains nitrogen, oxygen and/or fluor atoms, were Cy is an aryl, heteroaryl, carbocycle or heterocyclic ring; $R_3$ is $O(C_1-C_6)$alkyl; $R^a$ and $R^c$ are independently a hydrocarbon chain, which optionally contains nitrogen atoms.

Preparation of Intermediate I-07a: 4-chloro-6,7-dimethoxy-2-(4-methyl-piperazin-1-yl)quinolone To a solution of intermediate I-04c (3 g, 0.01 mol) in dioxane (30 mL) was added Cs₂CO₃ (6.52 g, 0.02 mol), BINAP (0.62 g, 0.001 mol), Pd₂(dba)₃ (0.92 g, 0.001 mol) and R-02a: 1-Methyl-piperazine (3.5 g, 0.035 mol). The mixture was heated at 110° C. overnight. The solution was concentrated and extracted with AcOEt. The combined organic layers were washed with brine, dried over anhydrous Na₂SO₄, filtered and concentrated to give the crude product which was purified by prep-HPLC (General procedure, Method 1), to give intermediate I-07a (1 g, 27%) as a yellow solid. ESI-MS (M+1): 322 calc. for $C_{16}H_{20}ClN_3O_2$: 321.1.

Preparation of Intermediate I-07b: 4-chloro-6-methoxy-2-(4-methylpiperazin-1-yl)-7-(3-pyrrolidin-1-ylpropoxy)quinoline Intermediate I-07b was obtained in an analogous manner to I-07a starting from intermediate I-04a. 18% yield, ESI-MS (M+1): 419 calc. for $C_{22}H_{31}ClN_4O_2$: 418.2.

Preparation of Intermediate I-08a: 4-chloro-2,6-dimethoxy-7-(3-pyrrolidin-1-ylpropoxy)quinoline Intermediate I-04a (1.5 g, 4.24 mmol) was dissolved in NaOMe (25 mL, 25%), then stirred at RT overnight. The reaction mixture was quenched by adding water. The organic phase was separated, concentrated to give the crude product which was purified by Pre-HPLC (General procedure, Method 1), to give the desired intermediate I-08a (0.5 g, 34%) ESI-MS (M+1): 351 calc. for $C_{18}H_{23}ClN_2O_3$: 350.1.

Preparation of compound 1-01: 6,7-dimethoxy-2-(4-methylpiperazin-1-yl)-N-(1-methyl-4-piperidyl)quinolin-4-amine; 2,2,2-trifluoroacetic acid To a solution of intermediate I-07a (2.5 g, 7.8 mmol) in dioxane (50 mL) was added Cs₂CO₃ (5.08 g, 5.6 mmol), BINAP (0.48 g, 0.78 mol), Pd₂(dba)₃ (0.7 g, 0.78 mol) and R-03a: 1-Methyl-piperidin-4-ylamine (1.77 g, 15.6 mmol). The mixture was heated at 110° C. overnight. The solution was concentrated and extracted with AcOEt. The combined organic layers were washed with brine, dried over anhydrous Na₂SO₄, filtered and concentrated to give the crude product which was purified by prep-HPLC (General procedure, Method 1) to give compound I-01 as TFA salt (0.02 g, 1%). ESI-MS (M+1): 400.3 calc. for $C_{22}H_{33}N_5O_2 \cdot C_2HF_3O_2$: 513.2; Rt is 1.79.

Following the same synthetic route for compound I-01 using the same reagents and intermediates unless otherwise indicated in the table below, the following compounds were obtained:

| Example | Rt (min) | [M + 1]⁺ | HPLC Method | Intermediate |
| --- | --- | --- | --- | --- |
| 1-02 | 2.14 | 497 | 1 | I-07b |
| 2-01 | 1.75 | 429 | 1 | I-08a |

Synthetic Route 3a

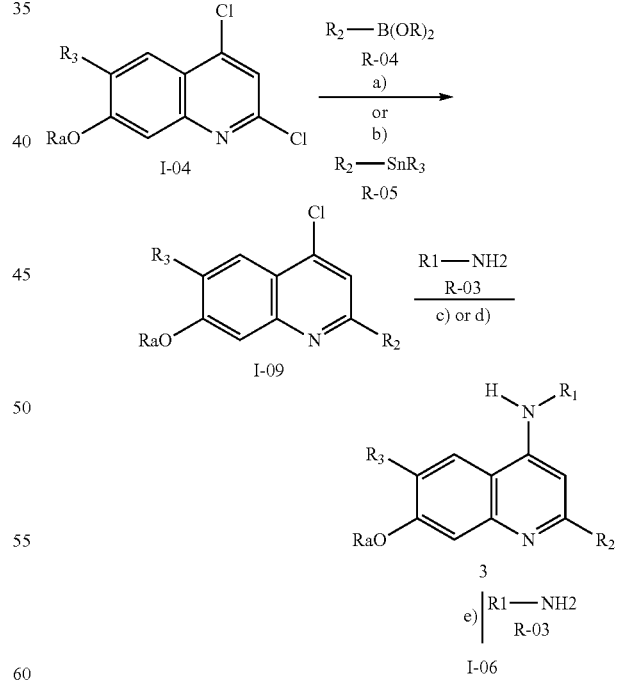

Conditions: a) R-04 (1.06 eq), Pd(Ph₃)₄ (0.1 eq), K₂CO₃ (2 eq.) in dioxane, overnight at 120° C. or mw 2 h at 110° C.; b) R-05 (1 eq), Pd(PPh₃)Cl₂ (0.1 eq) in DMF, 12 h at 110° C.; c) R-03 (5 eq), Pd₂(dba)₃ (0.15 eq), Biphenyl-2-yl-dicyclohexyl-phosphane (0.15 eq), K₃PO₄ (3 eq.) in DME, mw, 3 h at 110° C.; d) R-03 (3 eq), Pd₂(dba)₃ (0.3 eq), Xantphos (0.3 eq), NaOBu-t(3 eq) in toluene, mw, 3 h at 100° C.; e) R-03 (3 eq), Pd₂(dba)₃ (0.3 eq), BINAP (0.3 eq), Cs₂CO₃ (3 eq) in dioxane, mw, 3 h at 110° C.

In the scheme above R$_1$ is cycle (Cy) or a hydrocarbon chain, which optionally contains nitrogen, oxygen and/or fluor atoms, were Cy is an aryl, heteroaryl, carbocycle or heterocyclic ring; R$_2$ is aryl or heteroaryl; R$_3$ is H, Cl, OCF$_3$ or O(C$_1$-C$_6$)alkyl; R$^a$ is a hydrocarbon chain, which contains nitrogen and/or oxygen atoms.

Preparation of Intermediate I-09a:
4-chloro-6,7-dimethoxy-2-methyl-quinoline

To a solution of intermediate I-04c (4 g, 0.016 mol) in dioxane (60 mL) was added methylboronic acid (R-04a) (1.02 g, 0.017 mol), K$_2$CO$_3$ (4.3 g, 0.0312 mol), Pd(Ph$_3$)$_4$ (1.8 g, 0.0016 mol), the solution was heated to 120° C. overnight. The reaction mixture was concentrated and extracted with AcOEt. The combined organic layers were washed with brine, dried over anhydrous Na$_2$SO$_4$, filtered and concentrated to give the crude product which was purified by column chromatography (eluent gradient PE:EA=1:0 to 3:1) to give intermediate I-09a (0.7 g, 18% yield) as a yellow solid. ESI-MS (M+1): 238 calc. for Cl$_2$H$_{12}$ClNO$_2$: 237.0.

Following the same synthetic route for intermediate I-09a and using the same reagents and intermediates unless otherwise indicated in the table below, the following intermediates were obtained:

| Intermediate I-09 | Yield | [M + 1]+ | Intermediate/reagent |
|---|---|---|---|
| I-09b | 41% | 304 | I-04c/4,4,5,5-tetramethyl-2-(5-methyl-2-furyl)-1,3,2-dioxaborolane (R-04b) |
| I-09c | 88% | 371 | I-04b/4,4,5,5-tetramethyl-2-(5-methyl-2-furyl)-1,3,2-dioxaborolane (R-04b) |
| I-09d | 31% | 401 | I-04a/4,4,5,5-tetramethyl-2-(5-methyl-2-furyl)-1,3,2-dioxaborolane (R-04b) |
| I-09e | 20% | 335 | I-04a/methylboronic acid (R-04a) |
| I-09f | 73% | 437 | I-04a/benzofuran-2-ylboronic acid (R-04c) |
| I-09g | 39% | 401 | I-04a/1-methyl-5-(4,4,5,5-tetramethyl-1,3,2-dioxaborolan-2-yl)pyrazole (R-04d) |
| I-09h | 31% | 387 | I-04a/3-furylboronic acid (R-04e) |
| I-09i | 53% | 437 | I-04a/benzofuran-5-ylboronic acid (R-04f) |
| I-09j | 30% | 397 | I-04a/phenylboronic acid (R-04g) |
| I-09k | 50% | 398 | I-04a/3-pyridylboronic acid (R-04h) |
| I-09l | 37% | 400.2 | I-04a/2-methyl-5-(4,4,5,5-tetramethyl-1,3,2-dioxaborolan-2-yl)-1H-pyrrole (R-04k) |
| I-09m | 32% | 463 | I-04a/4,4,5,5-tetramethyl-2-(5-phenyl-2-furyl)-1,3,2-dioxaborolane (R-04l) |
| I-09n | 32% | 401.2 | I-04a/1-methyl-3-(4,4,5,5-tetramethyl-1,3,2-dioxaborolan-2-yl)pyrazole (R-04m) |
| I-09o | 48% | 411 | I-04a/o-tolylboronic acid (R-04n) |
| I-09p | 43% | 415 | I-04a/2-(2,5-dimethyl-3-furyl)-4,4,5,5-tetramethyl-1,3,2-dioxaborolane (R-04o) |
| I-09q | 51% | 417 | I-04a/4,4,5,5-tetramethyl-2-(5-methyl-2-thienyl)-1,3,2-dioxaborolane (R-04p) |
| I-09r | 50% | 414.1 | I-04a/4-(4,4,5,5-tetramethyl-1,3,2-dioxaborolan-2-yl)-1H-pyridin-2-one (R-04q) |
| I-09u | 49% | 405 | I-04d/4,4,5,5-tetramethyl-2-(5-methyl-2-furyl)-1,3,2-dioxaborolane (R-04b) |
| I-09v | 81% | 455.2 | I-04e/4,4,5,5-tetramethyl-2-(5-methyl-2-furyl)-1,3,2-dioxaborolane (R-04b) |
| I-09w | 90% | 441.2 | I-04f/4,4,5,5-tetramethyl-2-(5-ethyl-2-furyl)-1,3,2-dioxaborolane (R-04r) |
| I-09x | 95% | 429.3 | I-04g/4,4,5,5-tetramethyl-2-(5-ethyl-2-furyl)-1,3,2-dioxaborolane (R-04r) |
| I-09y | 82% | 431.3 | I-04h/4,4,5,5-tetramethyl-2-(5-ethyl-2-furyl)-1,3,2-dioxaborolane (R-04r) |
| I-09z | 85% | 389.3 | I-04i/4,4,5,5-tetramethyl-2-(5-ethyl-2-furyl)-1,3,2-dioxaborolane (R-04r) |

Preparation of Intermediate I-09s: 4-chloro-2-(2-furyl)-6-methoxy-7-(3-pyrrolidin-1-ylpropoxy)quinolone To a solution of intermediate I-04a (708 mg, 2 mmol) in DMF (15 mL) was added commercially available tributyl (2-furyl)stannane (R-05a) (716 mg, 2 mmol) and Pd(PPh$_3$)Cl$_2$ (87.7 mg, catalyst). The solution was heated to 110° C. for 12 hrs. The mixture was concentrated to give the crude product which was purified by prep-HPLC (General procedure, Method 1), to give intermediate I-09s (400 mg, 52% yield) as a yellow solid. ESI-MS (M+1): 387.2 calc. for C$_{21}$H$_{23}$ClN$_2$O$_3$: 386.1.

Following the same synthetic route for intermediate I-09s and using the same reagents and intermediates unless otherwise indicated in the table below, the following intermediates were obtained:

| Intermediate I-09 | Yield | [M + 1]+ | Intermediate/reagent |
|---|---|---|---|
| I-09t | 36% | 415.2 | I-04a/tributyl-(5-ethyl-2-furyl)stannane (R-05b). |

Preparation of compound 3-01: 6,7-dimethoxy-2-methyl-N-(1-methyl-4-piperidyl)quinolin-4-amine; 2,2,2-trifluoroacetic acid To a solution of intermediate I-09a (100 mg, 0.42 mmol) in DME (5 mL) was added K$_3$PO$_4$ (0.26 g, 1.26 mmol), Biphenyl-2-yl-dicyclohexyl-phosphane (0.022 g, 0.063 mmol), Pd$_2$(dba)$_3$ (0.57, 0.063 mmol), 1-methylpiperidin-4-amine (R-03a) (0.24 g, 2.1 mmol), the mixture was heated to 110° C. for 3 h under microwave. The solution was concentrated and extracted with AcOEt. The combined organic layers were washed with brine, dried over anhydrous Na$_2$SO$_4$, filtered and concentrated to give the crude product which was purified by prep-HPLC (General procedure, Method 1) to give compound 3-01 as TFA salt (0.02 g, 0.15% yield). ESI-MS (M+1): 316.2 calc. for C$_{18}$H$_{25}$N$_3$O$_2$ · C$_2$HF$_3$O$_2$: 429.2; Rt is 1.54.

Preparation of compound 3-02: 6,7-dimethoxy-2-(5-methyl-2-furyl)-N-(1-methyl-4-piperidyl)quinolin-4-amine; 2,2,2-trifluoroacetic acid Compound 3-02 was obtained in an analogous manner to compound 3-01 starting from intermediate I-09b. Purified by prep-HPLC (General procedure, Method 1). Y: 10%, as TFA salt. ESI-MS (M+1): 382.3 calc. for C$_{22}$H$_{27}$N$_3$O$_3$ · C$_2$HF$_3$O$_2$: 495.2; Rt is 1.84.

Following the same synthetic route for compound 3-02 using the same reagents unless otherwise indicated in the table below, the following compounds were obtained:

| Example | Rt (min) | [M + 1]+ | HPLC Method | R-03 |
|---|---|---|---|---|
| 3-03 | 2.83 | 353.1 | 1 | Cyclopentanamine (R-03b) |

Preparation of compound 3-04: 6-methoxy-2-(5-methyl-2-furyl)-N-(1-methyl-4-piperidyl)-7-(3-pyrrolidin-1-ylpropoxy)quinolin-4-amine; 2,2,2-trifluoroacetic acid Compound 3-04 was obtained in an analogous manner to compound 3-01 starting from intermediate I-09d. Purified by prep-HPLC (General procedure, Method 1). Y: 20%, as TFA salt ESI-MS (M+1): 479 calc. for $C_{28}H_{38}N_4O_3$. $C_2HF_3O_2$: 592.3; Rt is 1.47.

Following the same synthetic route for compound 3-04 using the same reagents and intermediates unless otherwise indicated in the table below, the following compounds were obtained:

| Example | Rt (min) | [M + 1]+ | HPLC Method | Intermediate/reagent (R-03) |
|---|---|---|---|---|
| 3-05 | 2.28 | 450.3 | 1 | I-09d/Cyclopentanamine (R-03b) |
| 3-06 | 2.18 | 422.2 | 3 | I-09d/Cyclopropanamine (R-03c) |
| 3-07 | 2.05 | 493.3 | 3 | I-09d/(1-methyl-4-piperidyl)methanamine (R-03d) |
| 3-08 | 2.02 | 465.2 | 3 | I-09d/tert-butyl 4-aminopiperidine-1-carboxylate (R-03e) |
| 3-09 | 2.61 | 458.2 | 3 | I-09d/Aniline (R-03f) |
| 3-10 | 2.18 | 426.2 | 3 | I-09d/2-aminoethanol (R-03g) |
| 3-11 | 3.48 | 478.2 | 3 | I-09d/3,3,3-trifluoropropan-1-amine (R-03h) |
| 3-12 | 3.24 | 440.2 | 3 | I-09d/2-methoxyethanamine (R-03i) |
| 3-13 | 2.33 | 472.2 | 3 | I-09d/Phenylmethanamine (R-03j) |
| 3-14 | 2.68 | 464.2 | 3 | I-09d/Cyclopentylmethanamine (R-03k) |
| 3-15 | 2.00 | 459.2 | 3 | I-09d/Pyridin-4-amine (R-03l) |
| 3-16 | 2.07 | 466.2 | 3 | I-09d/Tetrahydropyran-4-amine (R-03m) |
| 3-17 | 2.34 | 493.2 | 3 | I-09d/4-amino-1-methyl-piperidin-2-one (R-03n) |
| 3-18 | 2.70 | 479.2 | 3 | I-09d/4-aminopiperidin-2-one (R-03o) |
| 3-19 | 2.41 | 467.2 | 3 | I-09d/3-amino-N-methyl-propanamide (R-03p) |
| 3-20 | 1.82 | 505.2 | 3 | I-09d/1-cyclopropylpiperidin-4-amine (R-03q) |
| 3-21 | 2.47 | 449 | 1 | I-09c/1-methylpiperidin-4-amine (R-03a) |
| 3-22 | 1.92 | 467.3 | 4 | I-06a/1-methylpiperidin-4-amine (R-03a) |
| 3-23 | 2.31 | 413.3 | 1 | I-09e/1-methylpiperidin-4-amine (R-03a) |
| 3-24 | 2.24 | 384 | 2 | I-09e/Cyclopentanamine (R-03b) |
| 3-25 | 1.86 | 515.3 | 3 | I-09f/1-methylpiperidin-4-amine (R-03a) |
| 3-26 | 1.86 | 479.2 | 3 | I-09g/1-methylpiperidin-4-amine (R-03a) |
| 3-27 | 1.95 | 465.2 | 3 | I-09h/1-methylpiperidin-4-amine (R-03a) |
| 3-28 | 1.81 | 515.3 | 3 | I-09i/1-methylpiperidin-4-amine (R-03a) |
| 3-29 | 2.08 | 475.3 | 1 | I-09j/1-methylpiperidin-4-amine (R-03a) |
| 3-30 | 1.55 | 476.3 | 3 | I-09k/1-methylpiperidin-4-amine (R-03a) |
| 3-31 | 1.78 | 478.3 | 3 | I-09l/1-methylpiperidin-4-amine (R-03a) |
| 3-32 | 1.98 | 541.3 | 3 | I-09m/1-methylpiperidin-4-amine (R-03a) |
| 3-33 | 1.82 | 479.3 | 3 | I-09n/1-methylpiperidin-4-amine (R-03a) |
| 3-34 | 1.70 | 489.3 | 1 | I-09o/1-methylpiperidin-4-amine (R-03a) |
| 3-35 | 1.74 | 493.3 | 1 | I-09p/1-methylpiperidin-4-amine (R-03a) |
| 3-36 | 1.77 | 495.3 | 1 | I-09q/1-methylpiperidin-4-amine (R-03a) |
| 3-37 | 1.82 | 492.3 | 3 | I-09r/1-methylpiperidin-4-amine (R-03a) |
| 3-38 | 2.34 | 449.2 | 3 | I-09l/Cyclopentanamine (R-03b) |
| 3-39 | 2.41 | 492.3 | 3 | I-09l/(1-methyl-4-piperidyl)methanamine (R-03d) |
| 3-40 | 2.78 | 465.2 | 3 | I-09s/1-methylpiperidin-4-amine (R-03a) |
| 3-41 | 1.90 | 493.3 | 3 | I-09t/1-methylpiperidin-4-amine (R-03a) |
| 3-42 | 1.89 | 507.3 | 3 | I-09t/(1-methyl-4-piperidyl)methanamine (R-03d) |
| 3-45 | 2.16 | 494.3 | 6 | I-09d/4-amino-1-methyl-cyclohexanol (R-03r) |
| 3-46 | 1.53 | 483.3 | 1 | I-09u/1-methylpiperidin-4-amine (R-03a) |
| 3-47 | 2.11 | 533.2 | 1 | I-09v/1-methylpiperidin-4-amine (R-03a) |
| 3-48 | 1.82 | 519.4 | 1 | I-09t/1-cyclopropylpiperidin-4-amine (R-03q) |
| 3-49 | 1.84 | 533.4 | 1 | I-09t/(1-cyclopropyl-4-piperidyl)methanamine (R-03s) |
| 3-50 | 1.79 | 519.4 | 6 | I-09t/8-methyl-8-azabicyclo[3.2.1]octan-3-amine (R-03t) |
| 3-51 | 1.80 | 519.4 | 6 | I-09t/3-methyl-3-azabicyclo[3.2.1]octan-8-amine (R-03u) |
| 3-52 | 1.79 | 529.4 | 6 | I-09t/2,2-difluoro-1-methyl-piperidin-4-amine (R-03v) |
| 3-53 | 1.82 | 519.4 | 6 | I-09w/1-methylpiperidin-4-amine (R-03a) |
| 3-54 | 1.78 | 507.4 | 6 | I-09x/1-methylpiperidin-4-amine (R-03a) |
| 3-55 | 1.72 | 509.4 | 6 | I-09y/1-methylpiperidin-4-amine (R-03a) |
| 3-56 | 1.74 | 467.4 | 6 | I-09z/1-methylpiperidin-4-amine (R-03a) |

Preparation of compound 3-43: 2-(5-methyl-2-furyl)-4-[(1-methyl-4-piperidyl)amino]-7-(3-pyrrolidin-1-ylpropoxy)quinolin-6-ol; 2,2,2-trifluoroacetic acid To a solution of compound 3-04 (50 mg, 0.101 mmol) in DCM (10 mL) was added $BBr_3$ (254.26 mg, 1.01 mmol) slowly at 0° C., the solution was stirred at 0° C. for 2 h under $N_2$ atmosphere, Then, the solution was quenched with water and concentrated to give the crude product which was purified by prep-HPLC (General Method 3) to give compound 3-43 (11 mg, 23%) as a yellow solid.

ESI-MS (M+1): 465.3 calc. for $C_{27}H_{36}N_4O_3 \cdot C_2HF_3O_2$: 578.2; Rt is 1.6.

Preparation of compound 3-44: 2-(5-methyl-2-furyl)-4-[(1-methyl-4-piperidyl)methylamino]-7-(3-pyrrolidin-1-ylpropoxy)quinolin-6-ol; 2,2,2-trifluoroacetic acid Compound 3-44 was obtained in an analogous manner to compound 3-43 starting from compound 3-07. Purified by prep-HPLC (General procedure, Method 3). Y: 21%, as TFA salt ESI-MS (M+1): 479.3 calc. for $C_{28}H_{38}N_4O_3 \cdot C_2HF_3O_2$: 592.3; Rt is 1.74.

Synthetic Route 3b

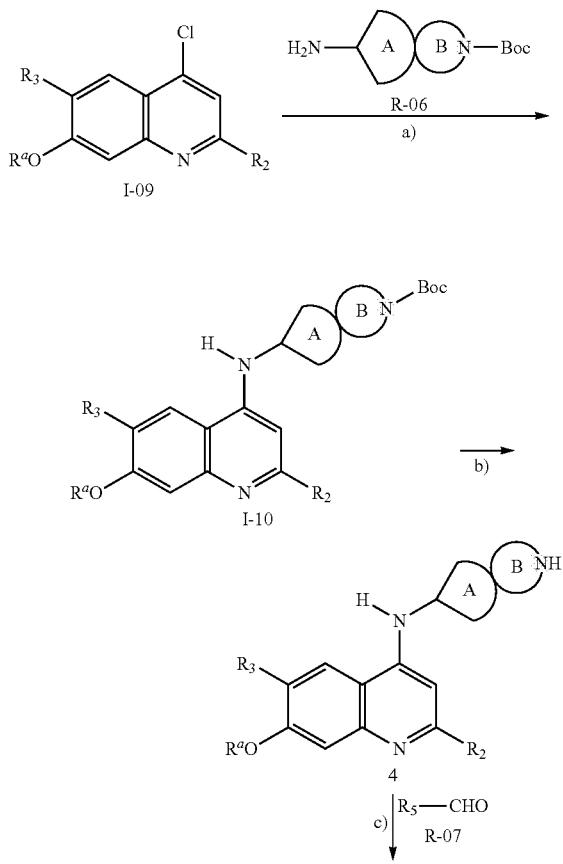

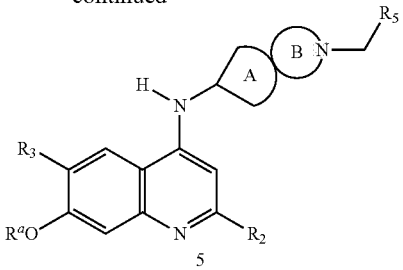

Conditions: a) R-06 (1 eq), $Pd_2(dba)_3$ (0.1 eq), BINAP (0.1 eq), $Cs_2CO_3$ (2 eq) in dioxane, mw, 5 h at 130° C.; b) HCl/MeOH (4N), 5 h at RT; c) R-07 (3 eq) in MeOH, 1 h at RT, then $NaBH(OAc)_3$ (3 eq), overnight at RT.

In the scheme above $R_2$ is aryl or heteroaryl; $R_3$ is H, Cl, $OCF_3$ or $O(C_1-C_6)$alkyl; $R_5$ is H or $(C_1-C_6)$alkyl and $R^a$ is a hydrocarbon chain, which contains nitrogen and/or oxygen atoms.

Preparation of Intermediate I-10a: tert-butyl 3-[[6-methoxy-2-(5-methyl-2-furyl)-7-(3-pyrrolidin-1-ylpropoxy)-4-quinolyl]amino]-7-azaspiro[3.5]nonane-7-carboxylate To a solution of intermediate I-09d (400 mg, 1 mmol) in 1,4-dioxane (10 mL) $Cs_2CO_3$ (650 mg, 2 mmol), BINAP (70 mg), $Pd_2(dba)_3$ (100 mg), and commercially available R-06a: tert-butyl 3-amino-7-azaspiro[3.5]nonane-7-carboxylate (224 mg 1 mmol) were added. The reaction mixture was heated to 130° C. for 5 h under microwave. The solution was concentrated and extracted with AcOEt. The organic layer was washed with brine, dried over anhydrous $Na_2SO_4$, filtered and concentrated to give the crude product which was purified by prep-HPLC (General procedure, Method 3), to give intermediate I-10a (200 mg, 17%) as a yellow solid. ESI-MS (M+1): 605.3 calc. for $C_{35}H_{48}N_4O_5$: 604.3.

Preparation of Intermediate I-10b: tert-butyl 2-[[6-methoxy-2-(5-methyl-1H-pyrrol-2-yl)-7-(3-pyrrolidin-1-ylpropoxy)-4-quinolyl]amino]-7-azaspiro[3.5]nonane-7-carboxylate To a solution of intermediate I-091 (200 mg, 0.5 mmol) in 1,4-dioxane (10 mL) $Cs_2CO_3$ (325 mg, 1 mmol), BINAP (35 mg, catalyst), $Pd_2(dba)_3$ (50 mg) and commercially available R-06b: tert-butyl 2-amino-7-azaspiro[3.5]nonane-7-carboxylate (180 mg, 0.75 mmol) were added. The reaction mixture was heated at 120° C. for 12 h. The solution was concentrated and extracted with EtOAc. The organic phase was separated, washed with brine, dried over anhydrous Na2SO4, filtered and concentrated to give the crude product which was purified by prep-HPLC (General procedure, Method 3), to give intermediate I-10b (80 mg, 17%) as a yellow solid. ESI-MS (M+1): 604.3 calc. for $C_{35}H_{49}N_5O_4$: 603.3.

Preparation of Intermediate I-10c: tert-butyl 2-[[2-(5-ethyl-2-furyl)-6-methoxy-7-(3-pyrrolidin-1-ylpropoxy)-4-quinolyl]amino]-7-azaspiro[3.5]nonane-7-carboxylate Intermediate I-10c was obtained starting from I-09t in an analogous manner to intermediate I-10b. 44% yield. ESI-MS (M+1): 619.3 calc. for $C_{36}H_{50}N_4O_5$ Preparation of Intermediate I-10d: tert-butyl 3-[[2-(5-ethyl-2-furyl)-6-methoxy-7-(3-pyrrolidin-1-yl-propoxy)-4-quinolyl]amino]-7-azaspiro[3.5]nonane-7-carboxylate Intermediate I-10d was obtained starting from I-09t in an analogous manner to intermediate I-10a. 24% yield. ESI-MS (M+1): 619.4 calc. for $C_{36}H_{50}N_4O_5$ Preparation of compound 4-01: N-(7-azaspiro[3.5]nonan-3-yl)-6-methoxy-2-(5-methyl-2-furyl)-7-(3-pyrrolidin-1-ylpropoxy)quinolin-4-amine; 2,2,2-trifluoroacetic acid To a solution of intermediate I-10a (60.4 mg, 0.1 mmol) in MeOH (10 mL) was added HCl/MeOH (5 mL, 4M), the solution was stirred at RT for 5 h. The solution was concentrated to give compound 4-01 as TFA salt (49 mg, 97%) as a yellow solid. ESI-MS (M+1): 505.3 calc. for $C_{30}H_{40}N_4O_3 \cdot C_2HF_3O_2$: 618.3; Rt is 2.29.

Preparation of compound 4-02: N-(7-azaspiro[3.5]nonan-2-yl)-6-methoxy-2-(5-methyl-1H-pyrrol-2-yl)-7-(3-pyrrolidin-1-ylpropoxy)quinolin-4 amine; hydrochloride Compound 4-02 was obtained as HCl salt starting from I-10b in an analogous manner to compound 4-01. 92% yield. ESI-MS (M+1): 504.3 calc. for $C_{30}H_{41}N_5O_2 \cdot ClH$: 539.3; Rt is 1.89

Preparation of compound 4-03: N-(7-azaspiro[3.5]nonan-2-yl)-2-(5-ethyl-2-furyl)-6-methoxy-7-(3-pyrrolidin-1-ylpropoxy)quinolin-4-amine:2,2,2-trifluoroacetic acid Compound 4-03 was obtained as TFA salt starting from I-10c in an analogous manner to compound 4-01. Purification by prep-HPLC (General procedure, Method 3), 34% yield. ESI-MS (M+1): 519.4 calc. for $C_{31}H_{42}N_4O_3 \cdot C_2HF_3O_2$: 632.3; Rt is 1.85.

Preparation of compound 4-04: N-(7-azaspiro[3.5]nonan-3-yl)-2-(5-ethyl-2-furyl)-6-methoxy-7-(3-pyrrolidin-1-ylpropoxy)quinolin-4-amine; hydrochloride Compound 4-04 was obtained as HCl salt starting from I-10d in an analogous manner to compound 4-01. 89% yield. ESI-MS (M+1): 519.4 calc. for $C_{31}H_{42}N_4O_3 \cdot HCl$: 554.3.

Preparation of compound 5-01: 6-methoxy-N-(7-methyl-7-azaspiro[3.5]nonan-3-yl)-2-(5-methyl-2-furyl)-7-(3-pyrrolidin-1-ylpropoxy)quinolin-4-amine; 2,2,2-trifluoroacetic acid To a solution of compound 4-01 (50.5 mg, 0.1 mmol) in MeOH (10 mL) was added R-07a: (HCHO)n (9 mg, 0.3 mmol). The solution was stirred at r.t for 1 h, then NaBH(OAc)$_3$ (25 mg, 0.3 mmol) was added and the reaction mixture was stirred at RT overnight. The organic layer was washed with brine, dried over anhydrous $Na_2SO_4$, filtered and concentrated to give the crude product which was purified by prep-HPLC (General procedure, Method 3), to give compound 5-01 as TFA salt (25 mg, 48%) as a yellow solid. ESI-MS (M+1): 519.3 calc. for $C_{31}H_{42}N_4O_3 \cdot C_2HF_3O_2$: 632.3; Rt is 2.29.

Following the same synthetic route for compound 5-01 using the same reagents unless otherwise indicated in the table below, the following compounds were obtained:

| Example | $R_t$ (min) | $[M + 1]^+$ | HPLC Method | R-06 |
|---|---|---|---|---|
| 5-02 | 2.22 | 519.3 | 3 | tert-butyl 2-amino-7-azaspiro[3.5]nonane-7-carboxylate (R-06b) |
| 5-03 | 2.16 | 505.3 | 3 | tert-butyl 2-amino-6-azaspiro[3.4]octane-6-carboxylate (R-06c) |
| 5-04 | 2.36 | 505.3 | 3 | tert-butyl 3-amino-6-azaspiro[3.4]octane-6-carboxylate (R-06d) |

Preparation of compound 5-05: 6-methoxy-N-(7-methyl-7-azaspiro[3.5]nonan-2-yl)-2-(5-methyl-1H-pyrrol-2-yl)-7-(3-pyrrolidin-1-ylpropoxy)quinolin-4-amine; 2,2,2-trifluoroacetic acid Compound 5-05 was obtained starting from 4-02 in an analogous manner to compound 5-01. Purification by prep-HPLC (General procedure, Method 3), 35% yield. ESI-MS (M+1): 518.4 calc. for $C_{31}H_{43}N_5O_2 \cdot C_2HF_3O_2$: 631.3; Rt is 1.83.

Preparation of compound 5-06: 2-(5-ethyl-2-furyl)-6-methoxy-N-(7-methyl-7-azaspiro[3.5]nonan-2-yl)-7-(3-pyrrolidin-1-ylpropoxy)quinolin-4-amine; 2,2,2-trifluoroacetic acid Compound 5-06 was obtained starting from 4-03 in an analogous manner to compound 5-01. Purification by prep-HPLC (General procedure, Method 6), 19% yield. ESI-MS (M+1): 533.4 calc. for $C_{32}H_{44}N_4O_3 \cdot C_2HF_3O_2$: 646.3; Rt is 1.88.

Preparation of compound 5-07: 2-(5-ethyl-2-furyl)-6-methoxy-N-(7-methyl-7-azaspiro[3.5]nonan-3-yl)-7-(3-pyrrolidin-1-ylpropoxy)quinolin-4-amine; 2,2,2-trifluoroacetic acid Compound 5-07 was obtained starting from 4-04 in an analogous manner to compound 5-01. Purification by prep-HPLC (General procedure, Method 6), 96% yield. ESI-MS (M+1): 533.5 calc. for $C_{32}H_{44}N_4O_3 \cdot C_2HF_3O_2$: 646.3; Rt is 1.90.

Synthetic Route 4

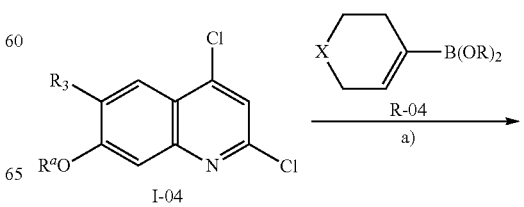

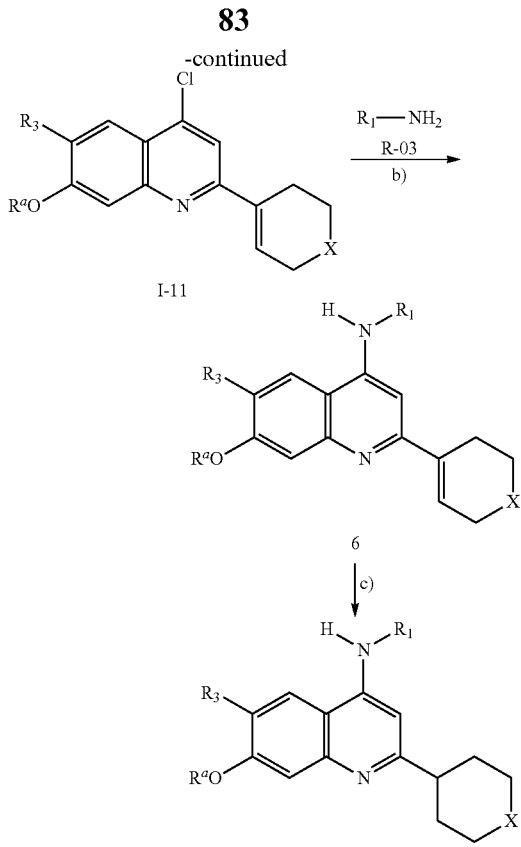

I-11

6

7

Conditions: a) R-04 (1 eq), Pd(Ph₃)₄ (0.3 eq), K₂CO₃ (2 eq.), in dioxane/water (5/1), mw, 1 h at 120° C.; b) R-03 (3 eq), Pd₂(dba)₃ (0.3 eq), BINAP (0.3 eq), Cs₂CO₃ (4 eq), in 1,4-dioxane, mw, 1 h. at 110° C.; c) H₂, Pd/C in EtOH, overnight at RT.

In the scheme above $R_1$ is cycle (Cy) or a hydrocarbon chain, which optionally contains nitrogen, oxygen and/or fluor atoms, were Cy is an aryl, heteroaryl, carbocycle or heterocyclic ring; $R_3$ is $O(C_1-C_6)$alkyl; $R^a$ is a hydrocarbon chain, which contains nitrogen atoms and X is carbono or oxygen atom.

Preparation of Intermediate I-11a: 4-chloro-2-(cyclohexen-1-yl)-6-methoxy-7-(3-pyrrolidin-1-yl-propoxy)quinolone To a solution of intermediate I-04a (708 mg, 2 mmol) in dioxane/water (5/1 mL) were added K₂CO₃ (27 mg, 0.20 mmol), Pd(PPh₃)₄ (233 mg, 30%), 2-(cyclohex-1-en-1-yl)-4,4,5,5-tetramethyl-1,3,2-dioxaborolane (R-04i) (416 mg, 2 mmol), the solution was heated at 120° C. under MW for 1 h, and then the mixture was concentrated and extracted with AcOEt. The combined organic layers were washed with brine, dried over anhydrous Na₂SO₄, filtered and concentrated to give the crude product which was purified by column chromatography (eluent gradient PE:EA=1:0 to 3:1) to give intermediate I-11a (0.4 g, 50% yield) as a yellow solid. ESI-MS (M+1): 401 calc. for $C_{23}H_{29}ClN_2O_2$: 400.2.

Preparation of compound 6-01: 2-(cyclohexen-1-yl)-6-methoxy-N-(1-methyl-4-piperidyl)-7-(3-pyrrolidin-1-ylpropoxy)quinolin-4-amine; 2,2,2-trifluoroacetic acid Compound 6-01 was obtained in an analogous manner to compound I-01 starting from intermediate I-11a. Purified by prep-HPLC (General procedure, Method 5). Y: 20%, as TFA salt. ESI-MS (M+1): 479.6 calc. for $C_{29}H_{42}N_4O_2 \cdot C_2HF_3O_2$: 592.3; Rt is 1.48.

Following the same synthetic route for compound 6-01 and using the reagents indicated in the table below, the following compounds were obtained:

| Example | Rt (min) | [M + 1]⁺ | HPLC Method | reagent |
|---|---|---|---|---|
| 6-02 | 2.65 | 481.3 | 3 | 2-(3,6-dihydro-2H-pyran-4-yl)-4,4,5,5-tetramethyl-1,3,2-dioxaborolane (R-04j) |

Preparation of compound 6-03: tert-butyl 4-[[2-(cyclohexen-1-yl)-6-methoxy-7-(3-pyrrolidin-1-yl-propoxy)-4-quinolyl]amino]piperidine-1-carboxylate To a solution of intermediate I-11a (150 mg, 374.12 umol) and tert-butyl 4-aminopiperidine-1-carboxylate (R-03x) (374.6 mg, 1.87 mmol) in dioxane (30 mL) were successively added Pd₂(dba)₃ (68.5 mg, 74.82 umol), BINAP (93.2 mg, 149.65 umol) and Cs₂CO₃ (304.8 mg, 935.30 umol). The resulting mixture was stirred at 130° C. for 36 hrs under N₂. Then, the mixture was diluted with water (50 mL), and extracted with EtOAc (2×40 mL). The combined organic phase was washed with brine (80 mL), dried with Na₂SO₄, concentrated and purified by prep-TLC (DCM:MeOH=10:1) to give compound 6-03 (156 mg 73.83% yield) as a yellow solid. ESI-MS (M+1): 565.4 calc. for $C_{33}H_{48}N_4O_4$.

Preparation of compound 7-01: 2-cyclohexyl-6-methoxy-N-(1-methyl-4-piperidyl)-7-(3-pyrrolidin-1-ylpropoxy)quinolin-4-amine; 2,2,2-trifluoroacetic acid To a solution of compound 6-01 (47.8 mg, 0.1 mmol) in EtOH (10 mL) was added Pd/C (15 mg) under H₂. The solution was stirred at r.t overnight. The reaction mixture was filtered, the filtrate was concentrated to give the desired product compound 7-01 as TFA salt (0.048 g, 95% yield), ESI-MS (M+1): 481 calc. for $C_{29}H_{44}N_4O_2 \cdot C_2HF_3O_2$: 594.3; Rt is 1.54.

Preparation of compound 7-02: 6-methoxy-N-(1-methyl-4-piperidyl)-7-(3-pyrrolidin-1-ylpropoxy)-2-tetrahydropyran-4-yl-quinolin-4-amine; 2,2,2-trifluoroacetic acid Compound 7-02 was obtained in an analogous manner to compound 7-01 starting from compound 6-02. 63.5% yield, as TFA salt. ESI-MS (M+1): 483.3 calc. for $C_{28}H_{42}N_4O_3 \cdot C_2HF_3O_2$: 596.3; Rt is 2.44.

Preparation of compound 7-03: tert-butyl 4-[[2-cyclohexyl-6-methoxy-7-(3-pyrrolidin-1-ylpropoxy)-4-quinolyl]amino]piperidine-1-carboxylate Compound 7-03 was obtained in an analogous manner to compound 7-01 starting from compound 6-03. 99% yield. ESI-MS (M+1): 567.5 calc. for $C_{33}H_{50}N_4O_4$ Preparation of compound 7-04: 2-cyclohexyl-6-methoxy-N-(4-piperidyl)-7-(3-pyrrolidin-1-yl-propoxy)quinolin-4-amine; 2,2,2-trifluoroacetic acid A solution of compound 7-03 (65.00 mg, 114.68 umol) in HCl/EtOAc (1.0 M, 20.00 mL) was stirred at 16° C. for 4 hours. Then, the reaction mixture was concentrated and purified by prep-HPLC (General procedure, Method 1) to afford the desired product 7-04 as TFA salt (40.3 mg, 60.5% yield) as a yellow solid. ESI-MS (M+1): 467.4 calc. for $C_{28}H_{42}N_4O_2 \cdot C_2HF_3O_2$: 580.3; Rt is 1.73.

Preparation of compound 7-05: 2-cyclohexyl-N-(1-isopropyl-4-piperidyl)-6-methoxy-7-(3-pyrrolidin-1-ylpropoxy)quinolin-4-amine; 2,2,2-trifluoroacetic acid To a mixture of compound 7-04 (90 mg, 178.88 umol) and acetone (62.4 mg, 1.07 mmol) in THF (30 mL) were added AcOH (64.5 mg, 1.07 mmol) and $NaBH_3CN$ (67.5 mg, 1.07 mmol) in one portion at 16° C. under $N_2$. The mixture was stirred at 50° C. for 15 hours. Then, the mixture was cooled to 16° C., filtered and concentrated in vacuum. The residue was purified by prep-HPLC (General procedure, Method 1) to afford the desired product 7-05 as TFA salt (38 mg, 33% yield) as a yellow solid. ESI-MS (M+1): 509.5 calc. for $C_{31}H_{48}N_4O_2 \cdot C_2HF_3O_2$: 622.3; Rt is 1.81.

Synthetic Route 5

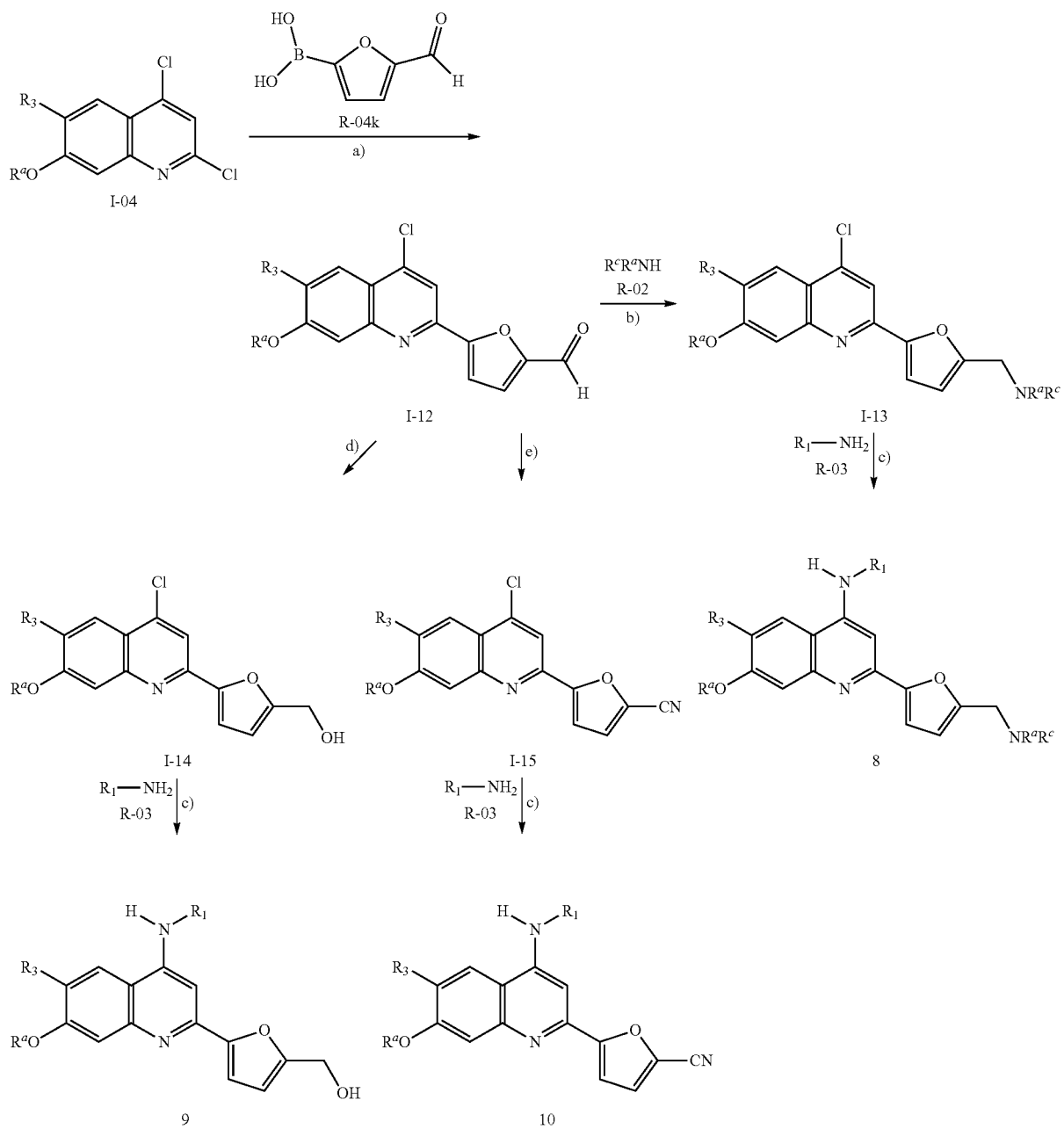

Conditions: a) R-04k (0.9 eq), Pd(Ph$_3$)$_4$ (0.1 eq), Na$_2$CO$_3$ (3 eq.), in dioxane/water (5/1), mw, 2 h at 110° C.; b) R-02 (3 eq), NaBH$_3$CN (5 eq) in MeOH, 12 h at RT; c) R-03 (5 eq), Pd$_2$(dba)$_3$ (0.3 eq), x-Phos (0.2 eq), t-BuOK (1.5 eq), in toluene, mw, 2 h. at 130° C.; d) phenylphosphonic dichloride (2 eq), pyridine (4 eq), NH$_2$OH•HCl (1 eq), in MeOH/DCM (1/4), 15 h at RT, then, NaBH$_3$CN (9 eq), 12 h at RT.

In the scheme above $R_3$, $R^a$ and $R^c$ are as previously defined and $R_1$ is cycle (Cy) or a hydrocarbon chain, which optionally contains nitrogen, oxygen and/or fluor atoms, were Cy is an aryl, heteroaryl, carbocycle or heterocyclic ring; $R_3$ is $O(C_1-C_6)$alkyl and $R^a$ is a hydrocarbon chain, which contains nitrogen atoms

Preparation of Intermediate I-12a: 5-[4-chloro-6-methoxy-7-(3-pyrrolidin-1-ylpropoxy)-2-quinolyl]furan-2-carbaldehyde To a solution of intermediate I-04a (1 g, 2.8 mmol) in 1,4-dioxane/H2O (15/3 mL) were added $Na_2CO_3$ (890 mg, 8.4 mmol), $Pd(PPh_3)_4$ (323 mg, 0.28 mmol) and (5-formyl-2-furyl)boronic acid (R-04k) (347 mg, 2.52 mmol). The solution was heated at 110° C. for 2 h. under microwave. The mixture was concentrated and extracted with EtOAc. The combined organic layers were washed with brine, dried over anhydrous $Na_2SO_4$, filtered and concentrated to give the crude product which was purified by prep-TLC to give intermediate I-12a (0.5 g, 47% yield) as a pale yellow solid. ESI-MS (M+1): 415 calc.

$C_{22}H_{23}ClN_2O_4$: 414.1.

Preparation of Intermediate I-13a: 1-[5-[4-chloro-6-methoxy-7-(3-pyrrolidin-1-ylpropoxy)-2-quinolyl]-2-furyl]-N,N-dimethyl-methanamine To a solution of intermediate I-12a (180 mg, 0.43 mmol) in MeOH (5 mL) was added dimethylamine (R-02b) (105 mg, 1.30 mmol), The solution was stirred at r.t for 1.5 h, then, $NaBH_3CN$ (135 mg, 2.15 mol) was added to the solution, The solution was stirred at r.t for 12 h. The mixture was quenched with water and extracted with AcOEt. The organic layer was washed with brine, dried over anhydrous $Na_2SO_4$, filtered and concentrated to give the crude product which was purified by prep-HPLC (General procedure, Method 1) to obtain pure intermediate I-13a (100 mg, 52% yield) as a yellow solid. ESI-MS (M+1): 444 calc. for $C_{24}H_{30}ClN_3O_3$: 443.2.

Preparation of compound 8-01: 2-[5-[(dimethylamino)methyl]-2-furyl]-6-methoxy-N-(1-methyl-4-piperidyl)-7-(3-pyrrolidin-1-ylpropoxy)quinolin-4-amine; 2,2,2-trifluoroacetic acid To a solution of intermediate I-13a (80 mg, 0.18 mmol) in toluene (5 mL) were added t-BuOK (0.27 mL, 0.27 mmol), x-Phos (17 mg, 0.036 mmol), $Pd_2(dba)_3$ (49 mg, 0.054 mmol) and R-03a: 1-methylpiperidin-4-amine (119 mg, 0.9 mmol). The solution was heated to 130° C. for 2 h under microwave. The mixture was quenched with water and extracted with AcOEt. The organic layer was washed with brine, dried over anhydrous $Na_2SO_4$, filtered and concentrated to give the crude product which was purified (General procedure, Method 1) to obtain pure compound 8-01 as TFA salt (20.7 mg, 22% yield). ESI-MS (M+1): 522.3 calc. for $C_{30}H_{43}N_5O_3.C_2HF_3O_2$: 635.3; Rt is 1.93.

Following the same synthetic route for compound 8-01 and using the reagents indicated in the table below, the following compounds were obtained:

| Example | Rt (min) | [M + 1]+ | HPLC Method | reagent |
|---|---|---|---|---|
| 8-02 | 1.98 | 522.3 | 1 | ethanamine (R-02c) |

Preparation of Intermediate I-14a: [5-[4-chloro-6-methoxy-7-(3-pyrrolidin-1-ylpropoxy)-2-quinolyl]-2-furyl]methanol To a solution of intermediate I-12a (200 mg, 0.48 mmol) in MeOH (5 mL), $NaBH_4$ (91.2 mg, 2.4 mmol) was added. The solution was stirred at RT for 2 h. The mixture was concentrated to give the crude product which was purified by prep-TLC to give intermediate I-14a (0.1 g, 49%) as a pale yellow solid.
ESI-MS (M+1): 417 calc. $C_{22}H_{25}ClN_2O_4$: 416.1.

Preparation of compound 9-01: [5-[6-methoxy-4-[(1-methyl-4-piperidyl)amino]-7-(3-pyrrolidin-1-ylpropoxy)-2-quinolyl]-2-furyl]methanol; 2,2,2-trifluoroacetic acid To a solution of intermediate I-14a (90 mg, 0.21 mmol) in 1,4-dioxane (4 mL) was added $Cs_2CO_3$ (0.21 g, 0.65 mmol), BINAP (0.027 g, 0.043 mmol), $Pd_2(dba)_3$ (0.059 g, 0.065 mmol) and 1-methylpiperidin-4-amine (0.086 g, 0.65 mmol). The solution was heated to 120° C. for 5 h under microwave. The mixture was quenched with water and extracted with AcOEt. The organic layer was washed with brine, dried over anhydrous $Na_2SO_4$, filtered and concentrated to give the crude product which was purified by prep-HPLC (General procedure, Method 3) to obtain compound 9-01 as TFA salt (10 mg, 8%). ESI-MS (M+1): 495 calc. for $C_{28}H_{38}N_4O_4.C_2HF_3O_2$: 608.2; Rt is 2.43.

Preparation of Intermediate I-15a: 5-[4-chloro-6-methoxy-7-(3-pyrrolidin-1-ylpropoxy)-2-quinolyl]furan-2-carbonitrile To a solution of intermediate I-12a (100 mg, 0.24 mmol) in MeOH/DCM (¼ mL), was added phenylphosphonic dichloride (94 mg, 0.48 mmol), pyridine (76 mg, 0.96 mmol) and $NH_2OH.HCl$ (16.7 mg, 0.24 mmol), The mixture was stirred at RT for 15 h. Then, $NaBH_3CN$ (135 mg, 2.15 mol) was added, The reaction mixture was stirred at RT for 12 h. The mixture was concentrated and extracted with AcOEt/water. The organic layer was separated, washed with $NaHCO_3$ brine, dried over anhydrous $Na_2SO_4$, filtered and concentrated. The residue was purified by column chromatography to give intermediate I-15a (50 mg, 51%) as a yellow solid. ESI-MS (M+1): 412 calc. For $C_{22}H_{22}ClN_3O_3$: 411.1.

Preparation of compound 10-01: 5-[6-methoxy-4-[(1-methyl-4-piperidyl)-amino]-7-(3-pyrrolidin-1-ylpropoxy)-2-quinolyl]furan-2-carbonitrile; 2,2,2-trifluoroacetic acid Compound 10-01 was obtained in an analogous manner to compound 9-01 starting from intermediate I-15a. Purified by prep-HPLC (General procedure, Method 1), 10% yield, as TFA salt. ESI-MS (M+1): 490 calc. for $C_{28}H_{35}N_5O_3.C_2HF_3O_2$: 603.2; Rt is 1.91.

Synthetic Route 6

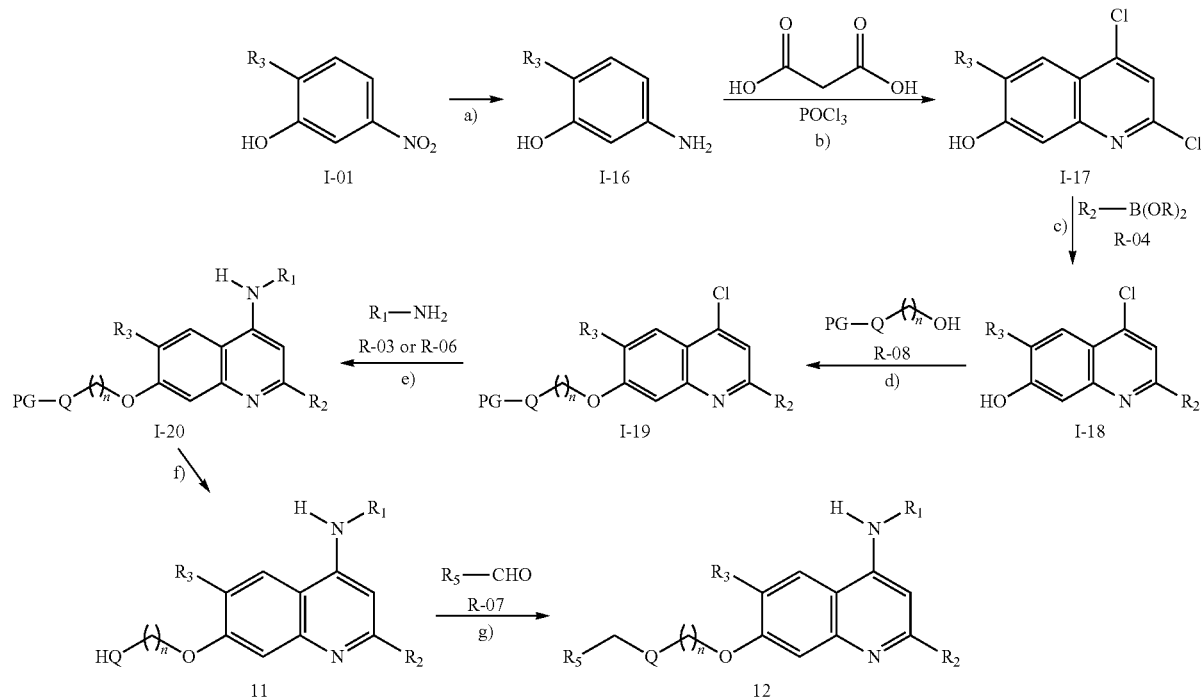

Conditions: a) Pd/C in MeOH, H₂ atmosphere, RT for 24 h; b) Malonic acid (1.1 eq) in POCl₃, at 95° C. for 12 h; c) R-04 (1.1 eq), Pd(Ph₃)₄ (0.1 eq), in dioxane, K₂CO₃ (1.5 eq.) in water at 120° C. for 12 h; d) R-08 (1.2 eq), Ph₃P (2 eq), DIAD (2 eq) at 0° C. for 8 h; e) R-03 or R-06 (2 eq), Pd₂(dba)₃ (0.1 eq), BINAP (0.1 eq), Cs₂CO₃ (2 eq) in dioxane, 120° C. for 12 h; f) HCl/AcOEt, RT for 3 h; g) R-07 (3 eq), NaBH(OAc)₃ (3 eq), HCOOH (1 eq) in dioxane, at 100° C. for 2 h.

In the scheme above $R_1$, $R_2$ and $R_3$ are as previously defined; n is 0 to 3, $R_5$ is H or $(C_1-C_6)$alkyl, Q is nitrogen and PG is a protective group.

Preparation of Intermediate I-16a:
5-amino-2-methoxy-phenol

To a solution of commercially available 2-methoxy-5-nitro-phenol: I-01a (40 g, 236.5 mmol) in MeOH (300 mL) was added Pd/C (3 g) under Ar. The suspension was degassed under vacuum and purged with H₂ several times. The reaction mixture was stirred under H₂ (40 psi) at RT for 24 h. Then, the mixture was filtered and the filtrate was concentrated to give intermediate I-16a (25 g, 76%) as a yellow solid. ESI-MS (M+1): 140.1 calc. for $C_7H_9NO_2$: 139.06.

Preparation of Intermediate I-17a:
2,4-dichloro-6-methoxy-quinolin-7-ol

To a mixture of intermediate I-16a (4.91 g, 35.29 mmol) and malonic acid (7.34 g, 70.57 mmol) was added POCl₃ (70 mL) in one portion at RT under N₂ atmosphere. The mixture was stirred at RT for 10 min, then heated at 95° C. and stirred for 12 h. Then, the mixture was cooled to RT and concentrated under reduced pressure at 60° C., to remove POCl₃. The residue was poured into water and stirred for 20 min. The aqueous phase was extracted with AcOEt. The organic phase was separated, washed with brine, dried with anhydrous Na₂SO₄, filtered and concentrated in vacuum. The residue was purified by silica gel chromatography (PE/EtOAc=2/1) to afford intermediate I-17a (2.10 g, 24% yield). ESI-MS (M+1): 244.0 calc. for $C_{23}H_{27}ClN_2O_3$: 242.9.

Preparation of Intermediate I-18a: 4-chloro-6-methoxy-2-(5-methyl-2-furyl)quinolin-7-ol To a mixture of intermediate I-17a (6 g, 24.58 mmol), R-04b:4,4,5,5-tetramethyl-2-(5-methyl-2-furyl)-1,3,2-dioxaborolane (5.63 g, 27.04 mmol) and Pd(PPh₃)₄ (2.86 g, 2.46 mmol) in 1,6-dioxane (90 mL) was added K₂CO₃ (3.40 g, 36.87 mmol) in H₂O (30 mL) in one portion at RT under N₂ atmosphere. The reaction mixture was stirred at 120° C. for 12 h. The mixture was cooled to RT and extracted with AcOEt. The organic phase was separated, washed with brine, dried with anhydrous Na₂SO₄, filtered and concentrated in vacuum. The residue was purified by silica gel chromatography (PE/EtOAc=2/1) to afford intermediate I-18a (2.1 g, 29% yield) as a yellow solid. ESI-MS (M+1): 290.1 calc. for $C_{15}H_{12}ClNO_3$: 289.05.

Preparation of Intermediate I-19a: tert-butyl 4-[[4-chloro-6-methoxy-2-(5-methyl-2-furyl)-7-quinolyl]oxymethyl]piperidine-1-carboxylate To a mixture of intermediate I-18a (650 mg, 2.24 mmol), R-08a: tert-butyl 4-(hydroxymethyl)piperidine-1-carboxylate (540.3 mg, 2.69 mmol) and PPh₃ (1.18 g, 4.48 mmol) in THF (50 mL), was added DIAD (907.34 mg, 4.48 mmol) in one portion at 0° C. under N₂ atmosphere. The reaction mixture was stirred at 0° C. for 8 h. Then, the mixture was cooled to RT and concentrated. Water and AcOEt were added. The organic phase was separated, washed with brine, dried with anhydrous $Na_2SO_4$, filtered and concentrated in vacuum. The residue was purified by silica gel chromatography (PE/EtOAc=2/1) to afford intermediate I-19a (700 mg, 64% yield). ESI-MS (M+1): 487.3 calc. for $C_{26}H_{31}ClN_2O_5$: 486.2.

Following the same synthetic route for intermediate I-19a starting from I-17a and using the reagents indicated in the table below, the following intermediates were obtained:

| Intermediate | [M + 1]+ | Reagents |
|---|---|---|
| I-19b | 473.1 | 4,4,5,5-tetramethyl-2-(5-methyl-2-furyl)-1,3,2-dioxaborolane (R-04b)/tert-butyl 4-hydroxypiperidine-1-carboxylate (R-08b) |
| I-19c | 501.3 | 4,4,5,5-tetramethyl-2-(5-ethyl-2-furyl)-1,3,2-dioxaborolane (R-04r)/tert-butyl 4-(hydroxymethyl)piperidine-1-carboxylate (R-08a) |
| I-19d | 486.3 | 2-methyl-5-(4,4,5,5-tetramethyl-1,3,2-dioxaborolan-2-yl)-1H-pyrrole (R-04k)/tert-butyl 4-(hydroxymethyl)piperidine-1-carboxylate (R-08a) |

Preparation of Intermediate I-20a: tert-butyl 4-[[6-methoxy-2-(5-methyl-2-furyl)-4-[(1-methyl-4-piperidyl)amino]-7-quinolyl]oxymethyl]piperidine-1-carboxylate To a mixture of intermediate I-19a (250 mg, 0.528 mmol) and commercially available R-03a: 1-methylpiperidin-4-amine (120.7 mg, 1.06 mmol) in 1,4-dioxane (20 mL), were added $Cs_2CO_3$ (344.28 mg, 1.06 mmol) and $Pd(dba)_2$ (30.38 mg, 0.52 mmol) in one portion at RT under $N_2$ atmosphere. The reaction mixture was stirred at 120° C. for 12 h. The mixture was cooled to 25° C. and concentrated. The residue was purified by silica gel (DCM/MeOH=10/1) to afford intermediate I-20a (100 mg, 33% yield) as a yellow solid.

Following the same synthetic route for intermediate I-20a and using the reagents indicated in the table below, the following intermediates were obtained:

| Intermediate | Yield | [M + 1]+ | Intermediate/reagents |
|---|---|---|---|
| I-20b | 8% | 579.4 | I-19a/(1-methyl-4-piperidyl)methanamine (R-03d) |
| I-20c | 86% | 579.3 | I-19a/4-amino-1-methyl-piperidin-2-one (R-03n) |
| I-20d | 56% | 691.4 | I-19a/tert-butyl 2-amino-7-azaspiro[3.5]nonane-7-carboxylate (R-06b) |
| I-20e (19-03) | 11% | 551.4 | I-19b/1-methylpiperidin-4-amine (R-03a) |
| I-20f | 17% | 579.3 | I-19c/1-methylpiperidin-4-amine (R-03a) |
| I-20g | 38% | 593.4 | I-19c/4-amino-1-methyl-piperidin-2-one (R-03n) |
| I-20h | 78% | 564.4 | I-19d/1-methylpiperidin-4-amine (R-03a) |
| I-20i | 84% | 578.4 | I-19d/(1-methyl-4-piperidyl)methanamine (R-03d) |
| I-20j | 66% | 592.3 | I-19d/4-(aminomethyl)-1-methyl-piperidin-2-one (R-03w) |
| I-20k | 96% | 507.3 | I-19d/cyclopropanamine (R-03c) |
| I-20l | 88% | 690.4 | I-19d/tert-butyl 2-amino-7-azaspiro[3.5]nonane-7-carboxylate (R-06b) |
| I-20m | 39% | 578.4 | I-19d/4-amino-1-methyl-piperidin-2-one (R-03n) |

Preparation of compound 11-01: 6-methoxy-2-(5-methyl-2-furyl)-N-(1-methyl-4-piperidyl)-7-(4-piperidylmethoxy)quinolin-4-amine; 2,2,2-trifluoroacetic acid To a solution of intermediate I-20a (160 mg, 0.283 mmol) in EtOAc (10 mL), was added HCl/EtOAc (10 mL) in one portion at 25° C. under $N_2$. The reaction was stirred at 25° C. for 3 h. Then, the mixture was concentrated in reduced pressure at 45° C. The residue was purified by prep-HPLC (General procedure, Method 3) to afford compound 11-01 as TFA salt (100 mg, 76% yield). ESI-MS (M+1): 465.3 calc. for $C_{27}H_{36}N_4O_3.C_2HF_3O_2$: 578.2; Rt is 1.65.

Following the same synthetic route for compound 11-01 starting from intermediate indicated in the table below, the following compounds were obtained:

| Example | Rt (min) | [M + 1]+ | HPLC Method | Intermediate |
|---|---|---|---|---|
| 11-02 | 1.70 | 479.4 | 6 | I-20b |
| 11-03 | 1.82 | 479.3 | 6 | I-20f |
| 11-04 | 1.67 | 451.2 | 6 | I-20e (19-03) |
| 11-05 | 1.77 | 464.3 | 6 | I-20h |
| 11-06 | 1.81 | 478.3 | 6 | I-20i |
| 11-07 | 1.94 | 492.3 | 6 | I-20j |
| 11-08 | 2.15 | 407.2 | 6 | I-20k |
| 11-09 | 1.86 | 490.3 | 6 | I-20l |
| 11-10 | 1.77 | 491.4 | 6 | I-20d |
| 11-11 | 2.24 | 478.3 | 6 | I-20m |
| 11-12 | 1.99 | 493.3 | 6 | I-20g |
| 11-13 | 1.90 | 479.4 | 6 | I-20c |

Preparation of compound 12-01: 6-methoxy-2-(5-methyl-2-furyl)-N-(1-methyl-4-piperidyl)-7-[(1-methyl-4-piperidyl)methoxy]quinolin-4-amine; 2,2,2-trifluoroacetic acid To a solution of compound 11-01 (80 mg, 0.172 mmol) in 1,4-dioxane (5 mL) was added R-07a: $(HCHO)_n$ (46.53 mg, 0.516 mmol) $NaBH(OAc)_3$ (109.49 mg, 0.516 mmol) and HCOOH (8.27 mg, 0.172 mmol) in one portion at r.t. under $N_2$. The mixture was stirred at RT for 10 min. Then stirred at 100° C. and for 2 h. The crude product was purified prep-HPLC (General procedure, Method 3) to afford compound 12-01 as TFA salt (15 mg, 14% yield) as a yellow solid. ESI-MS (M+1): 479.4 calc. for $C_{28}H_{38}N_4O_3.C_2HF_3O_2$: 592.2; Rt is 1.66.

Following the same synthetic route for compound 12-01 starting from compound indicated in the table below, the following compounds were obtained:

| Example | Rt (min) | [M + 1]+ | HPLC Method | Starting material |
|---|---|---|---|---|
| 12-02 | 1.61 | 465.3 | 6 | 11-04 |
| 12-03 | 1.79 | 519.4 | 6 | 11-10 |
| 12-04 | 1.93 | 492.3 | 6 | 11-11 |
| 12-05 | 2.00 | 507.3 | 6 | 11-12 |
| 12-06 | 1.90 | 493.4 | 6 | 11-13 |

Synthetic Route 7

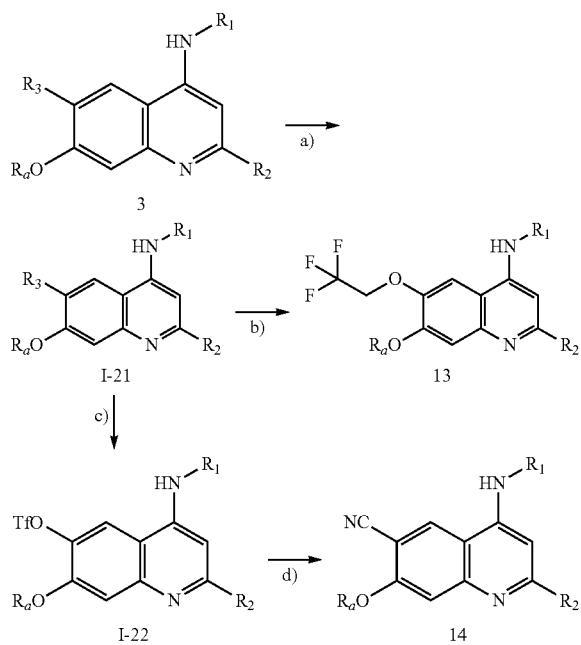

Conditions: a) BBr$_3$ (1 eq), DCM, 0° C., 2 h; b) CF$_3$CH$_2$I (2 eq), DMF, 110° C., 12 h; c) DIEA (2 eq), PhN(OTf)$_2$ (1.5 eq), DMF, 0° C., 2 h, then, 25° C., 12 h; d) Zn(CN)$_2$ (2 eq), Pd(PPh$_3$)$_4$ (cat), DMF, 110° C., 12 h.

In the scheme above R$_1$ is as previously defined; R$_2$ is aryl or heteroaryl; R$_3$ is OCH$_3$ and R$^a$ is a hydrocarbon chain, which contains nitrogen and/or oxygen atoms Preparation of compound 13-01: 2-(5-methyl-2-furyl)-N-(1-methyl-4-piperidyl)-7-(3-pyrrolidin-1-ylpropoxy)-6-(2,2,2-trifluoroethoxy)quinolin-4-amine; 2,2,2-trifluoroacetic acid To a solution of compound I-21a (100 mg, 0.215 mmol, 3-43) in DMF (3 mL) was added CF$_3$CH$_2$I (113 mg, 0.540 mmol), the solution was heated to 110° C. for 12 hours. Then, the solution was purified by prep-HPLC (General procedure, Method 6) to give compound 13-01 as TFA salt (4 mg, 3.41%) as yellow solid. ESI-MS (M+1): 547.3 calc. for C$_{29}$H$_{37}$F$_3$N$_4$O$_3$.C$_2$HF$_3$O$_2$: 660.2; Rt is 1.78.

Preparation of Intermediate I-22a: hydroxy(2-(5-methylfuran-2-yl)-4-((1-methylpiperidin-4-yl)amino)-7-(3-(pyrrolidin-1-yl)propoxy)quinolin-6-yl)(trifluoromethyl)-$\lambda^7$-sulfanedione; 2,2,2-trifluoroacetic acid To a solution of compound I-21a (232 mg, 0.5 mmol, 3-43) in DMF (5 mL) was added DIEA (202 mg, 1 mmol) and PhN(OTf)$_2$ (270 mg, 0.75 mmol) at 0° C. The solution was stirred at 0° C. for 2 hours and stirred at 25° C. for 12 hours. The mixture was concentrated to give the crude product which was purified by prep-HPLC (General procedure, Method 6) to give the intermediate I-22a as TFA salt (180 mg, 60.4%) as a yellow solid. ESI-MS (M+1): 597.3 calc. for C$_{28}$H$_{35}$F$_3$N$_4$C$_5$S.C$_2$HF$_3$O$_2$: 660.2.

Preparation of compound 14-01: 2-(5-methyl-2-furyl)-4-[(1-methyl-4-piperidyl)amino]-7-(3-pyrrolidin-1-ylpropoxy)quinoline-6-carbonitrile; 2,2,2-trifluoroacetic acid To a solution of intermediate I-22a (100 mg, 0.168 mmol) in DMF (5 mL) was added Zn(CN)$_2$ (39 mg, 0.336 mmol) and Pd (PPh$_3$)$_4$ (20 mg, Catalyst) and the solution was heated to 110° C. for 12 hours. Then, the solution was concentrated and extracted with EtOAc. The combined organic layer was washed with brine, dried over anhydrous Na$_2$SO$_4$ and concentrated to give the crude product which was purified by prep-HPLC (General procedure, Method 6) to give 14-01 as TFA salt (58 mg, 72.5%) as yellow solid. ESI-MS (M+1): 474.2 calc. for C$_{28}$H$_{35}$F$_3$N$_5$O$_2$.C$_2$HF$_3$O$_2$: 587.2; Rt is 1.68.

Synthetic Route 8

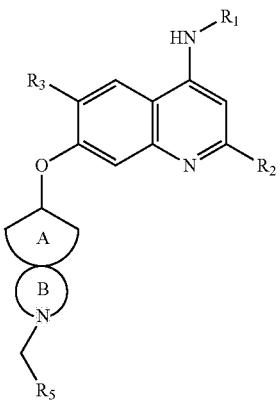

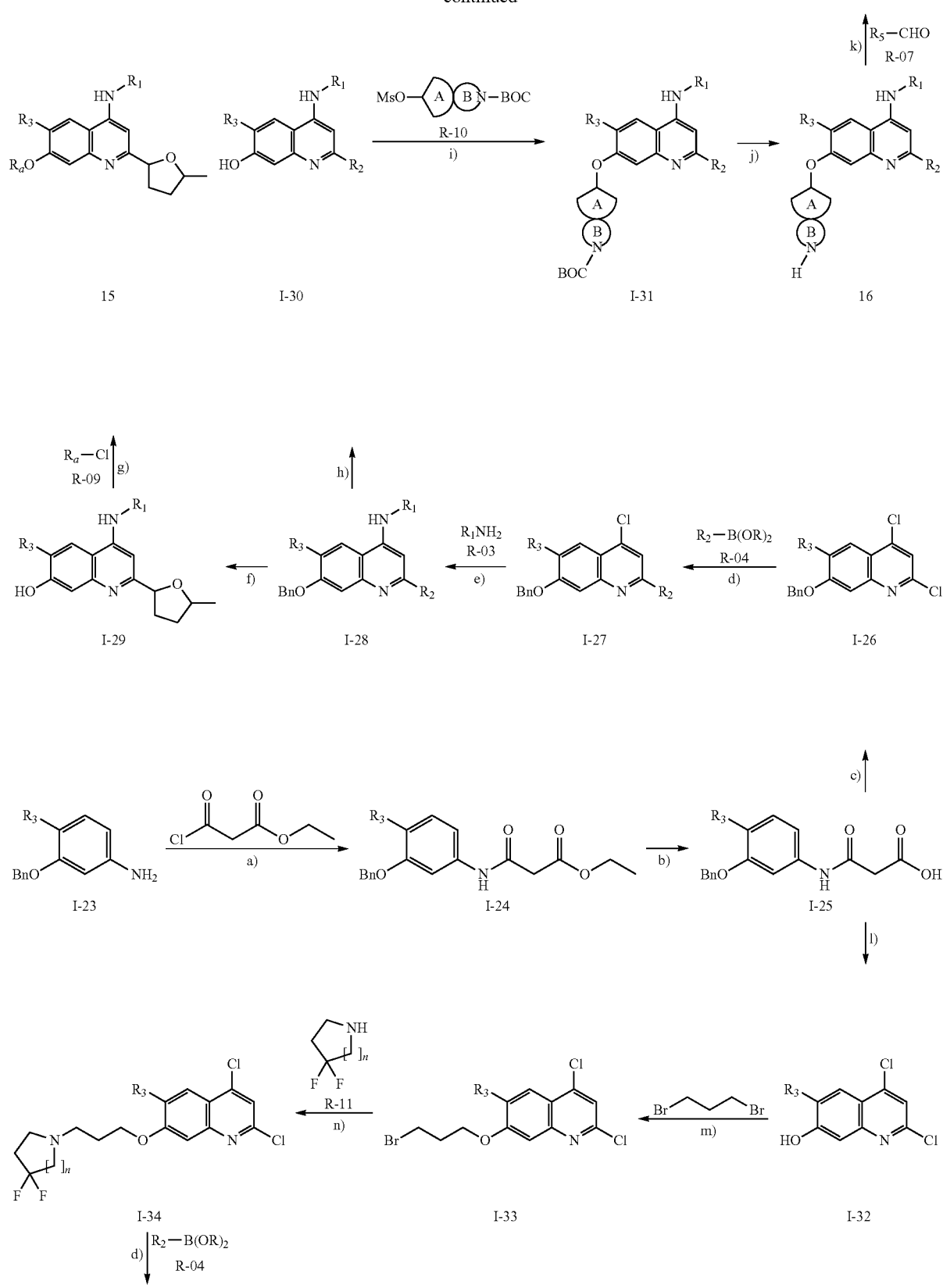

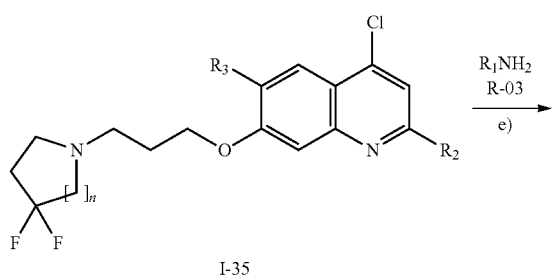 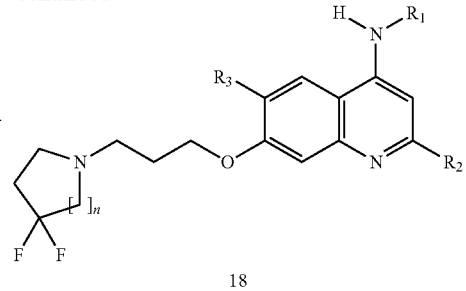

I-35 → 18

Conditions: a) Et₃N (2 eq), ethyl 3-chloro-3-oxo-propanoate (1.1 eq), DCM, 0° C., then 25° C., 12 h; b) LiOH·H₂O (1.5 eq), THF/MeOH/H₂O (3:3:2), 25° C., 16 h; c) POCl₃ (20 eq), 90° C., 2 h; d) R-04 (1.05 eq), K₂CO₃ (1.5 eq), Pd(PPh₃)₄ (0.1 eq), dioxane, 100° C., 16 h; e) R-03 (2 eq), Pd₂(dba)₃ (0.1 eq), Binap (0.1 eq), Cs₂CO₃ (2 eq), dioxane, 110-120° C., 16 h; f) Pd/C, H₂ (50 Psi), MeOH, 50° C., 16 h; g) R-09 (1.2 eq), Cs₂CO₃ (2 eq), DMF, 100° C., 16 h; h) Pd/C, H₂ (50 Psi), MeOH, 25° C., 16 h; i) R-10 (1.2 eq), Cs₂CO₃ (2 eq), DMF, 100° C., 16 h; j) HCl/EtOAc, 25° C., 2 h; k) R-07 (3 eq), NaBH(OAc)₃ (3 eq), HCOOH (1 eq), MeOH, 50-70° C., 16 h; l) POCl₃ (20 eq), 105° C., 4 h; m) 1,3-dibromopropane (1.2 eq), K₂CO₃ (2.5 eq), CH₃CN, 60° C., 88 h; n) R-11 (1.5 eq), K₂CO₃ (2 eq), CH₃CN, 50° C., 16-72 h.

In the scheme above $R_1$ is as previously defined; $R_2$ is aryl or heteroaryl; $R_3$ is H, Cl, OCF₃ or O(C₁-C₆)alkyl; $R^a$ is a hydrocarbon chain, which contains nitrogen and/or oxygen atoms and $R_5$ is H or (C₁-C₆)alkyl.

Preparation of Intermediate I-24a: ethyl 3-(3-benzyloxy-4-methoxy-anilino)-3-oxo-propanoate To the mixture of I-23a: 3-benzyloxy-4-methoxy-aniline (35 g, 0.153 mol) and TEA (30.87 g, 0.306 mol) in DCM (1 L) was added drop wise ethyl 3-chloro-3-oxo-propanoate (25.245 g, 0.168 mol) at 0° C. The mixture was stirred at 25° C. for 12 hours, poured into water (2 L) and extracted with DCM 2 times. The combined organic phase was dried with Na₂SO₄ and concentrated to dryness to afford I-24a (40 g, 76.3%). ESI-MS (M+1): 344.2 calc. for C₁₉H₂₁NO₅: 343.1.

Preparation of Intermediate I-25a: 3-(3-benzyloxy-4-methoxy-anilino)-3-oxo-propanoic acid To a mixture of intermediate I-24a (20.40 g, 59.41 mmol) in THF (100 mL), MeOH (100 mL) and H₂O (67 mL) was added LiOH·H₂O (3.74 g, 89.12 mmol) in one portion at 25° C. The mixture was stirred at 25° C. for 16 hours. LCMS showed the reaction was completed. Organic solvent was removed by rotary evaporation under vacuum at 45° C. The residue was poured into ice-water (w/w=1/1) (200 mL) and stirred for 10 min. The resulting slurry was filtered and the filter cake was dried under vacuum to afford I-25a (19.30 g, 61.21 mmol, crude) as a white solid. ESI-MS (M+1): 316.2 calc. for C₁₇H₁₇NO₅: 315.1.

Preparation of Intermediate I-26a: 7-benzyloxy-2,4-dichloro-6-methoxy-quinoline

Intermediate I-25a (7.00 g, 22.20 mmol) was suspended in POCl₃ (68.08 g, 443.99 mmol) in a 500 mL single-necked round bottom flask. The mixture was stirred at 90° C. for 2 hours under N₂. Then, the reaction mixture was cooled to 25° C. and concentrated to remove POCl₃. The residue was further purified by silica gel column chromatography (eluent gradient PE:EtOAc=50:1 to 10:1) to give I-26a (2.50 g, 33.69% yield). ESI-MS (M+1): 334.2 calc. for C₁₇H₁₃Cl₂NO₂: 333.0

Preparation of Intermediate I-27a: 7-benzyloxy-4-chloro-6-methoxy-2-(5-methyl-2-furyl)quinoline A solution of intermediate I-26a (900.00 mg, 2.69 mmol), 4,4,5,5-tetramethyl-2-(5-methyl-2-furyl)-1,3,2-dioxaborolane (R-04b) (588.32 mg, 2.83 mmol), K₂CO₃ (558.30 mg, 4.04 mmol) and Pd(PPh₃)₄ (311.19 mg, 269.30 umol) in dioxane (10 mL) was de-gassed and then heated to 100° C. for 16 hours under N₂. Then, the reaction mixture was poured into H₂O (50 mL). The mixture was extracted with ethyl acetate (40 mL×3). The organic phase was washed with saturated brine (40 mL), dried over anhydrous Na₂SO₄, concentrated in vacuum to give a residue, which was purified by column chromatography (eluent gradient PE:EtOAc=30:1 to 5:1) to afford I-27a (500.00 mg, 48.93% yield). ESI-MS (M+1): 380.1 calc. for C₂₂H₂₂ClNO₃: 379.1.

Preparation of Intermediate I-28a: 7-benzyloxy-6-methoxy-2-(5-methyl-2-furyl)-N-(1-methyl-4-piperidyl)quinolin-4-amine A solution of I-27a (500.00 mg, 1.32 mmol), 1-methylpiperidin-4-ylamine (R-03a) (300.63 mg, 2.63 mmol), Pd₂(dba)₃ (120.54 mg, 131.63 umol), BINAP (81.96 mg, 131.63 umol) and Cs₂CO₃ (857.78 mg, 2.63 mmol) in DIOXANE (10 mL) was de-gassed and then heated to 110° C. for 16 hours under N₂. Then, the reaction mixture was purified by column chromatography (DCM:MeOH=10:1) to afford I-28a (400.00 mg, 66.23% yield). ESI-MS (M+1): 458.2 calc. for C₂₈H₃₁N₃O₃: 457.2.

Preparation of Intermediate I-29a: 6-methoxy-4-[(1-methyl-4-piperidyl)amino]-2-(5-methyltetrahydrofuran-2-yl)quinolin-7-ol A mixture of I-28a (400.00 mg, 874.20 umol) and Pd/C (100.00 mg) in MeOH (20.00 mL) was stirred at 50° C. under H₂ (50 Psi) for 16 hours. Then, catalyst was removed by filtration and the filtrate was concentrated to dryness to give intermediate I-29a (300 mg, 92.38% yield) as a yellow solid. ESI-MS (M+1): 372.3 calc. for C₂₁H₂₉N₃O₃: 371.2.

Preparation of compound 15-01: 6-methoxy-N-(1-methyl-4-piperidyl)-2-(5-methyltetrahydrofuran-2-yl)-7-(3-pyrrolidin-1-ylpropoxy)quinolin-4-amine; 2,2,2-trifluoroacetic acid A mixture of I-29a (200.00 mg, 538.40 umol), 1-(3-chloropropyl)pyrrolidine (R-09a) (95.39 mg, 646.08 umol) and Cs₂CO₃ (350.84 mg, 1.08 mmol) in DMF (5.00 mL) was degassed and purged with N₂ for 3 times, and then the mixture was stirred at 100° C. for 16 hours under N₂ atmosphere. The mixture was concentrated to give a residue which was purified by prep-HPLC (General procedure, Method 1) to give compound 15-01 as TFA salt (50.00 mg, 19.24% yield) as a yellow oil. ESI-MS (M+1): 483.4 calc. for $C_{28}H_{42}N_4O_3.C_2HF_3O_2$: 596.3, Rt is 1.57.

Preparation of Intermediate I-30a: 6-methoxy-2-(5-methyl-2-furyl)-4-[(1-methyl-4-piperidyl)amino]quinolin-7-ol To a solution of I-28a (457.00 mg, 998.78 umol) in MeOH (50 mL) was added Pd/C (119.85 mg, 998.78 umol) under $N_2$. The suspension was degassed under vacuum and purged with $H_2$ several times. The mixture was stirred under $H_2$ (50 psi) at 25° C. for 16 hours. Then, the reaction mixture was filtered and the filter was concentrated. The crude product was purified by silica gel chromatography eluted with Petroleum ether/Ethyl acetate=5:1 to give I-30a (350.00 mg, 95.37% yield) as yellow solid. ESI-MS (M+1): 368.2 calc. for $C_{21}H_{25}N_3O_3$: 367.2.

Preparation of Intermediate I-31a: tert-butyl 6-[[6-methoxy-2-(5-methyl-2-furyl)-4-[(1-methyl-4-piperidyl)amino]-7-quinolyl]oxy]-2-azaspiro[3.3]heptane-2-carboxylate To a mixture of I-30a (100.00 mg, 272.15 umol) and tert-butyl 6-methylsulfonyloxy-2-azaspiro[3.3]heptane-2-carboxylate (R-10a) (95.15 mg, 326.58 umol) in DMF (5.00 mL) was added $Cs_2CO_3$ (177.35 mg, 544.31 umol) in one portion at 25° C. under $N_2$. The mixture was stirred at 100° C. for 16 hours. Then, the mixture was concentrated and purified by prep-TLC to give I-31a (60.00 mg, 39.18% yield). ESI-MS (M+1): 563.3 calc. for $C_{32}H_{42}N_4O_5$: 562.3.

Preparation of Intermediate I-31b: tert-butyl 2-[[6-methoxy-2-(5-methyl-2-furyl)-4-[(1-methyl-4-piperidyl)amino]-7-quinolyl]oxy]-7-azaspiro[3.5]nonane-7-carboxylate Intermediate I-31b was obtained in an analogous manner to intermediate I-31a using tert-butyl 2-methylsulfonyloxy-7-azaspiro[3.5]nonane-7-carboxylate (R-10b). 19% yield. ESI-MS (M+1): 591.3 calc. for $C_{34}H_{46}N_4O_5$: 590.3.

Preparation of compound 16-01: 7-(2-azaspiro[3.3]heptan-6-yloxy)-6-methoxy-2-(5-methyl-2-furyl)-N-(1-methyl-4-piperidyl)quinolin-4-amine; 2,2,2-trifluoroacetic acid I-31a (20.00 mg, 35.54 umol) was dissolved in HCl/EtOAc (5.00 mL) in a 50 mL single-necked round bottom flask. The mixture was stirred at 25° C. for 2 hours under $N_2$. Then, the mixture was concentrated purified by pre-HPLC (General procedure, Method 6) to give 16-01 as TFA salt (12.00 mg, 73% yield) as yellow solid. ESI-MS (M+1): 463.3 calc. for $C_{27}H_{34}N_4O_3.C_2HF_3O_2$: 576.2, Rt is 1.97.

Preparation of compound 16-02: 7-(7-azaspiro[3.5]nonan-2-yloxy)-6-methoxy-2-(5-methyl-2-furyl)-N-(1-methyl-4-piperidyl)quinolin-4-amine; 2,2,2-trifluoroacetic acid Compound 16-02 was obtained in an analogous manner to compound 16-01 starting from 1-31b. Purification by prep-HPLC (General procedure, Method 6), 72% yield. ESI-MS (M+1): 491.3 calc. for $C_{29}H_{38}N_4O_3.C_2HF_3O_2$: 604.3; Rt is 2.03.

Preparation of compound 17-01: 6-methoxy-7-[(2-methyl-2-azaspiro[3.3]heptan-6-yl)oxy]-2-(5-methyl-2-furyl)-N-(1-methyl-4-piperidyl)quinolin-4-amine; 2,2,2-trifluoroacetic acid A mixture of 16-01 (37.00 mg, 81.53 umol), $(HCHO)_n$ (R-07a) (22.03 mg, 244.58 umol), $NaBH(OAc)_3$ (51.84 mg, 244.58 umol) and HCOOH (3.92 mg, 81.53 umol) in MeOH (5.00 mL) was degassed and purged with $N_2$ for 3 times. The mixture was stirred at 70° C. for 16 hour under $N_2$ atmosphere. Then, the mixture was concentrated in vacuum to give a residue which was purified by prep-HPLC (General procedure, Method 1) to give 17-01 as TFA salt (9.00 mg, 23% yield) as a yellow solid. ESI-MS (M+1): 477.4 calc. for $C_{28}H_{36}N_4O_3.C_2HF_3O_2$: 590.2; Rt is 1.64.

Preparation of compound 17-02: 6-methoxy-7-[(7-methyl-7-azaspiro[3.5]nonan-2-yl)oxy]-2-(5-methyl-2-furyl)-N-(1-methyl-4-piperidyl)quinolin-4-amine; 2,2,2-trifluoroacetic acid Compound 17-02 was obtained in an analogous manner to compound 17-01 starting from 16-02. Purification by prep-HPLC (General procedure, Method 1), 15% yield. ESI-MS (M+1): 505.4 calc. for $C_{30}H_{40}N_4O_3.C_2HF_3O_2$: 618.3; Rt is 1.72.

Preparation of Intermediate I-32a: 2,4-dichloro-6-methoxy-quinolin-7-ol

Intermediate I-25a (7.00 g, 22.2 mmol) was suspended in $POCl_3$ (58.35 g, 380.57 mmol) in a 500 mL single-necked round bottom flask. The mixture was stirred at 105° C. for 4 hours under $N_2$. Then, the reaction mixture was cooled to 25° C. and concentrated to remove $POCl_3$. The residue was further purified by silica gel column chromatography (eluent gradient PE:EtOAc=50:1 to 10:1) to give 1-32a (1.40 g, 27.4% yield). ESI-MS (M+1): 244.1 calc. for $C_{10}H_7Cl_2NO_2$: 242.99.

Preparation of Intermediate I-33a: 7-(3-bromopropoxy)-2,4-dichloro-6-methoxy-quinoline To a solution of 1-32a (3 g, 12.29 mmol) and 1,3-dibromopropane (2.98 g, 14.75 mmol) in MeCN (60 mL) was added $K_2CO_3$ (4.25 g, 30.73 mmol). The mixture was stirred at 60° C. for 88 hours. Then, the reaction mixture was concentrated in vacuo to give a residue which was diluted with 100 mL water and filtered. The filter cake was concentrated in vacuum and further purified by silica gel column chromatography (eluted by PE:EtOAc=30:1—pure MeOH) to give intermediate I-33a (1 g, 22.29% yield) as a white solid. ESI-MS (M+1): 364.1 calc. for $C_{13}H_{12}BrCl_2NO_2$: 362.94.

Preparation of Intermediate I-34a: 2,4-dichloro-7-[3-(3,3-difluoropyrrolidin-1-yl)propoxy]-6-methoxy-quinoline To a solution of 1-33a (500 mg, 1.37 mmol) and 3,3-difluoropyrrolidine (R-11a) (220 mg, 2.06 mmol) in MeCN (50 mL) was added $K_2CO_3$ (378 mg, 2.74 mmol). The mixture was stirred at 50° C. for 88 hours. Then, the reaction mixture was concentrated in vacuum to give a residue which was partitioned between 100 mL DCM and 100 mL water. The organic phase was separated and aqueous phase was extracted with DCM (100 mL×3). The combined organic phase was dried over $Na_2SO_4$, filtered and concentrated in vacuo to give crude intermediate I-34a (600 mg, crude) as a gray solid which was used for next step without further purification. ESI-MS (M+1): 391.2 calc. for $C_{17}H_{18}Cl_2F_2N_2O_2$: 390.1.

Preparation of Intermediate I-34b: 2,4-dichloro-7-[3-(4,4-difluoro-1-piperidyl)propoxy]-6-methoxy-quinoline Intermediate I-34b was obtained in an analogous manner to intermediate I-34a using 4,4-difluoropiperidine (R-11 b). ESI-MS (M+1): 405.2 calc. for $C_{18}H_{20}Cl_2F_2N_2O_2$: 404.09.

Preparation of Intermediate I-35a: 4-chloro-7-[3-(3,3-difluoropyrrolidin-1-yl)propoxy]-2-(5-ethyl-2-furyl)-6-methoxy-quinoline A mixture of I-34a (600 mg, 1.53 mmol), 4,4,5,5-tetramethyl-2-(5-ethyl-2-furyl)-1,3,2-dioxaborolane (R-04r) (408 mg, 1.84 mmol), $K_2CO_3$ (529 mg, 3.83 mmol), $Pd(PPh_3)_4$ (177 mg, 153.00 umol) in dioxane (10 mL) and $H_2O$ (10 mL) was degassed and purged with $N_2$ for 3 times, and the mixture was stirred at 110° C. for 16 hrs under $N_2$ atmosphere. Then, the reaction mixture was extracted with DCM (50 mL×3). The combined organic phase was dried over $Na_2SO_4$, filtered and concentrated in vacuum to give a residue which was purified by silica gel column chromatography (eluted by PE:EtOAc=10:1~pure MeOH) to give intermediate I-35a (400 mg, 57.98% yield) as a brown solid. ESI-MS (M+1): 451.3 calc. for $C_{23}H_{25}ClF_2N_2O_3$: 450.15.

Preparation of Intermediate I-35b: 4-chloro-7-[3-(4,4-difluoro-1-piperidyl)propoxy]-2-(5-ethyl-2-furyl)-6-methoxy-quinoline Intermediate I-35b was obtained in an analogous manner to intermediate I-35a. 35% yield. ESI-MS (M+1): 465.3 calc. for $C_{24}H_{27}ClF_2N_2O_3$: 464.17.

Preparation of compound 18-01: 7-[3-(3,3-difluoro-pyrrolidin-1-yl)propoxy]-2-(5-ethyl-2-furyl)-6-methoxy-N-(1-methyl-4-piperidyl)quinolin-4-amine; 2,2,2-trifluoroacetic acid A mixture of I-35a (200 mg, 443.55 umol), 1-methyl-piperidin-4-ylamine (R-03a) (101 mg, 887.10 umol), $Pd_2(dba)_3$ (41 mg, 44.36 umol), BINAP (28 mg, 44.36 umol) and $Cs_2CO_3$ (289 mg, 887.10 umol) in dioxane (10 mL) was degassed and purged with $N_2$ for 3 times, and then the mixture was stirred at 120° C. for 16 hrs under $N_2$ atmosphere. Then, the reaction mixture was concentrated in vacuum to give a residue which was successively purified by prep-TLC (DCM:MeOH=10:1) and prep-HPLC (General procedure, Method 6) to give compound 18-01 as TFA salt (11 mg, 3.56%) as a white solid. ESI-MS (M+1): 529.4 calc. for $C_{29}H_{38}F_2N_4O_3 \cdot C_2HF_3O_2$: 642.2; Rt is 1.80.

Preparation of compound 18-02: 7-[3-(4,4-difluoro-1-piperidyl)propoxy]-2-(5-ethyl-2-furyl)-6-methoxy-N-(1-methyl-4-piperidyl)quinolin-4-amine; 2,2,2-trifluoroacetic acid Compound 18-02 was obtained in an analogous manner to compound 18-01 starting from 1-35b. Purification by prep-HPLC (General procedure, Method 6), 6.6% yield. ESI-MS (M+1): 543.4 calc. for $C_{30}H_{40}F_2N_4O_3 \cdot C_2HF_3O_2$: 656.3; Rt is 1.80.

Synthetic Route 9

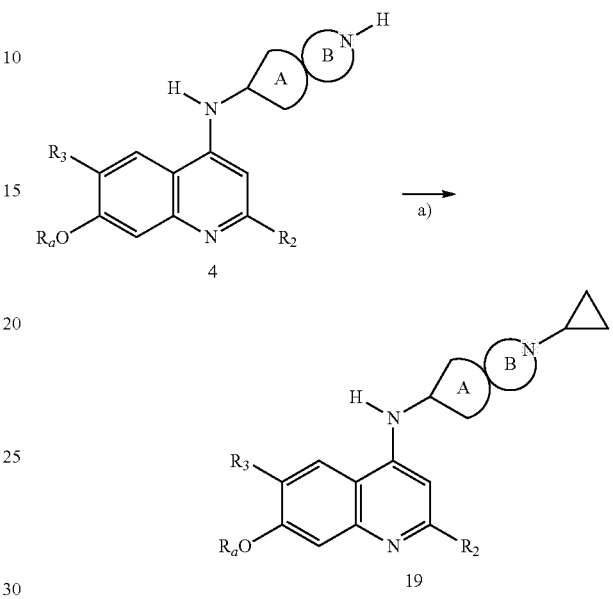

Conditions: a) (1-ethoxycyclopropoxy)-trimethyl-silane (6 eq), $NaBH_3CN$ (6 eq), AcOH (6 eq), MeOH, 60° C., 16 h.

In the scheme above $R_2$ is aryl or heteroaryl; $R_3$ is H, Cl, $OCF_3$ or $O(C_1-C_6)$alkyl and $R^a$ is a hydrocarbon chain, which contains nitrogen and/or oxygen atoms.

Preparation of compound 19-01: N-(7-cyclopropyl-7-azaspiro[3.5]nonan-2-yl)-2-(5-ethyl-2-furyl)-6-methoxy-7-(3-pyrrolidin-1-ylpropoxy)quinolin-4-amine; 2,2,2-trifluoroacetic acid To a solution of compound 4-03 (20.00 mg, 38.56 umol) in MeOH (10.00 mL) were added (1-ethoxycyclopropoxy)-trimethyl-silane (40.3 mg, 231.26 umol), $NaBH_3CN$ (14.54 mg, 231.36 umol) and AcOH (13.89 mg, 231.36 umol). The mixture was stirred at 60° C. for 16 hours. Then, the mixture was concentrated and the residue was purified by prep-HPLC (General procedure, Method 6) to give pure compound 19-01 as TFA salt (4.00 mg, 18.57% yield) as a yellow solid. ESI-MS (M+1): 559.4 calc. for $C_{34}H_{46}N_4O_3 \cdot C_2HF_3O_2$: 672.3; Rt is 1.95.

Preparation of compound 19-02: N-(7-cyclopropyl-7-azaspiro[3.5]nonan-3-yl)-2-(5-ethyl-2-furyl)-6-methoxy-7-(3-pyrrolidin-1-ylpropoxy)quinolin-4-amine; 2,2,2-trifluoroacetic acid Compound 19-02 was obtained in an analogous manner to compound 19-01 starting from 4-04. Purification by prep-HPLC (General procedure, Method 6), 54% yield. ESI-MS (M+1): 559.5 calc. for $C_{34}H_{46}N_4O_3 \cdot C_2HF_3O_2$: 672.3; Rt is 1.91.

Biological Tests

G9a Enzyme Activity Assay

The biochemical assay to measure G9a enzyme activity relies on time-resolved fluorescence energy transfer (TR- FRET) between europium cryptate (donor) and XL665 (acceptor). TR-FRET is observed when biotinylated histone monomethyl-H3K9 peptide is incubated with cryptate-labeled anti-dimethyl-histone H3K9 antibody (CisBio Cat#61KB2KAE) and streptavidin XL665 (CisBio Cat#610SAXLA), after enzymatic reaction of G9a. The human G9a enzyme expressed in a baculovirus infected Sf9 cell expression system was obtained from BPS Biosciences (Cat. #51001). Enzyme activity assay was carried out in a white 384-well plate in a final volume of 20 µl, as follow:

- 4 µl of vehicle or studied compound 2.5× concentrated prepared in assay buffer (50 mM Tris-HCl, 10 mM NaCl, 4 mM DTT, 0.01% Tween-20 pH9). Final percentage of DMSO was 0.5%.
- 2 µl of 1 nM G9a enzyme diluted in assay buffer. Final concentration was 0.2 nM.
- Start the reaction by adding 4 µl of substrate mixture containing 20 µM S-adenosylmethionine and 40 nM biotinylated histone monomethyl-H3K9 peptide.
- Reaction was carried out during 1 hour at room temperature.
- Enzyme activity was stopped by adding 5 µl of cryptate-labeled anti-dimethyl-histone H3K9 antibody. Final concentration 150 nM.
- Then, add 5 µl of streptavidin XL665 beads. Final concentration of 16 µM.
- Read the plate after 1 hour of incubation at room temperature.

For each well, fluorescence was measured at 620 nm and 665 nm. A ratio (665 nm/620 nm) was then calculated in order to minimize medium interferences. Positive control was obtained in the presence of the vehicle of the compounds. Negative control was obtained in the absence of G9a enzyme activity. Calculated $IC_{50}$ values were determined using GraphPrism using 4-parameters inhibition curve.

DNMT1 Enzyme Activity Assay

The biochemical assay to measure DNMT1 enzyme activity relies on time-resolved fluorescence energy transfer (TR-FRET) between lumi4-Tb (donor) and d2 (acceptor) using the EPIgeneous methyltransferase assay (CisBio Cat#62SAHPEB). TR-FRET is observed when antibody specific to S-adenosylhomocysteine labeled with Lumi4-Tb is incubated with d2-labeled S-adenosylhomocysteine. TR-FRET signal is inversely proportional to the concentration of SAH, product of DNMT1 enzyme activity, in the sample.

The human DNMT1 was obtained from Reaction Biology Corp. (Cat# DMT-21-124). Enzyme activity assay was carried out in a white 384-well plate in a final volume of 20 µl, as follow:

- 4 µl of vehicle or studied compound 2.5× concentrated prepared in assay buffer (50 mM Tris-HCl, 1 mM EDTA, 1 mM DTT, 0.1% Triton X-100, 5% glycerol pH 7.5). Final percentage of DMSO was 0.5%.
- 2 µl of 1 nM DNMT1 enzyme diluted in assay buffer. Final concentration was 20 nM.
- Start the reaction by adding 4 µl of substrate mixture containing 1 µM S-adenosylmethionine and 1 µM poly-deoxy inosine poly-deoxy cytosine (pdI-pdC) DNA.
- Reaction was carried out during 15 minutes at 37° C.
- Enzyme activity was stopped by adding 2 µl of buffer one of the EPIgeneous methyltransferase assay.
- After 10 minutes at room temperature, it was added 4 µl of antibody specific to S-adenosylhomocysteine labeled with Lumi4-Tb 50× diluted in buffer two of the EPIgeneous methyltransferase assay.
- Add 4 µl of d2-labeled S-adenosylhomocysteine 31× diluted in buffer two of the EPIgeneous methyltransferase assay.
- Read the plate after 1 hour of incubation at room temperature.

For each well, fluorescence was measured at 620 nm and 665 nm. A ratio (665 nm/620 nm) was then calculated in order to minimize medium interferences. Positive control was obtained in the presence of the vehicle of the compounds. Negative control was obtained in the absence of G9a enzyme activity. Calculated IC50 values were determined using GraphPrism using 4-parameters inhibition curve.

DNMT3A and DNMT3B Enzyme Activity Assay

DNMT3A and DNMT3B activity assays were carried out with the chemiluminiscence BPS DNMT Universal Assay Kit (BPS#52035) using a strip 96-well plate pre-coated with DNMT substrate.

The enzyme activity assay protocol is as follows:

- Rehydrate the microwells by adding 150 µL of TBST buffer (1× Tris-buffered saline (TBS), pH 8.0, containing 0.05% Tween-20) to every well. Incubate 15 minutes at room temperature.
- Dilute each purified DNMT [DNMT3A/3L (BPS#51106) or DNMT3B/3L (BPS#51109)] in 1×DNMT assay buffer 2 (BPS#52201) at 5-10 ng/µL. Keep diluted enzyme on ice until use.
- Prepare 50 µL of reaction mixture consisting of 20 µL of DNMT (5-10 ng/µL), 12.5 µL of 4×DNMT assay buffer 2 (BPS#52201), 2.5 µL of S-adenosylmethionine 400 µM, test compound at concentrations ranging from 3 nM to 10 µM and $H_2O$ up to 50 µL.
- Add the entire reaction mixture to the substrate coated wells. Incubate at 37° C. for 120 minutes.
- Wash the wells three times with TBST buffer.
- Add 100 µL of Blocking buffer (BPS#52100) to every well. Shake on a rotating platform for 10 min. Remove supernatant.
- Dilute first antibody against 5-methylcytosine (Anti-5-methylcytosine by BPS) 400-fold with Blocking buffer and add 100 µL per well. Incubate 1 hour at room temperature with slow shaking.
- Wash plate three times with TBST buffer and incubate in Blocking buffer shaking on a rotating platform for 10 min. Remove supernatant.
- Dilute secondary antibody (secondary HRP-labeled antibody 1(BPS#52130H)) 1000-fold with Blocking buffer and add 100 µL per well.
- Incubate for 30 min at room temperature with slow shaking.
- Wash plate three times with TBST buffer and incubate in Blocking buffer shaking on a rotating platform for 10 min. Remove supernatant.
- Just before use, mix on ice 50 µL HRP chemiluminescent substrate A (BPS) and 50 µL HRP chemiluminescent substrate B (BPS) and add 100 µL per well. Immediately read luminescence using a BioTek Synergy™2 microplate reader.

The chemiluminescence intensity data were analyzed and compared. Positive control was obtained in the absence of the compounds. Negative control was obtained in the absence of DNMT enzymes. Calculated IC50 values were determined using non-linear regression analysis of Sigmoidal dose-response curve generated with a four-parameters inhibition curve.

Table 2 shows the inhibition values for G9a and DNMTs ($IC_{50}$) for selected compounds; where 1 µM≤$IC_{50}$≤10 µM (+), 500 nM $IC_{50}$≤1 µM (++), 100 nM≤$IC_{50}$<500 nM (+++) and $IC_{50}$<100 nM (++++).

TABLE 2

| Compound | G9a IC50(M) | DNMT1 IC50(M) | DNMT3A IC50(M) | DNMT3B IC50(M) |
|---|---|---|---|---|
| 1-02 | ++++ | ++ | | |
| 2-01 | +++ | + | | |
| 3-02 | + | ++ | | |
| 3-04 | ++++ | +++ | ++++ | +++ |
| 3-05 | ++ | + | | |
| 3-06 | +++ | + | | |
| 3-07 | ++++ | ++++ | ++++ | ++ |
| 3-08 | ++++ | +++ | | |
| 3-10 | +++ | ++ | | |
| 3-11 | +++ | + | | |
| 3-12 | +++ | + | | |
| 3-13 | ++ | ++ | | |
| 3-14 | + | + | | |
| 3-16 | +++ | + | | |
| 3-17 | +++ | ++ | | |
| 3-18 | +++ | + | | |
| 3-19 | +++ | + | | |
| 3-20 | ++++ | +++ | | |
| 3-21 | ++ | ++ | | |
| 3-23 | ++++ | ++ | | |
| 3-24 | ++++ | + | | |
| 3-25 | + | + | | |
| 3-27 | ++++ | + | | |
| 3-28 | ++++ | ++ | | |
| 3-29 | ++++ | + | | |
| 3-30 | ++++ | + | | |
| 3-31 | ++++ | +++ | | |
| 3-32 | + | + | | |
| 3-33 | ++++ | + | | |
| 3-34 | ++++ | + | | |
| 3-35 | ++++ | ++ | | |
| 3-36 | ++++ | ++ | | |
| 3-37 | +++ | + | | |
| 3-38 | ++++ | +++ | | |
| 3-39 | ++++ | ++++ | | |
| 3-40 | ++++ | +++ | | |
| 3-41 | ++++ | +++ | | |
| 3-42 | ++++ | +++ | | |
| 3-43 | ++ | ++ | | |
| 4-01 | ++++ | +++ | | |
| 4-02 | ++++ | + | | |
| 5-01 | ++++ | +++ | | |
| 5-02 | ++++ | +++ | | |
| 5-03 | ++++ | +++ | | |
| 5-04 | ++++ | +++ | | |
| 5-05 | ++++ | +++ | | |
| 6-01 | ++++ | +++ | | |
| 6-02 | ++++ | ++ | | |
| 7-01 | ++++ | +++ | | |
| 7-02 | ++++ | + | | |
| 8-01 | +++ | + | | |
| 8-02 | ++++ | ++ | | |
| 9-01 | ++++ | ++ | | |
| 10-01 | +++ | + | | |
| 11-01 | ++ | ++++ | | |
| 14-01 | + | ++ | | |
| 13-01 | ++ | ++ | | |
| 19-03 | + | + | | |
| 3-45 | +++ | + | | |
| 11-02 | +++ | +++ | | |
| 4-03 | ++++ | ++++ | | |
| 3-46 | +++ | +++ | | |
| 11-03 | + | ++ | | |
| 11-04 | + | +++ | | |
| 11-05 | ++++ | +++ | | |
| 11-06 | +++ | +++ | | |
| 11-07 | ++ | ++ | | |
| 11-08 | + | + | | |
| 11-09 | +++ | +++ | | |
| 16-01 | + | +++ | | |
| 11-10 | + | +++ | | |
| 12-03 | + | +++ | | |
| 3-47 | + | + | | |
| 11-11 | ++ | ++ | | |
| 12-04 | + | ++ | | |
| 3-48 | ++++ | +++ | | |
| 3-49 | +++ | +++ | | |
| 5-06 | ++++ | +++ | | |
| 19-01 | + | ++ | | |
| 15-01 | ++++ | + | | |
| 17-01 | +++ | ++++ | | |
| 3-50 | ++++ | +++ | | |
| 19-02 | ++ | +++ | | |
| 7-05 | ++++ | ++ | | |
| 3-51 | ++++ | +++ | | |
| 5-07 | ++++ | +++ | | |
| 3-52 | +++ | + | | |
| 3-53 | ++ | +++ | | |
| 3-54 | ++++ | +++ | | |
| 3-55 | + | +++ | | |
| 7-04 | ++++ | ++ | | |
| 3-56 | +++ | +++ | | |

Compounds in Table 2 are capable of inhibiting G9a as well as one or more DNMTs, selected from the group DNMT1, DNMT3A and DNMT3B, with $IC_{50}$ values≤10 µM.

Cell Proliferation Assay

Cell proliferation was analyzed after 48 hours of in vitro treatment using the CellTiter 96 Aqueous One Solution Cell Proliferation Assay (Promega, Madison, Wis.). This is a colorimetric method for determining the number of viable cells in proliferation.

For the assay, suspension cells were cultured by triplicate at a density of 1×10⁶ cells/ml in 96-well plates (100.000 cells/well, 100 µl/well), except for OCILY-3 and OCILY-10 cell lines which were cultured at a density of 0.5×10⁶ cells/ml (50.000 cells/well, 100 µl/well) and for HepG2, Hep3B and PLC/PRF/5 cell ines which were cultured at a density of 3000 cells/well, 100 µl/well). Adherent cells were obtained from 80-90% confluent flasks and 100 µl of cells were seeded at a density of 5000 cells/well in 96-well plates by triplicate. Before addition of the compounds, adherent cells were allowed to attach to the bottom of the wells for 12 hours. In all cases, only the 60 inner wells were used to avoid any border effects.

After 48 hours of treatment, plates with suspension cells were centrifuged at 800 g for 10 minutes and medium was removed. The plates with adherent cells were flicked to remove medium. Then, cells were incubated with 100 ul/well of medium and 20 ul/well of CellTiter 96 Aqueous One Solution reagent. After 1-3 hours of incubation at 37° C., absorbance was measured at 490 nm in a 96-well plate reader. The background absorbance was measured in wells with only cell line medium and solution reagent. Data was calculated as a percentage of total absorbance of treated cell/absorbance of non treated cells.

Table 3 shows the functional response of selected compounds on established cell lines and primary cultures ($GI_{50}$); where, $GI_{50}$≤10 µM (+), 1 µM≤$GI_{50}$≤10 µM (++), 100 nM≤$GI_{50}$<1 µM (+++) and $GI_{50}$<100 nM (++++). These cancer cell lines and primary cultures correspond to acute lymphocytic leukemia (ALL), CEMO-1 and LAL-CUN-2, to activated B-cell-like diffuse large B-cell lymphoma (ABC-DLBCL), OCI-Ly3 and OCI-Ly10 and to hepatocellular carcinoma cells (HCC), HepG2, Hep3B and PLC/PRF/5.

TABLE 3

| Example | CEMO-1 | LAL-CUN-2 | OCI-Ly3 | OCI-Ly10 | HEPG2 | HEP3B | PLC/PRF/5 |
|---|---|---|---|---|---|---|---|
| 3-04 | +++ | +++ | +++ | +++ | +++ | +++ | +++ |
| 3-05 | +++ | | | | | | |
| 3-07 | ++++ | +++ | +++ | ++++ | +++ | +++ | +++ |
| 3-08 | ++ | ++ | ++ | + | | | |
| 3-17 | + | | +++ | +++ | | | |
| 3-19 | ++ | | +++ | +++ | + | ++ | ++ |
| 3-20 | +++ | ++ | +++ | +++ | +++ | +++ | +++ |
| 3-24 | | | | ++ | | | |
| 3-27 | ++ | + | + | +++ | | | |
| 3-28 | ++ | | | ++++ | | | |
| 3-29 | +++ | | +++ | +++ | ++ | ++ | ++ |
| 3-31 | ++ | + | +++ | +++ | | | |
| 3-36 | +++ | | | | | | |
| 3-39 | +++ | | | | | | |
| 3-40 | ++++ | +++ | ++++ | ++++ | | | |
| 3-41 | ++++ | +++ | ++++ | ++++ | +++ | +++ | +++ |
| 5-01 | +++ | | +++ | +++ | | | |
| 5-02 | +++ | | +++ | +++ | ++ | ++ | ++ |
| 5-03 | +++ | ++ | +++ | +++ | | | |
| 5-04 | +++ | ++ | +++ | +++ | | | |
| 6-01 | ++ | ++ | | | | | |
| 3-42 | ++++ | +++ | +++ | +++ | ++++ | +++ | +++ |
| 5-05 | ++ | | | | | | |
| 11-01 | ++ | | ++++ | ++ | ++ | ++ | ++ |
| 11-02 | ++ | | | | | | |
| 4-03 | ++ | | | | | | |
| 12-02 | +++ | | +++ | +++ | ++ | ++ | ++ |
| 11-05 | + | | | + | + | + | + |
| 16-01 | ++ | | | | + | + | + |
| 12-03 | +++ | | ++++ | +++ | +++ | +++ | +++ |
| 3-48 | +++ | | ++ | +++ | ++ | ++ | + |
| 3-49 | +++ | | ++++ | +++ | +++ | +++ | +++ |
| 5-06 | +++ | | +++ | +++ | +++ | +++ | +++ |
| 17-01 | ++++ | | ++++ | +++ | +++ | +++ | +++ |
| 3-50 | +++ | | +++ | ++ | ++ | ++ | +++ |
| 7-05 | + | | | | + | + | + |
| 3-51 | +++ | | ++ | +++ | +++ | +++ | +++ |
| 5-07 | +++ | | ++++ | +++ | +++ | +++ | +++ |
| 3-53 | +++ | | | | | | |
| 3-54 | +++ | | | | | | |
| 3-56 | +++ | | | | | | |

Compounds in Table 3 inhibit proliferation of acute lymphocytic leukemia (ALL), activated B-cell-like diffuse large B-cell lymphoma (ABC-DLBCL) and hepatocarcinoma (HCC) cell lines.

Compounds 3-04 and 3-07 were tested against different solid tumour and oncohematological cell lines using the cell proliferation protocol described above.

Table 4 (where GC-DLBCL stands for germinal centre B-cell-like diffuse large B-cell lymphoma, AML stands for acute myeloid leukemia, MCL stands for mantle cell lymphoma and MM stands for multiple myeloma) shows the functional response on different cell lines ($GI_{50}$) for compounds 3-04 & 3-07; where, $GI_{50}>10$ μM (+), 1 μM≤$GI_{50}$≤10 μM (++), 100 nM<$GI_{50}$≤1 μM (+++) and $GI_{50}$≤100 nM (++++).

TABLE 4

| cell_line | Cancer Type | Compound 3-04 | Compound 3-07 |
|---|---|---|---|
| MGH-U3 | Bladder | +++ | +++ |
| MGH-U4 | Bladder | +++ | +++ |
| RT112 | Bladder | +++ | +++ |
| UM-UC-7 | Bladder | +++ | +++ |
| MCF-7 | Breast | +++ | ++ |
| HELA | Cervical | +++ | +++ |
| COLO-205 | Colorectal | +++ | +++ |
| HCT-116 | Colorectal | +++ | +++ |
| LOVO | Colorectal | ++ | +++ |
| U87-MG | Glioblastoma | +++ | +++ |
| HUH7 | Hepatocarcinoma | ++++ | +++ |
| Sk-Hep1 | Hepatocarcinoma | +++ | +++ |
| 1205-LU | Melanoma | +++ | ++++ |
| 451-LU | Melanoma | +++ | ++++ |
| A375 | Melanoma | +++ | ++++ |
| SK-MEL-103 | Melanoma | +++ | ++++ |
| SK-MEL-147 | Melanoma | +++ | ++++ |
| UACC-62 | Melanoma | +++ | +++ |
| WM-35 | Melanoma | +++ | +++ |
| SU8686 | Pancreas | ++ | +++ |
| DU145 | Prostate | +++ | +++ |
| PC3 | Prostate | +++ | +++ |
| A498 | Renal | + | +++ |
| CAKI-2 | Renal | ++ | +++ |
| HCC95 | small-cell lung cancer | +++ | +++ |
| H460 | non-small-cell lung cancer | +++ | +++ |
| OCI-Ly1 | GC-DLBCL | +++ | |
| OCI-Ly7 | GC-DLBCL | +++ | |
| SU-DHL-7 | GC-DLBCL | +++ | |
| PEER | ALL | +++ | |
| OCI-AML-2 | AML | +++ | +++ |
| MV411 | AML | +++ | +++ |
| MOLM-13 | AML | +++ | ++ |
| HBL-2 | MCL | +++ | |
| KMS28BM | MM | ++ | |

Compounds in Table 4 inhibit proliferation of different solid tumour and oncohematological cell lines.

Table 5. shows the comparison of selected compounds (dual G9a-DNMT) with selective G9a (BIX12094 and UNC0638) and DNMT inhibitors (5-azacytidine and decitabine) on established cell lines and primary cultures ($GI_{50}$); where, $GI_{50}≥10$ μM (+), 1 μM≤$GI_{50}$≤10 μM (++), 100 nM≤$GI_{50}$<1 μM (+++) and $GI_{50}$<100 nM (++++). These cancer cell lines and primary cultures correspond to acute lymphocytic leukemia (ALL), CEMO-1 and LAL-CUN-2, to acute myeloid leukemia (AML): OCI-AML-2 and MV4-11 and to multiple myeloma (MM): $JJN_3$ and U266.

TABLE 5

| Test Compound | CEMO-1 | LAL-CUN-2 | OCI-AML-2 | MV4-11 | JJN3 | U266 |
|---|---|---|---|---|---|---|
| BIX 12094 | ++ | ++ | ++ | + | + | + |
| UNC0638 | ++ | ++ | ++ | + | + | + |
| Compound 3-04 | +++ | +++ | +++ | +++ | ++ | ++ |
| Compound 3-07 | ++++ | +++ | +++ | +++ | ++ | ++ |
| 5-azacytidine | ++ | + | + | ++ | + | ++ |
| Decitabine | +++ | + | + | + | + | + |

Dual compounds 3-04 and 3-07 are more potent inhibitors of cell proliferation than the selective G9a inhibitors (BIX12094 and UNC0638) and DNMT inhibitors (5-azacytidine and decitabine).

Evaluation of In Vivo Therapeutic Activity in the Preclinical Human B-ALL Mice Model with CEMO-1 Cell Line.

To examine the in vivo activity, a preclinical model of human B-ALL with RAG2 mouse was used. Six to eight-week old female BALB/cA-Rag2$^{-/-}$γc$^{-/-}$ mice were purchased from The Netherlands Cancer Institute and maintained in pathogen-free isolation cages. RAG2 mice were injected intravenously (i.v.) with 10×10$^6$ CEMO-1 cells via tail vein to generate the human B-ALL mice model. Animals in groups of six were treated starting at day three after cells inoculation. The first group served as control and received placebo (saline) daily for 28 consecutive days, via i.v. injection.

Results with Compound 3-04:

The second group was treated with 3-04 (2.5 mg/kg) daily for 28 consecutive days via i.v. Animals were monitored weekly for weight loss and signs of tumour burden by flow cytometry of human cells. The median survival for 3-04 treated mice (N=6) was 91 days (SD: ±5.72) compared to 57 days (SD: ±10.52) for control mice (N=6) after cells inoculation. The treatment significantly prolonged survival of this group compared with the control (P=0.0009), as determined by the Kaplan-Meier method with log-rank test calculated with the statistical software MedCalc (FIG. 1).

Reprogramming Method with Lentiviral Vectors

The used reprogramming system consisted in four independent doxycycline inducible lentiviral vectors (FUW-Tet-O based vectors) coding for the human OCT4 (addgene, ref#20726), SOX2 (addgene, ref#20724), KLF4 (addgene, ref#20725) and cMYC (addgene, ref#20723) transcription factors (O:S:K:M) Vesicular Stomatitis Virus G (VSVG)-coated lentiviruses were generated in 293T cells as described previously (Tiscornia et al., Nat Protoc. 2006; 1(1):241-5.). Briefly, 293T cells (ATCC, CRL-3216) were transfected with FUW-TetO lentiviral vectors referred above along with packaging plasmids psPAX2 (addgene, ref#12260) and pMD2.G (addgene, ref#12259) under the same conditions as those disclosed by Tiscornia et al, supra. Fibroblast culture medium (FCM) (Dulbecco's Modified Eagle Medium (DMEM) (Sigma), 10% fetal bovine serum (FBS) (Gibco), 100 U/mL Penicillin/Streptomycin P/S (Lonza), 2 mM L-glutamine (Lonza), 0.1 mM non-essential amino acid (NEAA) (Lonza)) was replaced with fresh medium 12 h posttransfection and virus-containing supernatants were collected 60-72 h posttransfection and filtered through a 0.45 µm filter Virus-containing supernatants were pooled for 4 factor infections and supplemented with FUW-M2rtTA virus (addgene, ref#20342) in a ratio 2:2:2:2:1 (OCT4:SOX2:KLF4:cMYC:rtTA virus) in fresh FCM.

Once lentiviral vectors were obtained the following reprogramming protocol was performed for BJ human fibroblasts:

Day 0: Plate BJ cells (ATCC, CRL-2522) ($10^6$ cells in 75 $cm^2$ culture flask) in FCM.

Day 1: First infection of BJ cells with a combination of FUW-Tet-O vectors (Multiplicity of Infection, MOI=5) in the presence of 4 µg/mL of polybrene (Sigma).

Day 2: Second infection of BJ cells (same conditions that first infection).

Day 3: Replate BJ cells in 2×175 $cm^2$ culture flask in fresh FCM.

Day 4: Incubate 1×175 $cm^2$ flask with 0.2 µM or 0.1 µM of test compound and the other flask just with FCM. Compound concentrations were selected according to the determined GI50 in BJ human fibroblasts, in order to avoid cytotoxicity.

Day 6: Replate BJ cells on p100 culture dishes previously seeded with mouse embryonic fibroblast (MEF) feeder layers (25000 cells/$cm^2$) prepared in-house at different densities: $5×10^4$, $10^5$ and $5×10^5$ cells/plate in FCM+doxycycline 1 µg/mL (Clontech).

Mouse embryonic fibroblasts (MEFs) were produced as described (Takahashi, K. et al., Cell 2006, 126, 663-676). Briefly mouse embryos isolated from 12.5-14.5 day-pregnant C57BL/6 (Harlan) mice (6-8 week) were washed with PBS and the head and visceral tissues were removed. The remaining bodies were washed in fresh PBS, minced using a pair of scissors, transferred into 3 mL of 0.1 mM trypsin/1 mM EDTA solution (Lonza) per embryo and incubated at 37° C. for 10 min. After incubation, an additional 3 mL per embryo of 0.1 mM trypsin/1 mM EDTA solution was added, and the mixture was incubated at 37° C. for 10 min. After trypsinization, an equal amount of medium (6 mL per embryo DMEM (Sigma) containing 10% FBS (Gibco)) was added and pipetted up and down a few times to help with tissue dissociation. Supernatant was transferred into a new tube and cells were collected by centrifugation and resuspended in fresh medium. Cells were seeded in approximately ten 100-mm dishes in FCM. MEFs at passage 3 were irradiated at 50 Gy in a GammaCell irradiator (Gammacell 3000 Serial #375 Irradiator, MDS Nordion).

Day 8: Change culture media to iPSC culture media (DMEM-KO (Gibco), 20% Knockout Serum Replacement (KSR) (Gibco), 100 U/mL P/S (Lonza), 2 mM L-glutamine (Lonza), 0.1 mM NEAA (Lonza), 0.1 mM β-mercaptothanol (Gibco) and 5 ng/mL basic Fibroblast Growth Factor (bFGF) (Peprotech))+doxycycline 1 µg/mL and valproic acid 1 mM (VPA) (Sigma).

Day 10 until 30: Change every other day spent media with new iPSC culture media+doxycycline 1 µg/mL and VPA 1 mM.

NOTE: VPA is only added during the first week of reprogramming.

Reprogramming Method with Retroviral Vectors

The retroviral reprogramming system consisted in two independent retroviral vectors (pMXs based vectors) coding for the human OCT4 (addgene, ref#17217) and SOX2 (addgene, ref#17218) transcription factors (O:S). VSVG-coated retroviruses were generated in 293T cells as described previously (Takahashi K. et al., Cell 2007, 131, 861-872). Briefly, 293T cells (ATCC, CRL-3216) were transfected with pMXs-retroviral vectors referred above along with packaging plasmids pUMCV (encoding gag-pol, addgene, ref#8449) and pCMV-VSV.G (addgene, ref#8454), under the same conditions as those disclosed by Takahashi et al, supra. FCM was replaced with fresh medium 12 h posttransfection. Virus-containing supernatants were collected 60-72 h posttransfection and were filtered through a 0.45 µm filter. Virus-containing supernatants were pooled for 2 factor infections in a ratio 2:1: (O:S) in fresh FCM.

Once retroviral vectors were obtained the following reprogramming protocol was performed for BJ human fibroblasts:

Day 0: Plate BJ cells (ATCC, CRL-2522) ($10^6$ cells in 75 $cm^2$ culture flask) in FCM.

Day 1: First infection of BJ cells with a combination of pMXs vectors (MOI=5) in the presence of 4 µg/mL of polybrene.

Day 2: Second infection of BJ cells (same conditions that first infection).

Day 3: Third infection of BJ cells (same conditions that first infection). FCM was replaced with fresh medium 12 h after the infection.

Day 4: Twenty-four hours after last infection replace FCM by fresh media containing test compound at 0.2 µM.

Day 6: Replate BJ cells on MEF feeder layers prepared in-house at different densities: $5×10^4$, $10^5$ and $5×10^5$ cells/plate in FCM.

Day 8: Change FCM to iPSC media and VPA 1 mM.

Day 10 until 30: Change every other day spent media with new iPSC culture media and VPA 1 mM.

NOTE: VPA is only added during the first week of reprogramming.

Reprogramming Efficiency Quantification.

Reprogramming efficiency was quantified four weeks after infection. Presence of ESC-like colonies was detected by alkaline phosphatase (AP) staining using Leukocyte Alkaline Phosphatase Kit (Sigma) according to the manufacturer's protocol. Efficiency was calculated according to the following formula:

E(%)=(No. AP⁺colonies)*100/(No. cells plated on MEFs)

Fold increase in reprogramming efficiency was calculated using the ratio between the No. of AP⁺ colonies obtained after infection of the BJ with the different transcription factors (TF)-treated with Compound 3-04 versus untreated groups.

iPS Generation Results:

Reprogramming method with lentiviral vectors (O:S:K:M):

| Test Compound | Compound Concentration (nM) | Folding respect to untreated |
|---|---|---|
| BIX12094 | 200 | 1.29 |
| UNC0638 | 200 | 1.22 |
| Compound 3-04 | 200 | 2.73 |
| Compound 3-04 | 100 | 1.58 |

Reprogramming method with retroviral vectors (O:S):

| Test Compound | Compound Concentration (nM) | Folding respect to untreated |
|---|---|---|
| BIX12094 | 200 | 1.04 |
| Compound 3-04 | 200 | 1.95 |

Reprogramming efficiency in BJ cells was clearly increased when reprogramming process was carried out in the presence of Compound 3-04. In particular, incubation of BJ cells with this compound allowed the appearance of higher number of ESC-like colonies. This increase in the reprogramming efficiency was also observed when only 2 factors were used for cell reprogramming, indicating that Compound 3-04 could be useful for high-quality iPSC generation.

REFERENCES CITED IN THE APPLICATION

Shankar S R. et al., "*G9a, a multipotent regulator of gene expression*". Epigenetics, 2013. 8(1): p. 16-22.

Vilas-Zornoza A. et al., "*Frequent and Simultaneous Epigenetic Inactivation of TP53 Pathway Genes in Acute Lymphoblastic Leukemia*" PLoS ONE, 2011. 6(2): p. e17012.

Rotili D. et al., "*Properly Substituted Analogues of BIX-01294 Lose Inhibition of G9a Histone Methyltransferase and Gain Selective Anti-DNA Methyltransferase 3A Activity*", PLoS ONE, 2014. 9(5): p. E96941.

Vedadi M. Et al., "*A chemical probe selectively inhibits G9a and GLP methyltransferase activity in cells*", Nat. Chem. Biol. 2011, 7, pp. 566-574.

Liu F. et al., "*Discovery of an in vivo chemical probe of the lysine methyltransferases G9a and GLP*", J. Med. Chem. 2013, 56(21), pp. 8931-42.

Jung D W. et al., "*Reprogram or Reboot: Small Molecule Approaches for the Production of Induced Pluripotent Stem Cells and Direct Cell Reprogramming*" ACS Chem. Biol, 2014. 9(1): p. 80-95.

Shi Y. et al., "*Induction of pluripotent stem cells from mouse embryonic fibroblasts by Oct4 and Klf4 with small-molecule compounds*", Cell Stem Cell 2008, 3, pp. 568-574.

Giardina G. et al., "*Discovery of a Novel Class of Selective Non-Peptide Antagonists for the Human Neurokinin-3 Receptor 1. Identification of the 4-Quinolinecarboxamide Framework*", Journal of Medicinal Chemistry 1997, 40(12), pp. 1794-1807.

Drake N. et al., "*Synthetic Antimalarials. The Preparation of Certain 4-Aminoquinolines*", Journal of the American Chemical Society 1946, 68, pp. 1208-13.

Tiscornia G. et al., "*Production and purification of lentiviral vectors*". Nat Protoc. 2006, 1(1), pp 241-5.

Takahashi K. et al., "*Induction of Pluripotent Stem Cells from Mouse Embryonic and Adult Fibroblast Cultures by Defined Factors*" Cell 2006, 126, pp. 663-676.

Takahashi K. et al., "*Induction of Pluripotent Stem Cells from Adult Human Fibroblasts by Defined Factors*" Cell 2007, 131, pp. 861-872.

The invention claimed is:

1. A compound of formula (I), or a pharmaceutically or veterinary acceptable salt thereof, or any stereoisomer or mixtures thereof, either of the compound of formula (I) or of any of its pharmaceutically or veterinary acceptable salts

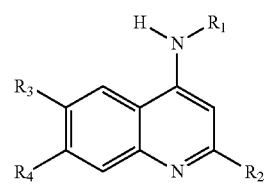

wherein:
$R_1$ is $R^a$;
$R_2$ is a known ring system selected from the group consisting of:
  (i) 5- to 6-membered heteroaromatic ring;
  (ii) phenyl fused to a 3- to 7-membered saturated or partially unsaturated or aromatic carbocyclic or heterocyclic monocyclic ring;
  (iii) 5- to 6-membered heteroaromatic ring fused to a 3- to 7-membered saturated or partially unsaturated or aromatic carbocyclic or heterocyclic monocyclic ring;
  (iv) phenyl fused to a 6- to 14-membered saturated or partially unsaturated carbocyclic or heterocyclic bicyclic ring, wherein the rings of the bicyclic ring are spiro-fused; and
  (v) 5- to 6-membered heteroaromatic ring fused to a 6- to 14-membered saturated or partially unsaturated carbocyclic or heterocyclic bicyclic ring, wherein the rings of the bicyclic ring are spiro-fused;
wherein $R_2$ is optionally substituted with:
  a) one $Cy^1$ or one $Cy^2$, and/or
  b) one or more substituents $R^b$, and/or
  c) one or more substituents $Z^1$ optionally substituted with one or more substituents $R^b$ and/or one $Cy^1$;
wherein $Cy^1$ or $Cy^2$ are optionally substituted with one or more substituents independently selected from $R^b$, and $Z^2$ optionally substituted with one or more substituents $R^b$;
$R_3$ is selected from $R^c$, halogen, —$NO_2$, —CN, —$OR^{c'}$, —OC(O)$R^{c'}$, —OC(O)O$R^{c'}$, —OC(O)N$R^{c'}R^{c'}$, —N$R^{c'}R^{c'}$, —N$R^{c'}$C(O)$R^{c'}$, —N$R^{c'}$C(O)O$R^{c'}$, —N$R^{c'}$C(O)N$R^{c'}R^{c'}$, —N$R^{c'}$S(O)$_2R^{c'}$, —N$R^{c'}SO_2NR^{c'}R^{c'}$, —S$R^{c'}$, —S(O)$R^{c'}$, —S(O)O$R^{c'}$, —$SO_2R^{c'}$, —$SO_2$ (OR$^{c'}$), —SO$_2$NR$^{c'}$R$^{c'}$, —SC(O)NR$^{c'}$R$^{c'}$, —C(O)R$^{c'}$, —C(O)OR$^{c'}$, —C(O)NR$^{c'}$R$^{c'}$, and —C(O)NR$^{c'}$OR$^{c'}$, and —C(O)NR$^{c'}$SO$_2$R$^{c'}$;

R$_4$ is —OR$^a$;

each R$^a$ is independently Cy$^2$, or Z$^3$ optionally substituted with one or more substituents R$^b$ and/or one Cy$^3$;

wherein Cy$^2$ is optionally substituted with:
  a) one Cy$^4$; and/or
  b) one or more substituents R$^b$, and/or
  c) one or more substituents Z$^4$ optionally substituted with one or more substituents R$^b$ and/or one Cy$^4$;
  wherein Cy$^4$ is optionally substituted with one or more substituents independently selected from R$^b$, and Z$^5$ optionally substituted with one or more substituents R$^b$; and wherein Cy$^3$ is optionally substituted with:
  a) one Cy$^5$; and/or
  b) one or more substituents R$^b$, and/or
  c) one or more substituents Z$^6$ optionally substituted with one or more substituents R$^b$ and/or one Cy$^5$;
  wherein Cy$^5$ is optionally substituted with one or more substituents independently selected from R$^b$, and Z$^7$ optionally substituted with one or more substituents R$^b$;

each R$^b$ is independently selected from halogen, —NO$_2$, —CN, —OR$^{c'}$, —OC(Y)R$^{c'}$, —OC(Y)OR$^{c'}$, —OC(Y)NR$^{c'}$R$^{c'}$, —NR$^{c'}$R$^{c'}$, —NR$^{c'}$C(Y)R$^{c'}$, —NR$^{c'}$C(Y)OR$^{c'}$, —NR$^{c'}$C(Y)NR$^{c'}$R$^{c'}$, —NR$^{c'}$S(O)$_2$R$^{c'}$, —NR$^{c'}$SO$_2$NR$^{c'}$R$^{c'}$, —SR$^{c'}$, —S(O)R$^{c'}$, —S(O)OR$^{c'}$, —SO$_2$R$^{c'}$, —SO$_2$(OR$^{c'}$), —SO$_2$NR$^{c'}$R$^{c'}$, —SC(Y)NR$^{c'}$R$^{c'}$, —C(Y)R$^{c'}$, —C(Y)OR$^{c'}$, —C(Y)NR$^{c'}$R$^{c'}$, —C(Y)NR$^{c'}$OR$^{c'}$, and —C(O)NR$^{c'}$SO$_2$R$^{c'}$;

each R$^{c'}$ is independently H or R$^c$;

each R$^c$ is independently selected from the group consisting of (C$_1$-C$_6$)alkyl, (C$_2$-C$_6$)alkenyl, (C$_2$-C$_6$)alkynyl, (C$_2$-C$_6$)hydrocarbon chain having one or more double bonds and one or more triple bonds, and 3- to 7-membered saturated or partially unsaturated or aromatic carbocyclic or heterocyclic monocyclic ring, wherein each R$^c$ is optionally substituted with one or more halogen atoms, Y is O, S, or NR$^{c'}$;

Z$^1$, Z$^2$, Z$^3$, Z$^4$, Z$^5$, Z$^6$ and Z$^7$ are independently selected from the group consisting of (C$_1$-C$_{12}$)alkyl, (C$_2$-C$_{12}$)alkenyl, (C$_2$-C$_{12}$)alkynyl, and (C$_2$-C$_6$)hydrocarbon chain having one or more double bonds and one or more triple bonds;

Cy$^1$, Cy$^4$ and Cy$^5$ are independently a known ring system selected from the group consisting of phenyl; 3- to 7-membered carbocyclic or heterocyclic monocyclic ring, saturated or partially unsaturated; and 5- or 6-membered heteroaromatic ring;

Cy$^2$ and Cy$^3$ are independently a known ring system selected from group consisting of phenyl; 5- or 6-membered heteroaromatic ring; 3- to 7-membered carbocyclic or heterocyclic monocyclic ring, which is saturated or partially unsaturated; and 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring;

wherein in the carbocyclic rings all ring members are carbon atoms; and in the heterocyclic and heteroaromatic rings one or more ring members are selected from N, O, and S; and wherein in all saturated or partially unsaturated rings one or two members of the rings are optionally C(O) and/or C(NH) and/or C[N(C$_1$-C$_4$)alkyl].

2. The compound of formula (I) according to claim 1, wherein R$_3$ is —OR$^{c'}$.

3. The compound of formula (I) according to claim 1, wherein R$^a$ in R$_4$ is Z$^3$ optionally substituted as defined in claim 1.

4. The compound of formula (I) according to claim 1, wherein
R$_2$ is a known ring system selected from the group consisting of:
  (i) 5- to 6-membered heteroaromatic ring;
  (ii) phenyl fused to a 3- to 7-membered saturated or partially unsaturated or aromatic carbocyclic or heterocyclic monocyclic ring; and
  (iii) 5- to 6-membered heteroaromatic ring fused to a 3- to 7-membered saturated or partially unsaturated or aromatic carbocyclic or heterocyclic monocyclic ring;
wherein R$_2$ is optionally substituted as defined in claim 1.

5. The compound of formula (I) according to claim 4, wherein R$_2$ is 5- to 6-membered heteroaromatic monocyclic ring.

6. A pharmaceutical or veterinary composition which comprises a therapeutically effective amount of a compound of formula (I) as defined in claim 1, or a pharmaceutically or veterinary acceptable salt thereof, or any stereoisomer either of the compound of formula (I) or of its pharmaceutically or veterinary acceptable salt, together with one or more pharmaceutically or veterinary acceptable excipients or carriers.

7. A method for the treatment of cancer mediated by the inhibition of histone methyltransferase G9a and of one or more DNMTs selected from the group consisting of DNMT1, DNMT3A and DNMT3B, comprising administering an effective amount of a compound of claim 1, or a pharmaceutically or veterinary acceptable salt thereof, or any stereoisomer or mixtures thereof, either of the compound of claim 1 or of any of its pharmaceutically or veterinary acceptable salts, and one or more pharmaceutically or veterinary acceptable excipients or carriers, in a subject in need thereof;
wherein the cancer is selected from the group consisting of Acute Lymphocytic Leukemia (ALL), Diffuse Large B-cell lymphoma (DLBCL), bladder cancer, breast cancer, cervical cancer, colorectal cancer, glioblastoma, hepatocarcinoma, melanoma, pancreatic cancer, prostate cancer, renal cancer, small-cell lung cancer, non small-cell lung cancer, acute myeloid leukemia, mantle cell lymphoma and multiple myeloma.

8. The method according to claim 7, R$_2$ is 5- to 6-membered heteroaromatic monocyclic ring.

9. A method for generating an induced pluripotent stem cell, the method comprising the step of culturing an isolated cell together with one or more transcription factors and a compound of claim 1, or a pharmaceutically or veterinary acceptable salt thereof, or any stereoisomer or mixtures thereof, either of the compound of claim 1 or of any of its pharmaceutically or veterinary acceptable salts.

10. The compound of formula (I) according to claim 1, wherein
R$_3$ is —OR$^{c'}$ and R$_2$ is a known ring system selected from the group consisting of:
(ii) 5- to 6-membered heteroaromatic ring;
(iii) phenyl fused to a 3- to 7-membered saturated or partially unsaturated or aromatic carbocyclic or heterocyclic monocyclic ring; and
(iv) 5- to 6-membered heteroaromatic ring fused to a 3- to 7-membered saturated or partially unsaturated or aromatic carbocyclic or heterocyclic monocyclic ring;
wherein R$_2$ is optionally substituted as defined in claim 1.

11. The compound of formula (I) according to claim 1, wherein in R$_1$, Cy$^2$ and Cy$^3$ are independently a known ring system selected from a 3- to 7-membered carbocyclic or heterocyclic monocyclic ring, which is saturated or partially unsaturated; and a 3- to 7-membered saturated or partially unsaturated or aromatic carbocyclic or heterocyclic monocyclic ring, which is fused, bridged-fused or spiro-fused to a 3- to 7-membered saturated or partially unsaturated or aromatic carbocyclic or heterocyclic monocyclic ring.

12. The method according to claim 7, wherein the subject is a human.

13. The compound of claim 1, which is 6-methoxy-2-(5-methyl-2-furyl)-N-methyl-4-piperidyl)-7-(3-pyrrolidin-1-ylpropoxy)quinolin-4-amine.

14. The compound of claim 1, wherein
R$_1$ is 1-methylpiperidin-4-yl or (1-methylpiperidin-4-yl)methyl;
R$_2$ is 2,5-dimethylfuran-3-yl or 5-methylfuran-2-yl;
R$_3$ is methoxy; and
R$_4$ is 3-(pyrrolidin-1-yl)propan-1-oxy.

* * * * *